United States Patent
Satoh et al.

(10) Patent No.: US 9,750,252 B2
(45) Date of Patent: Sep. 5, 2017

(54) ARYLALKYLOXY PYRIMIDINE DERIVATIVE, PESTICIDE FOR AGRICULTURAL AND HORTICULTURAL USE CONTAINING ARYLALKYLOXY PYRIMIDINE DERIVATIVE AS ACTIVE INGREDIENT, AND USE OF SAME

(71) Applicant: NIHON NOHYAKU CO., LTD., Tokyo (JP)

(72) Inventors: Eikou Satoh, Kawachinagano (JP); Tetsuya Murata, Kawachinagano (JP); Hiroto Harayama, Kawachinagano (JP); Motofumi Nakano, Kawachinagano (JP); Kosuke Fukatsu, Kawachinagano (JP); Kayo Inukai, Kawachinagano (JP); Ryota Kasahara, Kawachinagano (JP); Yutaka Abe, Kawachinagano (JP); Nobuyuki Hayashi, Kawachinagano (JP); Naoya Fujita, Kawachinagano (JP)

(73) Assignee: Nihon Nohyaku., Ltd., Tokyo (JP)

(*) Notice: Subject to any disclaimer, the term of this patent is extended or adjusted under 35 U.S.C. 154(b) by 347 days.

(21) Appl. No.: 14/375,060

(22) PCT Filed: Feb. 1, 2013

(86) PCT No.: PCT/JP2013/052421
§ 371 (c)(1),
(2) Date: Jul. 28, 2014

(87) PCT Pub. No.: WO2013/115391
PCT Pub. Date: Aug. 8, 2013

(65) Prior Publication Data
US 2015/0005257 A1    Jan. 1, 2015

(30) Foreign Application Priority Data

Feb. 1, 2012 (JP) ................. 2012-019768
Aug. 1, 2012 (JP) ................. 2012-171532

(51) Int. Cl.
*A01N 43/54* (2006.01)
*A01N 55/00* (2006.01)
(Continued)

(52) U.S. Cl.
CPC ............ *A01N 43/54* (2013.01); *A01N 43/56* (2013.01); *A01N 43/653* (2013.01); *A01N 43/76* (2013.01); *A01N 43/78* (2013.01); *A01N 43/80* (2013.01); *A01N 43/82* (2013.01); *A01N 43/84* (2013.01); *A01N 43/90* (2013.01); *A01N 47/02* (2013.01); *A01N 47/28* (2013.01); *A01N 55/00* (2013.01); *C07D 239/34* (2013.01); *C07D 239/52* (2013.01); *C07D 401/04* (2013.01); *C07D 401/06* (2013.01); *C07D 401/12* (2013.01); *C07D 403/04* (2013.01); *C07D 403/06* (2013.01); *C07D 405/04* (2013.01); *C07D 405/06* (2013.01); *C07D 405/14* (2013.01); *C07D 409/04* (2013.01); (Continued)

(58) Field of Classification Search
None
See application file for complete search history.

(56) References Cited

U.S. PATENT DOCUMENTS 5,246,938 A  9/1993 Turnbull et al.
5,571,815 A  11/1996 Schaper et al.
(Continued)

FOREIGN PATENT DOCUMENTS

CN     1071419 A     4/1998
CN   101311170 A    11/2008
(Continued)

OTHER PUBLICATIONS

CAPLUS printout of Foreign Patent Application Publication No. WO9611902, published on Apr. 25, 1996.*
(Continued)

*Primary Examiner* — Alicia L Otton
*Assistant Examiner* — Po-Chih Chen
(74) *Attorney, Agent, or Firm* — Leydig, Voit & Mayer, Ltd.

(57) ABSTRACT

An arylalkyloxypyrimidine derivative represented by the formula (I)

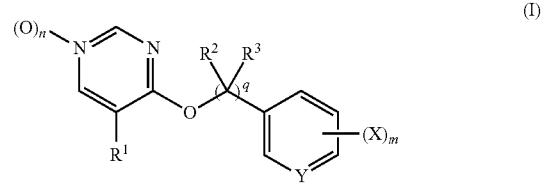

wherein $R^1$ is an alkyl group, a cycloalkyl group, an alkenyl group, an alkynyl group, a haloalkyl group, a haloalkenyl group, a haloalkynyl group, an alkoxyalkyl group, a dioxolane group and the like; $R^2$ and $R^3$ are each a hydrogen atom, an alkyl group and the like; X is an alkyl group, a cycloalkyl group, an alkenyl group, an alkynyl group, a haloalkyl group, a haloalkenyl group, a haloalkynyl group, a trialkylsilyl group and the like; Y is CH or a nitrogen atom; q is an integer of 1 to 3; m is an integer of 0 to 5; and n is 0 or 1 or a salt thereof, and an agrohorticultural insecticide containing the compound as an active ingredient and a method of use thereof.

9 Claims, No Drawings

(51) Int. Cl.
| | | |
|---|---|---|
| *C07F 7/08* | (2006.01) | |
| *A01N 43/80* | (2006.01) | |
| *A01N 43/76* | (2006.01) | |
| *A01N 43/82* | (2006.01) | |
| *A01N 43/78* | (2006.01) | |
| *A01N 43/90* | (2006.01) | |
| *A01N 43/84* | (2006.01) | |
| *C07D 401/04* | (2006.01) | |
| *C07D 409/04* | (2006.01) | |
| *C07D 405/04* | (2006.01) | |
| *C07D 403/06* | (2006.01) | |
| *C07D 413/04* | (2006.01) | |
| *C07D 411/04* | (2006.01) | |
| *C07D 417/04* | (2006.01) | |
| *C07D 493/04* | (2006.01) | |
| *C07D 239/52* | (2006.01) | |
| *C07D 495/10* | (2006.01) | |
| *C07D 239/34* | (2006.01) | |
| *A01N 43/56* | (2006.01) | |
| *A01N 43/653* | (2006.01) | |
| *A01N 47/02* | (2006.01) | |
| *A01N 47/28* | (2006.01) | |
| *C07D 405/14* | (2006.01) | |
| *C07D 401/06* | (2006.01) | |
| *C07D 403/04* | (2006.01) | |
| *C07D 493/08* | (2006.01) | |
| *C07D 493/10* | (2006.01) | |
| *C07D 497/10* | (2006.01) | |
| *C07F 7/18* | (2006.01) | |
| *C07D 401/12* | (2006.01) | |
| *C07D 405/06* | (2006.01) | |
| *C07D 413/06* | (2006.01) | |

(52) U.S. Cl.
CPC .......... *C07D 411/04* (2013.01); *C07D 413/04* (2013.01); *C07D 413/06* (2013.01); *C07D 417/04* (2013.01); *C07D 493/04* (2013.01); *C07D 493/08* (2013.01); *C07D 493/10* (2013.01); *C07D 495/10* (2013.01); *C07D 497/10* (2013.01); *C07F 7/0812* (2013.01); *C07F 7/1852* (2013.01); *C07F 7/1856* (2013.01)

(56) References Cited

U.S. PATENT DOCUMENTS

| | | | |
|---|---|---|---|
| 5,811,459 | A | 9/1998 | Breault et al. |
| 5,852,023 | A | 12/1998 | Schaper et al. |
| 5,859,020 | A | 1/1999 | Preuss et al. |
| 5,889,012 | A | 3/1999 | Märkl et al. |
| 6,114,342 | A | 9/2000 | Oberdorf et al. |
| 6,166,026 | A | 12/2000 | Rack et al. |
| 6,265,398 | B1 | 7/2001 | Braun et al. |
| 6,310,071 | B1 | 10/2001 | Oberdorf et al. |
| 6,596,727 | B1 | 7/2003 | Schaper et al. |
| 8,383,640 | B2 | 2/2013 | Liu et al. |
| 8,895,574 | B2* | 11/2014 | Kasahara ............. C07D 239/34 514/269 |
| 2010/0113490 | A1 | 5/2010 | Liu et al. |
| 2010/0297073 | A1 | 11/2010 | Chin et al. |
| 2013/0267564 | A1 | 10/2013 | Kasahara et al. |

FOREIGN PATENT DOCUMENTS

| | | |
|---|---|---|
| CN | 102307863 B | 5/2014 |
| JP | H06-256319 A | 9/1994 |
| JP | H07-506347 A | 7/1995 |
| JP | 08-283246 A | 10/1996 |
| JP | 09-511529 A | 11/1997 |
| JP | H10-507188 A | 7/1998 |
| JP | 10-512236 A | 11/1998 |
| JP | H11-503115 A | 3/1999 |
| JP | 2000-505783 A | 5/2000 |
| JP | 2000-508647 A | 7/2000 |
| JP | 2000-510850 A | 8/2000 |
| WO | WO 96/11902 A1 | 4/1996 |
| WO | WO 96/17843 A2 | 6/1996 |
| WO | WO 99/28305 A1 | 6/1999 |
| WO | WO 2010/133528 A1 | 11/2010 |
| WO | WO 2012/008527 A1 | 1/2012 |
| WO | WO 2012/086768 A1 | 6/2012 |

OTHER PUBLICATIONS

CAPLUS printout of US Patent Application Publication No. 20100158860, published on Jun. 24, 2010.*
Darout et al., *Tetrahedron*, 68: 4596-4599 (2012).
European Patent Office, Supplementary European Search Report in European Patent Application No. 13744073 (Jul. 30, 2015).
Asakawa et al., *Chem. Pharm. Bull.*, 27(6): 1468-1472 (1979).
Okano et al., *Yakugaku Zasshi*, 87(11): 1315-1321 (1967).
Slavish et al., *Bioorganic & Medicinal Chemistry Letters*, 21: 4592-4596 (2011).
Japanese Patent Office, International Search Report in International Patent Application No. PCT/JP2013/052421 (Mar. 5, 2013).
Japanese Patent Office, International Preliminary Report on Patentability in International Patent Application No. PCT/JP2013/052421 (Aug. 5, 2014).
Chinese Patent Office, First Office Action in Chinese Patent Application No. 201380017729.3 (May 12, 2015).

* cited by examiner

ARYLALKYLOXY PYRIMIDINE DERIVATIVE, PESTICIDE FOR AGRICULTURAL AND HORTICULTURAL USE CONTAINING ARYLALKYLOXY PYRIMIDINE DERIVATIVE AS ACTIVE INGREDIENT, AND USE OF SAME

CROSS-REFERENCE TO RELATED APPLICATIONS

This patent application is the U.S. national phase of International Patent Application No. PCT/JP2013/052421, filed Feb. 1, 2013, which claims the benefit of Japanese Patent Application No. 2012-171532, filed on Aug. 1, 2012, and Japanese Patent Application No. 2012-019768, filed on Feb. 1, 2012, which are incorporated by reference in their entireties herein.

TECHNICAL FIELD OF THE INVENTION

The present invention relates to an agrohorticultural insecticide containing an arylalkyloxypyrimidine derivative or a salt thereof as an active ingredient, and a method of use thereof.

BACKGROUND OF THE INVENTION

Patent document 1 suggests that a derivative wherein the 4-position of pyrimidine ring is substituted by an arylalkyloxy group has an antifungal or insecticidal activity. In addition, patent document 2 describes that a certain kind of pyrimidine derivative is useful as a pharmaceutical product. However, it contains no description relating to an insecticidal activity.

DOCUMENT LIST

Patent Documents patent document 1: JP-A-08-283246
patent document 2: WO1996/011902

SUMMARY OF THE INVENTION

Problems to be Solved by the Invention

In crop manufacturing in agricultural and horticultural fields, damages caused by insect pests are still serious, and development of novel agrohorticultural insecticides and acaricides is desired due to generation of insect pests resistant to known agents, and the like. Since various labor saving farm works are required due to increasing numbers of the aged farm working population, creation of agrohorticultural insecticides and acaricides having suitable properties for the farm works is also demanded.

Means of Solving the Problems

The present inventors have conducted intensive studies in an attempt to develop a novel agrohorticultural insecticide, and have found that the arylalkyloxypyrimidine derivative or a salt thereof represented by the formula (I) of the present invention is useful as an agrohorticultural insecticide, which resulted in the completion of the present invention.

Accordingly, the present invention relates to [1] an arylalkyloxypyrimidine derivative represented by the formula (I):

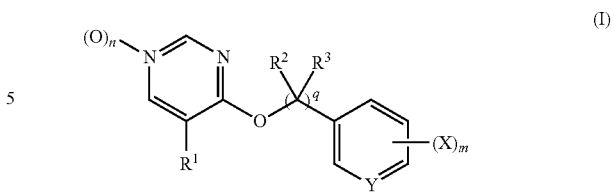

wherein $R^1$ is
(a1) a halogen atom;
(a2) a formyl group;
(a3) a cyano group;
(a4) a $(C_1-C_8)$alkyl group;
(a5) a $(C_3-C_8)$cycloalkyl group;
(a6) a $(C_2-C_8)$alkenyl group;
(a7) a $(C_2-C_8)$alkynyl group;
(a8) a halo$(C_1-C_8)$alkyl group;
(a9) a halo$(C_3-C_8)$cycloalkyl group;
(a10) a halo$(C_2-C_8)$alkenyl group;
(a11) a halo$(C_2-C_8)$alkynyl group;
(a12) a $(C_1-C_8)$alkoxy$(C_1-C_8)$alkyl group;
(a13) a $(C_3-C_8)$cycloalkyl$(C_1-C_8)$alkyl group;
(a14) a $(C_1-C_8)$alkoxyhalo$(C_1-C_8)$alkyl group;
(a15) a $(C_3-C_8)$cycloalkylhalo$(C_1-C_8)$alkyl group;
(a16) a $(C_1-C_8)$alkylthio$(C_1-C_8)$alkyl group;
(a17) a $(C_1-C_8)$alkylsulfinyl$(C_1-C_8)$alkyl group;
(a18) a $(C_1-C_8)$alkylsulfonyl$(C_1-C_8)$alkyl group;
(a19) a halo$(C_1-C_8)$alkoxy$(C_1-C_8)$alkyl group;
(a20) a halo$(C_3-C_8)$cycloalkyl$(C_1-C_8)$alkyl group;
(a21) a halo$(C_1-C_8)$alkylthio$(C_1-C_8)$alkyl group;
(a22) a halo$(C_1-C_8)$alkylsulfinyl$(C_1-C_8)$alkyl group;
(a23) a halo$(C_1-C_8)$alkylsulfonyl$(C_1-C_8)$alkyl group;
(a24) a halo$(C_1-C_8)$alkoxyhalo$(C_1-C_8)$alkyl group;
(a25) a cyano$(C_1-C_8)$alkyl group;
(a26) a nitro $(C_1-C_8)$alkyl group;
(a27) a $R^4 (R^5) N(C_1-C_8)$alkyl group wherein $R^4$ and $R^5$ may be the same or different and each is (i) a hydrogen atom, (ii) a $(C_1-C_6)$alkyl group, (iii) a $(C_3-C_6)$cycloalkyl group, (iv) a $(C_2-C_6)$alkenyl group, (v) a $(C_2-C_6)$alkynyl group, (vi) a $(C_3-C_6)$cycloalkyl$(C_1-C_6)$alkyl group, (vii) a halo$(C_1-C_6)$alkyl group, (viii) a halo$(C_3-C_6)$cycloalkyl group, (ix) a halo$(C_2-C_6)$alkenyl group, (x) a halo$(C_2-C_6)$alkynyl group, (xi) a halo$(C_3-C_6)$cycloalkyl$(C_1-C_6)$alkyl group, (xii) a $(C_1-C_6)$alkylsulfonyl group, (xiii) a $(C_1-C_6)$alkylcarbonyl group, (xiv) a halo$(C_1-C_6)$alkylcarbonyl group, (xv) a $(C_1-C_6)$alkoxycarbonyl group, (xvi) a $(C_3-C_6)$cycloalkylcarbonyl group, (xvii) a phenyl group, (xviii) a phenyl group having, on the ring, the same or different 1 to 5 substituents selected from (a) a halogen atom, (b) a $(C_1-C_6)$alkyl group, (c) a halo$(C_1-C_6)$alkyl group, (d) a $(C_1-C_6)$alkoxy group, (e) a halo$(C_1-C_6)$alkoxy group, and (f) a phenoxy group, (xix) a phenoxyphenyl group having, on the ring, the same or different 1 to 5 substituents selected from (a) a halogen atom, (b) a $(C_1-C_6)$alkyl group, (c) a halo$(C_1-C_6)$alkyl group, (d) a $(C_1-C_6)$alkoxy group, and (e) a halo$(C_1-C_6)$alkoxy group, (xx) a hydroxy$(C_1-C_8)$alkyl group, (xxi) a phenyl$(C_1-C_6)$alkyl group, (xxii) a phenyl$(C_1-C_6)$alkyl group having, on the ring, the same or different 1 to 5 substituents selected from (a) a halogen atom, (b) a $(C_1-C_6)$alkyl group, (c) a halo$(C_1-C_6)$alkyl group, (d) a $(C_1-C_6)$alkoxy group, (e) halo$(C_1-C_6)$alkoxy group, and (f) a phenoxy group, or (xxiii) a phenoxyphenyl$(C_1-C_6)$alkyl group having, on the ring, the same or different 1 to 5 substituents selected from (a)

a halogen atom, (b) a ($C_1$-$C_6$)alkyl group, (c) a halo($C_1$-$C_6$)alkyl group, (d) a ($C_1$-$C_6$)alkoxy group, and (e) a halo($C_1$-$C_6$)alkoxy group;

(a28) a ($R^4$)OC($C_1$-$C_8$)alkyl group wherein $R^4$ is as defined above;

(a29) a ($R^4$)O$_2$C($C_1$-$C_8$)alkyl group wherein $R^4$ is as defined above;

(a30) a $R^4(R^5)$NCO($C_1$-$C_8$)alkyl group wherein $R^4$ and $R^5$ are as defined above;

(a31) an aryl group;

(a32) an aryl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above and (t) a phenoxy group;

(a33) an aryl($C_1$-$C_8$)alkyl group;

(a34) an aryl($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a35) an arylcarbonyl group;

(a36) an arylcarbonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a37) an arylthio($C_1$-$C_8$)alkyl group;

(a38) an arylthio($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a39) an arylsulfinyl($C_1$-$C_8$)alkyl group;

(a40) an arylsulfinyl($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a41) an arylsulfonyl($C_1$-$C_8$)alkyl group;

(a42) an arylsulfonyl($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;

(a43) a ($C_1$-$C_8$)alkylcarbonyl group;

(a44) a ($C_3$-$C_8$)cycloalkylcarbonyl group;

(a45) a ($C_1$-$C_8$)alkoxycarbonyl group;

(a46) a $R^4(R^5)$N carbonyl group wherein $R^4$ and $R^5$ are as defined above;

(a47) a ($C_1$-$C_8$)alkoxy($C_1$-$C_8$)alkoxy($C_1$-$C_8$)alkyl group;

(a48) a ($C_1$-$C_8$)alkoxycarbonyl($C_1$-$C_8$)alkyl group;

(a49) a heterocyclic group;

(a50) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_3$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a phenyl group, (u) an oxo group and (v) a ($C_1$-$C_6$)alkoxycarbonyl($C_1$-$C_6$)alkyl group;

(a51) a heterocyclyl($C_1$-$C_8$)alkyl group;

(a52) a heterocyclyl($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_8$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above and (t) an oxo group;

(a53) a heterocyclyl($C_3$-$C_8$)cycloalkyl group;
(a54) a heterocyclyl($C_3$-$C_8$)cycloalkyl group having, on the heterocycle, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above and (t) an oxo group;
(a55) a tri($C_1$-$C_8$)alkylsilyl($C_1$-$C_8$)alkyl group wherein the alkyl groups of the tri($C_1$-$C_8$)alkylsilyl may be the same or different;
(a56) a $C(R^4)$=$NOR^5$ group wherein $R^4$ and $R^5$ are as defined above;
(a57) an oxiranyl group;
(a58) a tetrahydropyranyloxy($C_1$-$C_8$)alkyl group;
(a59) a tetrahydrofuranyloxy($C_1$-$C_8$)alkyl group;
(a60) a tetrahydropyranylcarbonyl group;
(a61) a formyloxy($C_1$-$C_6$)alkyl group;
(a62) a ($C_1$-$C_8$)alkylthio($C_1$-$C_8$)alkylcarbonyl group;
(a63) a heterocyclylcarbonyl group;
(a64) a heterocyclylcarbonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above and (t) an oxo group;
(a65) a hydroxy($C_1$-$C_8$)alkyl group;
(a66) an aryloxy($C_1$-$C_8$)alkyl group;
(a67) an aryloxy($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;
(a68) a ($C_1$-$C_8$)alkylthio($C_1$-$C_8$)alkoxy($C_1$-$C_8$)alkyl group;
(a69) a ($C_1$-$C_8$)alkylsulfinyl($C_1$-$C_8$)alkoxy($C_1$-$C_8$)alkyl group;
(a70) a (($C_1$-$C_8$)alkoxy) (($C_3$-$C_8$)cycloalkyl) ($C_1$-$C_8$)alkyl group;
(a71) a $R^4CO(R^5)N$($C_1$-$C_8$)alkyl group wherein $R^4$ and $R^5$ are as defined above;
(a72) a $R^4CO_2$ ($R^5$) N($C_1$-$C_8$)alkyl group wherein $R^4$ and $R^5$ are as defined above;
(a73) a $R^4SO_2$ ($R^5$) N($C_1$-$C_8$)alkyl group wherein $R^4$ and $R^5$ are as defined above;
(a74) a $R^4$ ($R^5$) $NCO_2$ ($C_1$-$C_8$)alkyl group wherein $R^4$ and $R^5$ are as defined above;
(a75) a ($R^4$ ($R^5$)N)(($C_3$-$C_8$)cycloalkyl) ($C_1$-$C_8$)alkyl group wherein $R^4$ and $R^5$ are as defined above;
(a76) a (($C_1$-$C_8$)alkylthio) (($C_3$-$C_8$)cycloalkyl) ($C_1$-$C_8$)alkyl group;
(a77) a (($C_1$-$C_8$)alkylsulfinyl) (($C_3$-$C_8$)cycloalkyl) ($C_1$-$C_8$) alkyl group;
(a78) a (($C_1$-$C_8$)alkylsulfonyl) (($C_3$-$C_8$)cycloalkyl) ($C_1$-$C_8$) alkyl group;
(a79) a (heterocyclyl) (($C_3$-$C_8$)cycloalkyl) ($C_1$-$C_8$)alkyl group;
(a80) a (heterocyclyl) (($C_3$-$C_8$)cycloalkyl) ($C_1$-$C_8$)alkyl group having, on the hetero ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) an oxo group;
(a81) (heterocyclyl) (($C_1$-$C_8$)alkoxy) ($C_1$-$C_8$)alkyl group;
(a82) a (heterocyclyl) (($C_1$-$C_8$)alkoxy) ($C_1$-$C_8$)alkyl group having, on the hetero ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) an oxo group;
(a83) a di($C_1$-$C_8$)alkoxy($C_1$-$C_8$)alkyl group wherein the alkoxy groups of the di($C_1$-$C_8$)alkoxy may be the same or different;
(a84) a di($C_1$-$C_8$)alkylthio($C_1$-$C_8$)alkyl group wherein the alkyl groups of the di($C_1$-$C_8$)alkylthio may be the same or different;
(a85) a tri($C_1$-$C_8$)alkylsilyloxy($C_1$-$C_8$)alkyl group wherein the alkyl groups of the tri($C_1$-$C_8$)alkylsilyl may be the same or different;
(a86) a carboxyl group;
(a87) an aryloxycarbonyl group;
(a88) a $C(R^4)$=$NOSO_2R^5$ group wherein $R^4$ and $R^5$ are as defined above;
(a89) a heterocyclylimino($C_1$-$C_8$)alkyl group;
(a90) a tri($C_1$-$C_8$)alkylsilyl($C_2$-$C_8$)alkynyl group wherein the alkyl groups of the tri($C_1$-$C_8$)alkylsilyl may be the same or different;
(a91) a ($C_1$-$C_8$)alkoxy($C_2$-$C_8$)alkynyl group;
(a92) a hydroxy($C_2$-$C_8$)alkynyl group;
(a93) a (hydroxy)(($C_1$-$C_8$)alkoxy($C_1$-$C_8$)alkoxy)($C_1$-$C_8$) alkyl group;
(a94) a dihydroxy($C_1$-$C_8$)alkyl group;
(a95) a (hydroxy) (($C_1$-$C_8$)alkoxy) ($C_1$-$C_8$)alkyl group;
(a96) a di($C_1$-$C_8$)alkylsulfonyloxy($C_1$-$C_8$)alkyl group wherein the alkyl groups of the di($C_1$-$C_8$)alkylsulfonyloxy may be the same or different;

(a97) a di(($C_1$-$C_8$)alkoxy($C_1$-$C_8$)alkoxy)($C_1$-$C_8$)alkyl group wherein the alkoxy groups of the di(($C_1$-$C_8$)alkoxy($C_1$-$C_8$)alkoxy may be the same or different;

(a98) a di($C_1$-$C_8$)alkoxycarbonyl($C_2$-$C_8$)alkenyl group wherein the alkoxy groups of the di($C_1$-$C_8$)alkoxycarbonyl may be the same or different;

(a99) a ($C_1$-$C_8$)alkoxycarbonyl(cyano)($C_2$-$C_8$)alkenyl group;

(a100) a (($C_1$-$C_8$)alkoxy($C_1$-$C_8$)alkoxy)(hydroxy)($C_1$-$C_8$)alkyl group;

(a101) a dicyano($C_2$-$C_8$)alkenyl group;

(a102) a ($C_3$-$C_8$)cycloalkylidene($C_1$-$C_8$)alkyl group;

(a103) a ($C_3$-$C_8$)cycloalkyl(hydroxy)($C_1$-$C_8$)alkyl group;

(a104) a ($C_3$-$C_8$)cycloalkyl(($C_1$-$C_8$)alkoxy)($C_1$-$C_8$)alkyl group;

(a105) a heterocyclyl($C_2$-$C_8$)alkenyl group;

(a106) a heterocyclyl($C_2$-$C_8$)alkenyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) an oxo group;

(a107) a halo($C_1$-$C_8$)alkylcarbonyloxy($C_2$-$C_8$)alkenyl group;

(a108) a ($C_3$-$C_8$)cycloalkyl(halo($C_1$-$C_8$)alkylcarbonyloxy)($C_1$-$C_8$)alkyl group;

(a109) a ($C_1$-$C_8$)alkoxycarbonyl(hydroxy)($C_1$-$C_8$)alkyl group;

(a110) a carboxy(hydroxy)($C_1$-$C_8$)alkyl group;

(a111) a di($C_1$-$C_8$)alkoxycarbonyl($C_3$-$C_8$)cycloalkyl group wherein the alkoxy groups of the di($C_1$-$C_8$)alkoxycarbonyl may be the same or different;

(a112) a di($C_1$-$C_8$)alkoxycarbonyl($C_1$-$C_8$)alkyl group wherein the alkoxy groups of the di($C_1$-$C_8$)alkoxycarbonyl may be the same or different;

(a113) a ($C_1$-$C_8$)alkylcarbonyl($C_2$-$C_8$)alkenyl group;

(a114) a hydroxyhalo($C_1$-$C_8$)alkyl group;

(a115) a dihydroxyhalo($C_1$-$C_8$)alkyl group;

(a116) a ($C_1$-$C_8$)alkoxycarbonyl($C_3$-$C_8$)cycloalkyl group;

(a117) a cyano($C_3$-$C_8$)cycloalkyl group;

(a118) a ($C_1$-$C_8$)alkoxycarbonyl($C_2$-$C_8$)alkenyl group;

(a119) a cyano($C_2$-$C_8$)alkenyl group;

(a120) a (($C_1$-$C_8$)alkoxy)(hydroxy)halo($C_1$-$C_8$)alkyl group;

(a121) a $R^4(R^5)$N($C_1$-$C_8$)alkyl($R^5$)N carbonyl group wherein $R^4$ and $R^5$ are as defined above;

(a122) a $R^4(R^5)$NCO($R^5$)N($C_1$-$C_8$)alkyl group wherein $R^4$ and $R^5$ are as defined above;

(a123) a tri($C_1$-$C_8$)alkylsilyl($C_2$-$C_8$)alkynyl($C_2$-$C_8$)alkenyl group wherein the alkyl groups of the tri($C_1$-$C_8$)alkylsilyl may be the same or different; or (a124) the following structural formula $Q^1$, $Q^2$, $Q^3$, $Q^4$, $Q^5$, $Q^6$, $Q^7$, $Q^8$, $Q^9$, $Q^{10}$, $Q^{11}$, $Q^{12}$, $Q^{13}$, $Q^{14}$, $Q^{15}$, $Q^{16}$, $Q^{17}$, $Q^{18}$, $Q^{19}$, $Q^{20}$, $Q^{21}$, $Q^{22}$, $Q^{23}$, $Q^{24}$, $Q^{25}$, $Q^{26}$, $Q^{27}$, $Q^{28}$, or $Q^{29}$

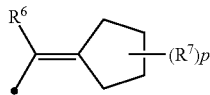

$Q^1$

-continued

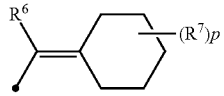

$Q^2$

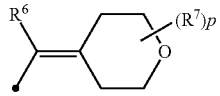

$Q^3$

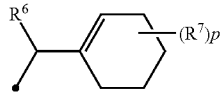

$Q^4$

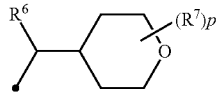

$Q^5$

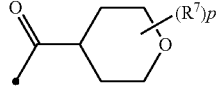

$Q^6$

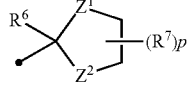

$Q^7$

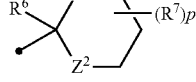

$Q^8$

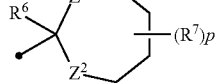

$Q^9$

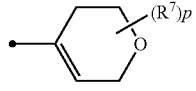

$Q^{10}$

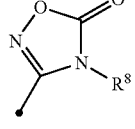

$Q^{11}$

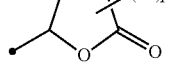

$Q^{12}$

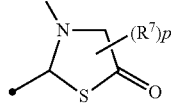

$Q^{13}$

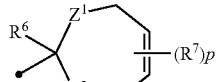

$Q^{14}$

-continued

Q15 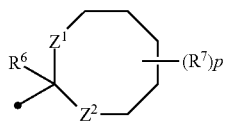

Q16 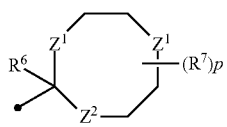

Q17 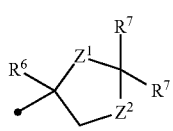

Q18 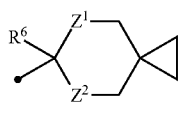

Q19 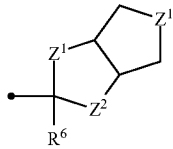

Q20 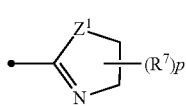

Q21 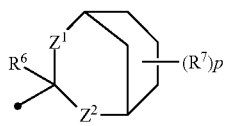

Q22 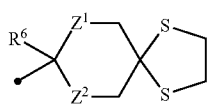

Q23 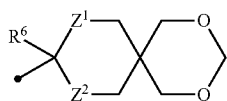

Q24 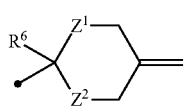

Q25 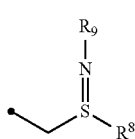

Q26 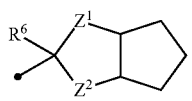

-continued

Q27 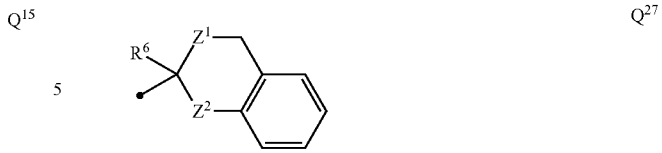

Q28 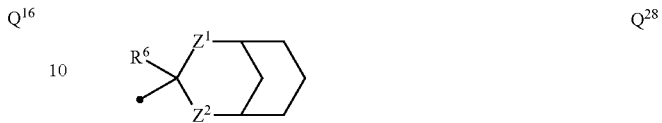

Q29 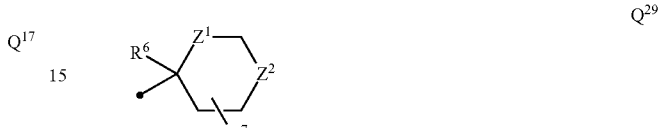

wherein $R^6$, $R^7$ and $R^8$ may be the same or different and each is a hydrogen atom, a $(C_1-C_6)$alkyl group, a $(C_3-C_6)$cycloalkyl group, a $(C_2-C_6)$alkenyl group, a $(C_2-C_6)$alkynyl group, a $(C_3-C_6)$cycloalkyl$(C_1-C_6)$alkyl group, a halo$(C_1-C_6)$alkyl group, a halo$(C_3-C_6)$cycloalkyl group, a halo$(C_2-C_6)$alkenyl group, a halo$(C_2-C_6)$alkynyl group, a halo$(C_3-C_6)$cycloalkyl$(C_1-C_6)$alkyl group, a $(C_1-C_6)$alkylcarbonyloxy$(C_1-C_6)$alkyl group, a $(C_1-C_6)$alkoxy$(C_1-C_6)$alkyl group, a hydroxy$(C_1-C_6)$alkyl group, a $(C_2-C_6)$alkenyloxy$(C_1-C_6)$alkyl group, a phenoxy$(C_1-C_6)$alkyl group, a $(C_1-C_6)$alkylsulfonyl$(C_1-C_6)$alkyl group, a $(C_1-C_6)$alkylsulfonyloxy$(C_1-C_6)$alkyl group, a halogen atom, a phenyl group, a phenyl$(C_1-C_6)$alkyl group, or a $(C_1-C_6)$alkylcarbonyl group, $R^9$ is a cyano group, a halo$(C_1-C_6)$alkyl group, or a halo$(C_1-C_6)$alkylcarbonyl group, p is an integer of 0 to 5, and $Z^1$ and $Z^2$ may be the same or different and each is a carbon atom, an oxygen atom, S, SO, $SO_2$ or $NR^6$ wherein $R^6$ is as defined above, or when p is 2, the adjacent two $R^7$ can be bonded to form a 3- to 8-membered aliphatic ring.

$R^2$ and $R^3$ may be the same or different and each is (b1) a hydrogen atom;
(b2) a $(C_1-C_8)$alkyl group;
(b3) a $(C_3-C_8)$cycloalkyl group;
(b4) a $(C_2-C_8)$alkenyl group;
(b5) a $(C_2-C_8)$alkynyl group;
(b6) a halo$(C_1-C_8)$alkyl group;
(b7) a halo$(C_3-C_8)$cycloalkyl group;
(b8) a halo$(C_2-C_8)$alkenyl group;
(b9) a halo$(C_2-C_8)$alkynyl group;
(b10) a $(C_3-C_8)$cycloalkyl$(C_1-C_8)$alkyl group;
(b11) a $(C_1-C_8)$alkoxy$(C_1-C_8)$alkyl group;
(b12) a $(C_1-C_8)$alkylthio$(C_1-C_8)$alkyl group; or
(b13) a $(C_1-C_8)$alkoxycarbonyl group, q is an integer of 1 to 3.

X may be the same or different and each is (c1) a hydrogen atom;
(c2) a halogen atom;
(c3) a hydroxyl group;
(c4) a cyano group;
(c5) a nitro group;
(c6) an $N(R^4)(R^5)$ group wherein $R^4$ and $R^5$ are as defined above;
(c7) an $N(R^4)CO(R^5)$ group wherein $R^4$ and $R^5$ are as defined above;
(c8) an $N(R^4)SO_2(R^5)$ group wherein $R^4$ and $R^5$ are as defined above;

(c9) an $N(R^4)CO_2(R^5)$ group wherein $R^4$ and $R^5$ are as defined above;
(c10) a $CO(R^4)$ group wherein $R^4$ is as defined above;
(c11) a $CO_2(R^4)$ group wherein $R^4$ is as defined above;
(c12) a $CON(R^4)(R^5)$ group wherein $R^4$ and $R^5$ are as defined above;
(c13) a $C(R^4)=NOR^5$ group wherein $R^4$ and $R^5$ are as defined above;
(c14) a $(C_1-C_8)$alkyl group;
(c15) a $(C_2-C_8)$alkenyl group;
(c16) a $(C_2-C_8)$alkynyl group;
(c17) a $(C_3-C_8)$cycloalkyl group;
(c18) a halo$(C_1-C_8)$alkyl group;
(c19) a halo$(C_2-C_8)$alkenyl group;
(c20) a halo$(C_2-C_8)$alkynyl group;
(c21) a halo$(C_3-C_8)$cycloalkyl group;
(c22) a tri$(C_1-C_8)$alkylsilyl group wherein the alkyl groups may be the same or different;
(c23) a tri$(C_1-C_8)$alkylsilyl$(C_1-C_8)$alkyl group wherein the alkyl groups of the tri$(C_1-C_8)$alkylsilyl may be the same or different;
(c24) a $(C_3-C_8)$cycloalkyl$(C_1-C_8)$alkyl group;
(c25) a halo$(C_3-C_8)$cycloalkyl$(C_1-C_8)$alkyl group;
(c26) a $(C_3-C_8)$cycloalkyl$(C_3-C_8)$cycloalkyl group;
(c27) a $(C_1-C_8)$alkoxy group;
(c28) a $(C_2-C_8)$alkenyloxy group;
(c29) a $(C_2-C_8)$alkynyloxy group;
(c30) a $(C_3-C_8)$cycloalkyloxy group (said cycloalkyl is optionally fused with a benzene ring);
(c31) a halo$(C_1-C_8)$alkoxy group;
(c32) a halo$(C_2-C_8)$alkenyloxy group;
(c33) a halo$(C_2-C_8)$alkynyloxy group;
(c34) a halo$(C_3-C_8)$cycloalkyloxy group (said cycloalkyl is optionally fused with a benzene ring);
(c35) a $(C_3-C_8)$cycloalkyl$(C_1-C_8)$alkoxy group;
(c36) a halo$(C_3-C_8)$cycloalkyl$(C_1-C_8)$alkoxy group;
(c37) a $(C_1-C_8)$alkoxy$(C_1-C_8)$alkyl group;
(c38) a halo$(C_1-C_8)$alkoxy$(C_1-C_8)$alkoxy group;
(c39) a $(C_1-C_8)$alkoxyhalo$(C_1-C_8)$alkoxy group;
(c40) a halo$(C_1-C_8)$alkoxyhalo$(C_1-C_8)$alkoxy group;
(c41) a mercapto group;
(c42) a $(C_1-C_8)$alkylthio group;
(c43) a $(C_2-C_8)$alkenylthio group;
(c44) a $(C_2-C_8)$alkynylthio group;
(c45) a $(C_3-C_8)$cycloalkylthio group;
(c46) a halo$(C_1-C_8)$alkylthio group;
(c47) a halo$(C_2-C_8)$alkenylthio group;
(c48) a halo$(C_2-C_8)$alkynylthio group;
(c49) a halo$(C_3-C_8)$cycloalkylthio group;
(c50) a $(C_3-C_8)$cycloalkyl$(C_1-C_8)$alkylthio group;
(c51) a halo$(C_3-C_8)$cycloalkyl$(C_1-C_8)$alkylthio group;
(c52) a $(C_1-C_8)$alkoxy$(C_1-C_8)$alkylthio group;
(c53) a halo$(C_1-C_8)$alkoxy$(C_1-C_8)$alkylthio group;
(c54) a $(C_1-C_8)$alkoxyhalo$(C_1-C_8)$alkylthio group;
(c55) a halo$(C_1-C_8)$alkoxyhalo$(C_1-C_8)$alkylthio group;
(c56) a $(C_1-C_8)$alkylsulfinyl group;
(c57) a $(C_2-C_8)$alkenylsulfinyl group;
(c58) a $(C_2-C_8)$alkynylsulfinyl group;
(c59) a $(C_3-C_8)$cycloalkylsulfinyl group;
(c60) a halo$(C_1-C_8)$alkylsulfinyl group;
(c61) a halo$(C_2-C_8)$alkenylsulfinyl group;
(c62) a halo$(C_2-C_8)$alkynylsulfinyl group;
(c63) a halo$(C_3-C_8)$cycloalkylsulfinyl group;
(c64) a $(C_3-C_8)$cycloalkyl$(C_1-C_8)$alkylsulfinyl group;
(c65) a halo$(C_3-C_8)$cycloalkyl$(C_1-C_8)$alkylsulfinyl group;
(c66) a $(C_1-C_8)$alkylsulfonyl group;
(c67) a $(C_2-C_8)$alkenylsulfonyl group;
(c68) a $(C_2-C_8)$alkynylsulfonyl group;
(c69) a $(C_3-C_8)$cycloalkylsulfonyl group;
(c70) a halo$(C_1-C_8)$alkylsulfonyl group;
(c71) a halo$(C_2-C_8)$alkenylsulfonyl group;
(c72) a halo$(C_2-C_8)$alkynylsulfonyl group;
(c73) a halo$(C_3-C_8)$cycloalkylsulfonyl group;
(c74) a $(C_3-C_8)$cycloalkyl$(C_1-C_8)$alkylsulfonyl group;
(c75) a halo$(C_3-C_8)$cycloalkyl$(C_1-C_8)$alkylsulfonyl group;
(c76) an aryl group;
(c77) an aryl group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;
(c78) an aryl$(C_1-C_8)$alkyl group;
(c79) an aryl$(C_1-C_6)$alkyl group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo $(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4) R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;
(c80) an aryloxy group;
(c81) an aryloxy group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-$ $C_6$)alkoxy group, (o) a halo($C_3$-$C_6$)cycloalkyl($C_1$-$C_6$) alkoxy group, (p) a ($C_1$-$C_6$)alkylthio group, (q) a halo ($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$) alkylsulfonyl group, (u) a halo($C_1$-$C_6$)alkylsulfonyl group, (v) an N($R^4$) $R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)R$^5$ group wherein $R^4$ and $R^5$ are as defined above, and (cc) a C($R^4$)=NOR$^5$ group wherein $R^4$ and $R^5$ are as defined above;

(c82) an aryloxy($C_1$-$C_8$)alkyl group;

(c83) an aryloxy($C_1$-$C_6$)alkyl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$) alkynyloxy group, (l) a ($C_3$-$C_6$)cycloalkoxy group, (m) a halo($C_3$-$C_6$)cycloalkoxy group, (n) a ($C_3$-$C_6$)cycloalkyl ($C_1$-$C_6$)alkoxy group, (o) a halo($C_3$-$C_6$)cycloalkyl($C_1$-$C_6$) alkoxy group, (p) a ($C_1$-$C_6$)alkylthio group, (q) a halo ($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$) alkylsulfonyl group, (u) a halo($C_1$-$C_6$)alkylsulfonyl group, (v) an N($R^4$)R$^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)R$^5$ group wherein $R^4$ and $R^5$ are as defined above, and (cc) a C($R^4$)=NOR$^5$ group wherein $R^4$ and $R^5$ are as defined above;

(c84) an arylthio group;

(c85) an arylthio group having, on the ring, the same or different 1 to 5 substituents selected from (a) a halogen atom, (b) a cyano group, (c) a nitro group, (d) a ($C_1$-$C_6$) alkyl group, (e) a halo($C_1$-$C_6$)alkyl group, (f) a ($C_1$-$C_6$) alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$) alkoxy group, (p) a ($C_1$-$C_6$)alkylthio group, (q) a halo ($C_1$-$C_6$)alkylthio group, (r) a ($C_2$-$C_6$)alkylsulfinyl group, (s) a halo($C_2$-$C_6$)alkylsulfinyl group, (t) a ($C_1$-$C_6$) alkylsulfonyl group, (u) a halo($C_1$-$C_6$)alkylsulfonyl group, (v) an N($R^4$)R$^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)R$^5$ group wherein $R^4$ and $R^5$ are as defined above, and (cc) a C($R^4$)=NOR$^5$ group wherein $R^4$ and $R^5$ are as defined above;

(c86) a halo($C_1$-$C_8$)alkylenedioxy group;

(c87) a ($C_1$-$C_8$)alkoxy($C_1$-$C_8$)alkoxy group;

(c88) a ($C_3$-$C_8$)alkylene group;

(c89) a ($C_1$-$C_8$)alkyl($C_3$-$C_8$)alkylene group;

(c90) a tri($C_1$-$C_8$)alkylsilyloxy group wherein the alkyl groups may be the same or different;

(c91) a tri($C_1$-$C_8$)alkylsilyl($C_1$-$C_8$)alkoxy group wherein the alkyl groups may be the same or different;

(c92) a di($C_1$-$C_8$)alkylhalo($C_1$-$C_8$)alkylsilyl group wherein the alkyl groups may be the same or different;

(c93) a di($C_1$-$C_8$)alkyl($C_1$-$C_8$)alkylthio($C_1$-$C_8$)alkylsilyl group wherein the alkyl groups may be the same or different;

(c94) a di($C_1$-$C_8$)alkylhydroxysilyl group wherein the alkyl groups may be the same or different;

(c95) a di($C_1$-$C_8$)alkylhydrosilyl group wherein the alkyl groups may be the same or different;

(c96) a di($C_1$-$C_8$)alkylphenylsilyl group wherein the alkyl groups may be the same or different;

(c97) a ($C_1$-$C_8$)alkylthio($C_1$-$C_8$)alkoxy group;

(c98) a ($C_1$-$C_8$)alkylsulfinyl($C_1$-$C_8$)alkoxy group;

(c99) a ($C_1$-$C_8$)alkylsulfonyl($C_1$-$C_8$)alkoxy group;

(c100) a ($C_1$-$C_8$)alkoxycarbonyl($C_1$-$C_8$)alkoxy group;

(c101) a ($C_1$-$C_8$)alkylcarbonyl($C_1$-$C_8$)alkoxy group;

(c102) a cyano($C_1$-$C_8$)alkoxy group;

(c103) an aryl($C_1$-$C_8$)alkoxy group wherein the alkoxy moiety may be halogenated;

(c104) an aryl($C_1$-$C_8$)alkoxy group wherein the alkoxy moiety may be halogenated, which has, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$) alkynyloxy group, (l) a ($C_3$-$C_6$)cycloalkoxy group, (m) a halo($C_3$-$C_6$)cycloalkoxy group, (n) a ($C_3$-$C_6$)cycloalkyl ($C_1$-$C_6$)alkoxy group, (o) a halo($C_3$-$C_6$)cycloalkyl($C_1$-$C_6$) alkoxy group, (p) a ($C_1$-$C_6$)alkylthio group, (q) a halo ($C_1$-$C_6$)alkylthio group, (r) a ($C_2$-$C_6$)alkylsulfinyl group, (s) a halo($C_2$-$C_6$)alkylsulfinyl group, (t) a ($C_1$-$C_6$) alkylsulfonyl group, (u) a halo($C_1$-$C_6$)alkylsulfonyl group, (v) an N($R^4$)R$^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)R$^5$ group wherein $R^4$ and $R^5$ are as defined above, and (cc) a C($R^4$)=NOR$^5$ group wherein $R^4$ and $R^5$ are as defined above;

(c105) a hydroxy($C_1$-$C_8$)alkyl group;

(c106) a ($C_1$-$C_8$)alkylthio($C_1$-$C_8$)alkylcarbonyl group;

(c107) a ($C_1$-$C_8$)alkylthio($C_1$-$C_8$)alkyl group;

(c108) a tri($C_1$-$C_8$)alkylsilyl($C_1$-$C_8$)alkylthio group wherein the alkyl groups of the tri($C_1$-$C_8$)alkylsilyl may be the same or different;

(c109) a tri($C_1$-$C_8$)alkylsilyl($C_1$-$C_8$)alkylsulfinyl group wherein the alkyl groups of the tri($C_1$-$C_8$)alkylsilyl may be the same or different;

(c110) a tri($C_1$-$C_8$)alkylsilyl($C_1$-$C_8$)alkylsulfonyl group wherein the alkyl groups of the tri($C_1$-$C_8$)alkylsilyl may be the same or different;

(c111) a $R^4$($R^5$) N($C_1$-$C_8$)alkyl group wherein $R^4$ and $R^5$ are as defined above;

(c112) a heterocyclic group;

(c113) a heterocyclic group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c114) a heterocyclyloxy group;

(c115) a heterocyclyloxy group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c116) a heterocyclylthio group;

(c117) a heterocyclylthio group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c118) a heterocyclylsulfinyl group;

(c119) a heterocyclylsulfinyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c120) a heterocyclylsulfonyl group;

(c121) a heterocyclylsulfonyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c122) a heterocyclyl$(C_1-C_8)$alkyloxy group;

(c123) a heterocyclyl$(C_1-C_8)$alkyloxy group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$alkylsilyl$(C_2-C_6)$alkynyl group wherein the alkyl groups may be the same or different, and (w) an oxo group;

(c124) a $(C_1-C_8)$alkyl$(C_3-C_8)$cycloalkyl group;

(c125) a halo$(C_1-C_8)$alkyl$(C_3-C_8)$cycloalkyl group;

(c126) a $(C_1-C_8)$alkylsulfinyl$(C_1-C_8)$alkyl group;

(c127) a di$(C_1-C_8)$alkylbenzylsilyl group wherein the alkyl groups may be the same or different;

(c128) a heterocyclyl$(C_1-C_8)$alkyl group;

(c129) a heterocyclyl$(C_1-C_8)$alkyl group having, on the ring, the same or different 1 to 5 substituents selected from (a) a halogen atom, (b) a cyano group, (c) a nitro group, (d) a formyl group, (e) a $(C_1-C_6)$alkyl group, (f) a halo$(C_1-C_6)$alkyl group, (g) a $(C_1-C_6)$alkoxy group, (h) a halo$(C_1-C_6)$alkoxy group, (i) a $(C_3-C_6)$cycloalkyl$(C_1-C_6)$alkoxy group, (j) a $(C_1-C_6)$alkylthio group, (k) a halo$(C_1-C_6)$alkylthio group, (l) a $(C_1-C_6)$alkylsulfinyl group, (m) a halo$(C_1-C_6)$alkylsulfinyl group, (n) a $(C_1-C_6)$alkylsulfonyl group, (o) a halo$(C_1-C_6)$alkylsulfonyl group, (p) a $(C_1-C_6)$alkylcarbonyl group, (q) a carboxyl group, (r) a $(C_1-C_6)$alkoxycarbonyl group, (s) a $R^4(R^5)N$ carbonyl group wherein $R^4$ and $R^5$ are as defined above, (t) a $(C_2-C_6)$alkynyl group, (u) a tri$(C_1-C_6)$alkylsilyl$(C_1-C_6)$alkyl group wherein the alkyl groups of the tri$(C_1-C_6)$alkylsilyl may be the same or different, (v) a tri$(C_1-C_6)$ alkylsilyl($C_2$-$C_6$)alkynyl group wherein the alkyl groups may be the same or different, and (w) an oxo group, (c130) a heterocyclyloxy($C_1$-$C_8$)alkyl group; or (c131) a heterocyclyloxy($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, or X can form, together with the adjacent $R^2$ or $R^3$, (C132) a bicyclo ring, wherein the bicyclo ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group; or, X can form, together with the adjacent X on an aromatic ring, (C133) a bicyclo ring or (C134) a fused ring, wherein the bicyclo ring or fused ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group, Y is CH or a nitrogen atom, m is an integer of 0 to 5, and n is an integer of 0 or 1, or a salt thereof;

[2] the arylalkyloxypyrimidine derivative according to the above-mentioned [1], wherein Y, q, m, and n are as defined in the above-mentioned [1], $R^1$ is (a1) a halogen atom;
(a2) a formyl group;
(a3) a cyano group;
(a4) a ($C_1$-$C_8$)alkyl group;
(a5) a ($C_3$-$C_8$)cycloalkyl group;
(a6) a ($C_2$-$C_8$)alkenyl group;
(a7) a ($C_2$-$C_8$)alkynyl group;
(a8) a halo($C_1$-$C_8$)alkyl group;
(a11) a halo($C_2$-$C_8$)alkynyl group;
(a12) a ($C_1$-$C_8$)alkoxy($C_1$-$C_8$)alkyl group;
(a13) a ($C_3$-$C_8$)cycloalkyl($C_1$-$C_8$)alkyl group;
(a14) a ($C_1$-$C_8$)alkoxyhalo($C_1$-$C_8$)alkyl group;
(a16) a ($C_1$-$C_8$)alkylthio($C_1$-$C_8$)alkyl group;
(a17) a ($C_1$-$C_8$)alkylsulfinyl($C_1$-$C_8$)alkyl group;
(a18) a ($C_1$-$C_8$)alkylsulfonyl($C_1$-$C_8$)alkyl group;
(a27) a $R^4(R^5)$N($C_1$-$C_8$)alkyl group wherein $R^4$ and $R^5$ are as defined in the above-mentioned [1];
(a31) an aryl group;
(a32) an aryl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above and (t) a phenoxy group;
(a33) an aryl($C_1$-$C_8$)alkyl group;
(a37) an arylthio($C_1$-$C_8$)alkyl group;
(a39) an arylsulfinyl($C_1$-$C_8$)alkyl group;
(a41) an arylsulfonyl($C_1$-$C_8$)alkyl group;
(a43) a ($C_1$-$C_8$)alkylcarbonyl group;
(a45) a ($C_1$-$C_8$)alkoxycarbonyl group;
(a46) a $R^4(R^5)$N carbonyl group wherein $R^4$ and $R^5$ are as defined above;
(a47) a ($C_1$-$C_8$)alkoxy($C_1$-$C_8$)alkoxy($C_1$-$C_8$)alkyl group;
(a49) a heterocyclic group;
(a50) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a phenyl group, (u) an oxo group, and (v) a ($C_1$-$C_6$)alkoxycarbonyl ($C_1$-$C_6$)alkyl group;
(a51) a heterocyclyl($C_1$-$C_8$)alkyl group;
(a56) a $C(R^4)$=$NOR^5$ group wherein $R^4$ and $R^5$ are as defined above;
(a57) an oxiranyl group;
(a65) a hydroxy($C_1$-$C_8$)alkyl group;
(a66) an aryloxy($C_1$-$C_8$)alkyl group;
(a67) an aryloxy($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;
(a81) a (heterocyclyl)(($C_1$-$C_8$)alkoxy) ($C_1$-$C_8$)alkyl group;
(a83) a di($C_1$-$C_8$)alkoxy($C_1$-$C_8$)alkyl group wherein the alkoxy groups of the di($C_1$-$C_8$)alkoxy may be the same or different;
(a84) a di($C_1$-$C_8$)alkylthio($C_1$-$C_8$)alkyl group wherein the alkyl groups of the di($C_1$-$C_8$)alkylthio may be the same or different;
(a85) a tri($C_1$-$C_8$)alkylsilyloxy($C_1$-$C_8$)alkyl group wherein the alkyl groups of the tri($C_1$-$C_8$)alkylsilyl may be the same or different;
(a86) a carboxyl group;
(a87) an aryloxycarbonyl group;

(a88) a C($R^4$)=NOS$O_2$$R^5$ group wherein $R^4$ and $R^5$ are as defined above;
(a89) a heterocycylimino($C_1$-$C_8$)alkyl group;
(a90) a tri($C_1$-$C_8$)alkylsilyl($C_2$-$C_8$)alkynyl group wherein the alkyl groups of the tri($C_1$-$C_8$)alkylsilyl may be the same or different;
(a91) a ($C_1$-$C_8$)alkoxy($C_2$-$C_8$)alkynyl group;
(a92) a hydroxy($C_2$-$C_8$)alkynyl group;
(a93) a (hydroxy)(($C_1$-$C_8$)alkoxy($C_1$-$C_8$)alkoxy)($C_1$-$C_8$) alkyl group;
(a94) a dihydroxy($C_1$-$C_8$)alkyl group;
(a95) a (hydroxy)(($C_1$-$C_8$)alkoxy)($C_1$-$C_8$)alkyl group;
(a96) a di($C_1$-$C_8$)alkylsulfonyloxy($C_1$-$C_8$)alkyl group wherein the alkyl groups of the di($C_1$-$C_8$)alkylsulfonyloxy may be the same or different;
(a97) a di(($C_1$-$C_8$)alkoxy($C_1$-$C_8$)alkoxy)($C_1$-$C_8$)alkyl group wherein the alkoxy groups of the di(($C_1$-$C_8$)alkoxy($C_1$-$C_8$)alkoxy may be the same or different;
(a98) a di($C_1$-$C_8$)alkoxycarbonyl($C_2$-$C_8$)alkenyl group wherein the alkoxy groups of the di($C_1$-$C_8$)alkoxycarbonyl may be the same or different;
(a99) a ($C_1$-$C_8$)alkoxycarbonyl(cyano)($C_2$-$C_8$)alkenyl group;
(a100) a (($C_1$-$C_8$)alkoxy($C_1$-$C_8$)alkoxy) (hydroxy) ($C_1$-$C_8$) alkyl group;
(a101) a dicyano($C_2$-$C_8$)alkenyl group;
(a102) a ($C_3$-$C_8$)cycloalkylidene($C_1$-$C_8$)alkyl group;
(a103) a ($C_3$-$C_8$)cycloalkyl(hydroxy) ($C_1$-$C_8$)alkyl group;
(a104) a ($C_3$-$C_8$)cycloalkyl(($C_1$-$C_8$)alkoxy)($C_1$-$C_8$)alkyl group;
(a105) a heterocyclyl($C_2$-$C_8$)alkenyl group;
(a106) a heterocyclyl($C_2$-$C_8$)alkenyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$) alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, and (t) an oxo group;
(a107) a halo($C_1$-$C_8$)alkylcarbonyloxy($C_2$-$C_8$)alkenyl group;
(a108) a ($C_3$-$C_8$)cycloalkyl(halo($C_1$-$C_8$)alkylcarbonyloxy) ($C_1$-$C_8$)alkyl group;
(a109) a ($C_1$-$C_8$)alkoxycarbonyl(hydroxy)($C_1$-$C_8$)alkyl group;
(a110) a carboxy(hydroxy)($C_1$-$C_8$)alkyl group;
(a111) a di($C_1$-$C_8$)alkoxycarbonyl($C_3$-$C_6$)cycloalkyl group wherein the alkoxy groups of the di($C_1$-$C_8$)alkoxycarbonyl may be the same or different;
(a112) a di($C_1$-$C_8$)alkoxycarbonyl($C_1$-$C_8$)alkyl group wherein the alkoxy groups of the di($C_1$-$C_8$)alkoxycarbonyl may be the same or different;
(a113) a ($C_1$-$C_8$)alkylcarbonyl($C_2$-$C_8$)alkenyl group;
(a114) a hydroxyhalo($C_1$-$C_8$)alkyl group;
(a115) a dihydroxyhalo($C_1$-$C_8$)alkyl group;
(a116) a ($C_1$-$C_8$)alkoxycarbonyl($C_3$-$C_8$)cycloalkyl group;
(a117) a cyano($C_3$-$C_8$)cycloalkyl group;
(a118) a ($C_1$-$C_8$)alkoxycarbonyl($C_2$-$C_8$)alkenyl group;
(a119) a cyano($C_2$-$C_8$)alkenyl group;
(a120) a (($C_1$-$C_8$)alkoxy)(hydroxy)halo($C_1$-$C_8$)alkyl group;
(a121) a $R^4$($R^5$)N($C_1$-$C_8$)alkyl($R^5$)N carbonyl group wherein $R^4$ and $R^5$ are as defined above;
(a122) a $R^4$($R^5$)NCO($R^5$)N($C_1$-$C_8$)alkyl group wherein $R^4$ and $R^5$ are as defined above;
(a123) a tri($C_1$-$C_8$)alkylsilyl($C_2$-$C_8$)alkynyl($C_2$-$C_8$)alkenyl group wherein the alkyl groups of the tri($C_1$-$C_8$)alkylsilyl may be the same or different; or
(a124) a structural formula $Q^7$, $Q^8$, $Q^9$, $Q^{10}$, $Q^{11}$, $Q^{12}$, $Q^{13}$, $Q^{14}$, $Q^{15}$, $Q^{16}$, $Q^{17}$, $Q^{18}$, $Q^{19}$, $Q^{20}$, $Q^{21}$, $Q^{22}$, $Q^{23}$, $Q^{24}$, $Q^{25}$, $Q^{26}$, $Q^{27}$, $Q^{28}$, or $Q^{29}$ wherein each structural formula and the symbols therein are as defined in the above-mentioned [1], $R^2$ and $R^3$ may be the same or different and each is
(b1) a hydrogen atom; or
(b6) a halo($C_1$-$C_8$)alkyl group;
X may be the same or different and each is
(c1) a hydrogen atom;
(c2) a halogen atom;
(c4) a cyano group;
(c5) a nitro group;
(c10) a CO($R^4$) group wherein $R^4$ is as defined above;
(c14) a ($C_1$-$C_8$)alkyl group;
(c18) a halo($C_1$-$C_8$)alkyl group;
(c22) a tri($C_1$-$C_8$)alkylsilyl group wherein the alkyl groups may be the same or different;
(c27) a ($C_1$-$C_8$)alkoxy group;
(c31) a halo($C_1$-$C_8$)alkoxy group;
(c40) a halo($C_1$-$C_8$)alkoxyhalo($C_1$-$C_8$)alkoxy group;
(c42) a ($C_1$-$C_8$)alkylthio group;
(c46) a halo($C_1$-$C_8$)alkylthio group;
(c76) an aryl group;
(c77) an aryl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$) alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$) alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$) COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)R$^5$ group wherein $R^4$ and $R^5$ are as defined above, and (cc) a C($R^4$)=NOR$^5$ group wherein $R^4$ and $R^5$ are as defined above;
(c80) an aryloxy group; or
(c81) an aryloxy group having, on the ring, the same or different 1 to 5 substituents selected from (a) a halogen atom, (b) a cyano group, (c) a nitro group, (d) a ($C_1$-$C_6$) alkyl group, (e) a halo($C_1$-$C_6$)alkyl group, (f) a ($C_1$-$C_6$) alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo ($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$) alkoxy group, (p) a ($C_1$-$C_6$)alkylthio group, (q) a halo ($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above; or a salt thereof;

[3] an agrohorticultural insecticide comprising the arylalykloxypyrimidine derivative according to the above-mentioned [1] or [2] or a salt thereof as an active ingredient;

[4] a method of using an agrohorticultural insecticide, which comprises treating a plant or soil with the arylalkyloxypyrimidine derivative according to the above-mentioned [1] or [2] or a salt thereof;

[5] a method of controlling an agrohorticultural pest, which comprises treating a plant or soil with the arylalkyloxypyrimidine derivative according to the above-mentioned [1] or [2] or a salt thereof;

[6] use of the arulalkyloxypyrimidine derivative according to the above-mentioned [1] or [2] or a salt thereof as an agrohorticultural insecticide;

[7] use of the arulalkyloxypyrimidine derivative according to the above-mentioned [1] or [2] or a salt thereof as a veterinary insecticide;

[8] an arylalkyloxypyrimidine derivative represented by the formula (II):

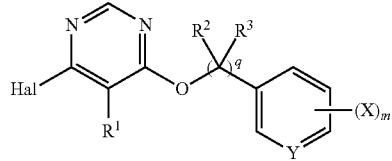

(II)

wherein $R^1$, $R^2$, $R^3$, X, Y, m and q are as defined in the above-mentioned [1], and
Hal is a halogen atom, or a salt thereof;
and the like.

Effect of the Invention

The arylalkyloxypyrimidine derivative of the present invention or a salt thereof has a superior effect as an agrohorticultural insecticide. On the other hand, the derivative shows an effect on pests being parasitic in pet animals such as dogs and cats, and domestic animals such as cattle, sheep and the like.

DESCRIPTION OF EMBODIMENTS

In the definition of the arylalkyloxypyrimidine derivative of the formula (I) of the present invention, the "halo" means a "halogen atom", and is a chlorine atom, a bromine atom, an iodine atom or a fluorine atom, "($C_1$-$C_8$)alkyl group" is, for example, a straight chain or branched chain alkyl group having 1 to 8 carbon atoms such as methyl group, ethyl group, normal propyl group, isopropyl group, normal butyl group, isobutyl group, secondary butyl group, tertiary butyl group, normal pentyl group, isopentyl group, tertiary pentyl group, neopentyl group, 2,3-dimethylpropyl group, 1-ethylpropyl group, 1-methylbutyl group, 2-methylbutyl group, normal hexyl group, isohexyl group, 2-hexyl group, 3-hexyl group, 2-methylpentyl group, 3-methylpentyl group, 1,1,2-trimethylpropyl group, 3,3-dimethylbutyl group, normal heptyl group, 2-heptyl group, 3-heptyl group, 2-methylhexyl group, 3-methylhexyl group, 4-methylhexyl group, isoheptyl group, normal octyl group and the like, "($C_2$-$C_8$)alkenyl group" is, for example, a straight chain or branched chain alkenyl group having 2 to 8 carbon atoms such as vinyl group, allyl group, isopropenyl group, 1-butenyl group, 2-butenyl group, 2-methyl-2-propenyl group, 1-methyl-2-propenyl group, 2-methyl-1-propenyl group, pentenyl group, 1-hexenyl group, 3,3-dimethyl-1-butenyl group, heptenyl group, octenyl group and the like, "($C_2$-$C_8$)alkynyl group" is, for example, a straight chain or branched chain alkynyl group having 2 to 8 carbon atoms such as ethynyl group, 1-propynyl group, 2-propynyl group, 1-butynyl group, 2-butynyl group, 3-butynyl group, 3-methyl-1-propynyl group, 2-methyl-3-propynyl group, pentynyl group, 1-hexynyl group, 3-methyl-1-butynyl group, 3,3-dimethyl-1-butynyl group, heptynyl group, octynyl group and the like.

The "($C_3$-$C_8$)cycloalkyl group" is, for example, a cyclic alkyl group having 3 to 8 carbon atoms such as cyclopropyl group, cyclobutyl group, cyclopentyl group, cyclohexyl group, cycloheptyl group, cyclooctyl group and the like, The "($C_3$-$C_8$)cycloalkylidene group" is, for example, a cyclic alkylidene group having 3 to 8 carbon atoms such as cyclopropylidene group, cyclobutylidene group, cyclopentylidene group, cyclohexylidene group, cycloheptylidene group, cyclooctylidene group and the like, "($C_1$-$C_8$)alkoxy group" is, for example, a straight chain or branched chain alkoxy group having 1 to 8 carbon atoms such as methoxy group, ethoxy group, normal propoxy group, isopropoxy group, normal butoxy group, secondary butoxy group, tertiary butoxy group, normal pentyloxy group, isopentyloxy group, tertiary pentyloxy group, neopentyloxy group, 2,3-dimethylpropyloxy group, 1-ethylpropyloxy group, 1-methylbutyloxy group, normal hexyloxy group, isohexyloxy group, 1,1,2-trimethylpropyloxy group, normal heptyloxy group, normal octyloxy group and the like, "($C_2$-$C_8$)alkenyloxy group" is, for example, a straight chain or branched chain alkenyloxy group having 2 to 8 carbon atoms such as propenyloxy group, butenyloxy group, pentenyloxy group, hexenyloxy group, heptenyloxy group, octenyloxy group and the like, "($C_2$-$C_8$)alkynyloxy group" is, for example, a straight chain or branched chain alkynyloxy group having 2 to 8 carbon atoms such as propynyloxy group, butynyloxy group, pentynyloxy group, hexynyloxy group, heptynyloxy group, octynyloxy group and the like.

Examples of the "($C_1$-$C_8$)alkylthio group" include a straight chain or branched chain alkylthio group having 1 to 8 carbon atoms such as methylthio group, ethylthio group, normal propylthio group, isopropylthio group, normal butylthio group, secondary butylthio group, tertiary butylthio group, normal pentylthio group, isopentylthio group, tertiary pentylthio group, neopentylthio group, 2,3-dimethylpropylthio group, 1-ethylpropylthio group, 1-methylbutylthio group, normal hexylthio group, isohexylthio group, 1,1,2-trimethylpropylthio group, normal heptylthio group, normal octylthio group and the like, examples of the "($C_1$-$C_8$)alkylsulfinyl group" include a straight chain or branched chain alkylsulfinyl group having 1 to 8 carbon atoms such as methylsulfinyl group, ethylsulfinyl group, normal propylsulfinyl group, isopropylsulfinyl group, normal butylsulfinyl group, secondary butylsulfinyl group, tertiary butylsulfinyl group, normal pentylsulfinyl group, isopentylsulfinyl group, tertiary pentylsulfinyl group, neopentylsulfinyl group, 2,3-dimethylpropylsulfinyl group, 1-ethylpropylsulfinyl group, 1-methylbutylsulfinyl group, normal hexylsulfinyl group, isohexylsulfinyl group, 1,1,2-trimethylpropylsulfinyl group, normal heptylsulfinyl group, normal octylsulfinyl group and the like, examples of the "$(C_1-C_8)$alkylsulfonyl group" include a straight chain or branched chain alkylsulfonyl group having 1 to 8 carbon atoms such as methylsulfonyl group, ethylsulfonyl group, normal propylsulfonyl group, isopropylsulfonyl group, normal butylsulfonyl group, secondary butylsulfonyl group, tertiary butylsulfonyl group, normal pentylsulfonyl group, isopentylsulfonyl group, tertiary pentylsulfonyl group, neopentylsulfonyl group, 2,3-dimethylpropylsulfonyl group, 1-ethylpropylsulfonyl group, 1-methylbutylsulfonyl group, normal hexylsulfonyl group, isohexylsulfonyl group, 1,1,2-trimethylpropylsulfonyl group, normal heptylsulfonyl group, normal octylsulfonyl group and the like.

Examples of the "$(C_2-C_8)$alkenylthio group" include a straight chain or branched chain alkenylthio group having 2 to 8 carbon atoms such as propenylthio group, butenylthio group, pentenylthio group, hexenylthio group, heptenylthio group, octenylthio group and the like, examples of the "$(C_2-C_8)$alkynylthio group" include a straight chain or branched chain alkynylthio group having 2 to 8 carbon atoms such as propynylthio group, butynylthio group, pentynylthio group, hexynylthio group, heptynylthio group, octynylthio group and the like.

Examples of the "$(C_2-C_8)$alkenylsulfinyl group" include a straight chain or branched chain alkenylsulfinyl group having 1 to 8 carbon atoms such as propenylsulfinyl group, butenylsulfinyl group, pentenylsulfinyl group, hexenylsulfinyl group, heptenylsulfinyl group, octenylsulfinyl group and the like, examples of the "$(C_2-C_8)$alkynylsulfinyl group" include a straight chain or branched chain alkynylsulfinyl group having 2 to 8 carbon atoms such as propynylsulfinyl group, butynylsulfinyl group, pentynylsulfinyl group, hexynylsulfinyl group, heptynylsulfinyl group, octynylsulfinyl group and the like.

Examples of the "$(C_2-C_8)$alkenylsulfonyl group" include a straight chain or branched chain alkenylsulfonyl group having 2 to 8 carbon atoms such as propenylsulfonyl group, butenylsulfonyl group, pentenylsulfonyl group, hexenylsulfonyl group, heptenylsulfonyl group, octenylsulfonyl group and the like, examples of the "$(C_2-C_8)$alkynylsulfonyl group" include a straight chain or branched chain alkynylsulfonyl group having 2 to 8 carbon atoms such as propynylsulfonyl group, butynylsulfonyl group, pentynylsulfonyl group, hexynylsulfonyl group, heptynylsulfonyl group, octynylsulfonyl group and the like.

The "$(C_3-C_8)$cycloalkyloxy group" is, for example, a cyclic alkyloxy group having 3 to 8 carbon atoms such as cyclopropoxy group, cyclobutoxy group, cyclopentyloxy group, cyclohexyloxy group, cycloheptyloxy group, cyclooctyloxy group and the like, "$(C_3-C_8)$cycloalkylthio group" is, for example, a cyclic alkylthio group having 3 to 8 carbon atoms such as cyclopropylthio group, cyclobutylthio group, cyclopentylthio group, cyclohexylthio group, cycloheptylthio group, cyclooctylthio group and the like, "$(C_3-C_8)$cycloalkylsulfinyl group" is, for example, a cyclic alkylsulfinyl group having 3 to 8 carbon atoms such as cyclopropylsulfinyl group, cyclobutylsulfinyl group, cyclopentylsulfinyl group, cyclohexylsulfinyl group, cycloheptylsulfinyl group, cyclooctylsulfinyl group and the like, "$(C_3-C_8)$cycloalkylsulfonyl group" is, for example, a cyclic alkylsulfonyl group having 3 to 8 carbon atoms such as cyclopropylsulfonyl group, cyclobutylsulfonyl group, cyclopentylsulfonyl group, cyclohexylsulfonyl group, cycloheptylsulfonyl group, cyclooctylsulfonyl group and the like.

The above-mentioned "$(C_1-C_8)$alkyl group", "$(C_2-C_8)$alkenyl group", "$(C_2-C_8)$alkynyl group", "$(C_3-C_8)$cycloalkyl group", "$(C_3-C_8)$cycloalkyloxy group", "$(C_1-C_8)$alkoxy group", "$(C_2-C_8)$alkenyloxy group", "$(C_2-C_8)$alkynyloxy group", "$(C_1-C_8)$alkylthio group", "$(C_1-C_8)$alkylsulfinyl group", "$(C_1-C_8)$alkylsulfonyl group", "$(C_2-C_8)$alkenylthio group", "$(C_2-C_8)$alkynylthio group", "$(C_2-C_8)$alkenylsulfinyl group", "$(C_2-C_8)$alkynylsulfinyl group", "$(C_2-C_8)$alkenylsulfonyl group", "$(C_2-C_8)$alkynylsulfonyl group", "$(C_3-C_8)$cycloalkyl group", "$(C_1-C_8)$alkoxy group", "$(C_2-C_8)$alkenyloxy group", "$(C_2-C_8)$alkynyloxy group", "$(C_3-C_8)$cycloalkylthio group", "$(C_3-C_8)$cycloalkylsulfinyl group" and "$(C_3-C_8)$cycloalkylsulfonyl group" may be substituted by one or more halogen atoms at substitutable position(s) and, when substituted by two or more halogen atoms, the halogen atoms may be the same or different.

They are indicates as "halo$(C_1-C_8)$alkyl group", "halo$(C_2-C_8)$alkenyl group", "halo$(C_2-C_8)$alkynyl group", "halo$(C_3-C_8)$cycloalkyl group", "halo$(C_3-C_8)$cycloalkyloxy group", "halo$(C_1-C_8)$alkoxy group", "halo$(C_2-C_8)$alkenyloxy group", "halo$(C_2-C_8)$alkynyloxy group", "halo$(C_1-C_8)$alkylthio group", "halo$(C_1-C_8)$alkylsulfinyl group", "halo$(C_1-C_8)$alkylsulfonyl group", "halo$(C_2-C_8)$alkenylthio group", "halo$(C_2-C_8)$alkynylthio group", "halo$(C_2-C_8)$alkenylsulfinyl group", "halo$(C_2-C_8)$alkynylsulfinyl group", "halo$(C_2-C_8)$alkenylsulfonyl group", "halo$(C_2-C_8)$alkynylsulfonyl group", "halo$(C_3-C_8)$cycloalkyl group", "halo$(C_1-C_8)$alkoxy group", "halo$(C_2-C_8)$alkenyloxy group", "halo$(C_2-C_8)$alkynyloxy group", "halo$(C_3-C_8)$cycloalkylthio group", "halo$(C_3-C_8)$cycloalkylsulfinyl group" and "halo$(C_3-C_8)$cycloalkylsulfonyl group", respectively.

The "tri$(C_1-C_8)$alkylsilyl group" is, for example, a straight chain or branched chain trialkylsilyl group having 1 to 8 carbon atoms such as trimethylsilyl group, triethylsilyl group, tertiary butyldimethylsilyl group, ethyldimethylsilyl group, isopropyldimethylsilyl group, n-propyldimethylsilyl group and the like. In this case, the three alkyl groups may be the same or different.

Examples of the di$(C_1-C_8)$alkylhalo$(C_1-C_8)$alkylsilyl group include a chloromethyldimethylsilyl group and the like. In this case, the two alkyl groups may be the same or different.

Examples of the di$(C_1-C_8)$alkyl$(C_1-C_8)$alkylthio$(C_1-C_8)$alkylsilyl group include a methylthiomethyldimethylsilyl group and the like. In this case, the two alkyl groups may be the same or different.

Examples of the di$(C_1-C_8)$alkylhydrosilyl group include a diisopropylsilyl group, a dimethylsilyl group and the like. In this case, the two alkyl groups may be the same or different.

Examples of the di$(C_1-C_8)$alkylhydroxysilyl group include a dimethylhydroxysilyl group and the like. In this case, the two alkyl groups may be the same or different.

Examples of the di$(C_1-C_8)$alkylphenylsilyl group include a dimethyl(phenyl)silyl group and the like. In this case, the two alkyl groups may be the same or different.

Examples of the di($C_1$-$C_8$)alkylbenzylsilyl group include a dimethyl(benzyl)silyl group and the like. In this case, the two alkyl groups may be the same or different.

Examples of the "aryl group" include an aromatic hydrocarbon group having a carbon number of 6 to 10 such as a phenyl group, a 1-naphthyl group, a 2-naphthyl group and the like.

The expressions of "($C_1$-$C_8$)", "($C_2$-$C_8$)", "($C_3$-$C_8$)" and the like show ranges of the carbon atom numbers of various substituents. Furthermore, the above-mentioned definition applies to the groups wherein the above-mentioned substituents are bonded to each other. For example, "($C_1$-$C_8$)alkoxy ($C_1$-$C_8$)alkyl group" means that a straight chain or branched chain alkoxy group having a carbon number of 1 to 8 is bonded to a straight chain or branched chain alkyl group having a carbon number of 1 to 8.

In addition, for example, "(($C_1$-$C_8$)alkoxy)(($C_3$-$C_8$)cycloalkyl)($C_1$-$C_8$)alkyl group" means that a straight chain or branched chain alkoxy group having 1 to 8 carbon atoms and a cyclic alkyl group having 3 to 8 carbon atoms are bonded to a straight chain or branched chain alkyl group having 1 to 8 carbon atoms.

When two or more substituents are bonded, each substituent may be bonded to the same carbon atom, or different carbon atoms. For example, in the "(($C_1$-$C_8$)alkoxy)(($C_3$-$C_8$)cycloalkyl)($C_1$-$C_8$)alkyl group", the ($C_1$-$C_8$)alkoxy group and ($C_3$-$C_8$)cycloalkyl group may be bonded to the same carbon atom or different carbon atom of ($C_1$-$C_8$)alkyl group.

The "($C_3$-$C_8$)alkylene group", "($C_1$-$C_8$)alkyl($C_3$-$C_8$)alkylene group" and "halo($C_1$-$C_8$)alkylenedioxy group" are groups that can be formed together with the two adjacent X groups, and examples of the "($C_3$-$C_8$)alkylene group" and "($C_1$-$C_8$)alkyl($C_3$-$C_8$)alkylene group" include a propylene group, a butylene group, a pentylene group, a hexylene group, a 1,1,4,4-tetramethylbutylene group and the like, and examples of the "halo($C_1$-$C_8$)alkylenedioxy group" include a difluoromethylenedioxy group, a tetrafluoroethylenedioxy group and the like.

Examples of the fused ring and bicyclo ring formed by adjacent two Xs or the bicyclo ring formed by X together with the adjacent $R^2$ or $R^3$ include fused rings such as tetrahydronaphthalene, naphthalene, benzodioxole, benzodioxane, indane, indole, benzofuran, benzothiophene, benzimidazole, benzothiazole, benzoxazole and the like, and bicyclo rings such as tetrahydronaphthalene, naphthalene, 1,2,3,4-tetrahydro-1,4-methanonaphthalene, 1,2,3,4-tetrahydro-1,4-ethanonaphthalene and the like.

Examples of the "heterocyclic group" and "heterocyclyl" include a 5- or 6-membered monocyclic aromatic heterocyclic group or 3- to 6-membered monocyclic nonaromatic heterocyclic group each of which contains, as a ring-constituting atom besides carbon atom, 1 to 4 hetero atoms selected from an oxygen atom, a sulfur atom and a nitrogen atom, a fused heterocyclic group obtained by condensation of the monocyclic aromatic or nonaromatic heterocycle with a benzene ring, and a fused heterocyclic group obtained by condensation of the monocyclic aromatic or nonaromatic heterocycles (heterocycles may be different).

Examples of the "aromatic heterocyclic group" include monocyclic aromatic heterocyclic groups such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl and the like; aromatic fused heterocyclic groups such as quinolyl, isoquinolyl, quinazolyl, quinoxalyl, benzofuranyl, benzothienyl, benzoxazolyl, benzoisoxazolyl, benzothiazolyl, benzimidazolyl, benzotriazolyl, indolyl, indazolyl, pyrrolopyrazinyl, imidazopyridinyl, imidazopyrazinyl, pyrazolopyridinyl, pyrazolothienyl, pyrazolotriazinyl and the like.

Examples of the "nonaromatic heterocyclic group" include monocyclic nonaromatic heterocyclic groups such as oxiranyl, thiiranyl, aziridinyl, oxetanyl, thietanyl, azetidinyl, pyrrolidinyl, 2-oxopyrrolidin-1-yl, piperidinyl, morpholinyl, thiomorpholinyl, piperazinyl, hexamethyleniminyl, oxazolidinyl, thiazolidinyl, imidazolidinyl, oxazolinyl, thiazolinyl, isoxazolinyl, imidazolinyl, dioxolyl, dioxolanyl, dihydrooxadiazolyl, 2-oxo-1,3-oxazolidin-5-yl, 5-oxo-1,2,4-oxadiazolin-3-yl, 1,3-dioxolan-2-yl, 1,3-dioxan-2-yl, 1,3-dioxepan-2-yl, pyranyl, tetrahydropyranyl, thiopyranyl, tetrahydrothiopyranyl, 1-oxide tetrahydrothiopyranyl, 1,1-dioxide tetrahydrothiopyranyl, tetrahydrofuranyl, dioxanyl, pyrazolidinyl, pyrazolinyl, tetrahydropyrimidinyl, dihydrotriazolyl, tetrahydrotriazolyl and the like; nonaromatic fused heterocyclic groups such as dihydroindolyl, dihydroisoindolyl, dihydrobenzofuranyl, dihydrobenzodioxinyl, dihydrobenzodioxepinyl, tetrahydrobenzofuranyl, chromenyl, dihydroquinolinyl, tetrahydroquinolinyl, dihydroisoquinolinyl, tetrahydroisoquinolinyl, dihydrophthalazinyl and the like; and the like.

Examples of the salts of the arylalkyloxypyrimidine derivative represented by the formula (I) of the present invention include inorganic acid salts such as hydrochloride, sulfate, nitrate, phosphate and the like, organic acid salts such as acetate, fumarate, maleate, oxalate, methanesulfonate, benzenesulfonate, paratoluenesulfonate and the like, and salts with inorganic or organic bases such as sodium ion, potassium ion, calcium ion, trimethylammonium and the like.

The arylalkyloxypyrimidine derivative represented by the formula (I) and a salt thereof of the present invention may contain one or plural number of asymmetric centers in the structural formula, and in some cases, two or more optical isomers and diastereomers may be present. The present invention encompasses any of such optical isomers and mixtures containing them at any ratio. In addition, the arylalkyloxypyrimidine derivative represented by the formula (I) and a salt thereof of the present invention may have two types of geometric isomers derived from a C—C double bond in the structural formula. The present invention encompasses all of geometric isomers and the mixtures containing them at any ratio.

Preferable embodiments of the arylalkyloxypyrimidine derivative of the formula (I) of the present invention are as follows.

$R^1$ is preferably
(a1) a halogen atom;
(a2) a formyl group;
(a3) a cyano group;
(a4) a ($C_1$-$C_8$)alkyl group;
(a5) a ($C_3$-$C_8$)cycloalkyl group;
(a6) a ($C_2$-$C_8$)alkenyl group;
(a7) a ($C_2$-$C_8$)alkynyl group;
(a8) a halo($C_1$-$C_8$)alkyl group;
(a11) a halo($C_2$-$C_8$)alkynyl group;
(a12) a ($C_1$-$C_8$)alkoxy($C_1$-$C_8$)alkyl group;
(a13) a ($C_3$-$C_8$)cycloalkyl($C_1$-$C_8$)alkyl group;
(a14) a ($C_1$-$C_8$)alkoxyhalo($C_1$-$C_8$)alkyl group;
(a16) a ($C_1$-$C_8$)alkylthio($C_1$-$C_8$)alkyl group;
(a17) a ($C_1$-$C_8$)alkylsulfinyl($C_1$-$C_8$)alkyl group;
(a18) a ($C_1$-$C_8$)alkylsulfonyl($C_1$-$C_8$)alkyl group;
(a27) a $R^4(R^5)$N($C_1$-$C_8$)alkyl group wherein $R^4$ and $R^5$ are as defined above;

(a31) an aryl group;
(a32) an aryl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above and (t) a phenoxy group;
(a33) an aryl($C_1$-$C_8$)alkyl group;
(a37) an arylthio($C_1$-$C_8$)alkyl group;
(a39) an arylsulfinyl($C_1$-$C_8$)alkyl group;
(a41) an arylsulfonyl($C_1$-$C_8$)alkyl group;
(a43) a ($C_1$-$C_8$)alkylcarbonyl group;
(a45) a ($C_1$-$C_8$)alkoxycarbonyl group;
(a46) a $R^4(R^5)$N carbonyl group wherein $R^4$ and $R^5$ are as defined above;
(a47) a ($C_1$-$C_8$)alkoxy($C_1$-$C_8$)alkoxy($C_1$-$C_8$)alkyl group;
(a49) a heterocyclic group;
(a50) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a phenyl group, (u) an oxo group, and (v) a ($C_1$-$C_6$)alkoxycarbonyl($C_1$-$C_6$)alkyl group;
(a51) a heterocyclyl($C_1$-$C_8$)alkyl group;
(a56) a $C(R^4)$=$NOR^5$ group wherein $R^4$ and $R^5$ are as defined above;
(a57) an oxiranyl group;
(a65) a hydroxy($C_1$-$C_8$)alkyl group;
(a66) an aryloxy($C_1$-$C_8$)alkyl group;
(a67) an aryloxy($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, and (s) a $R^4(R^5)$N carbonyl group wherein $R^4$ and $R^5$ are as defined above;
(a81) a (heterocyclyl)(($C_1$-$C_8$)alkoxy)($C_1$-$C_8$)alkyl group;
(a83) a di($C_1$-$C_8$)alkoxy($C_1$-$C_8$)alkyl group wherein the alkoxy groups of the di($C_1$-$C_8$)alkoxy may be the same or different;
(a84) a di($C_1$-$C_8$)alkylthio($C_1$-$C_8$)alkyl group wherein the alkyl groups of the di($C_1$-$C_8$)alkylthio may be the same or different;
(a85) a tri($C_1$-$C_8$)alkylsilyloxy($C_1$-$C_8$)alkyl group wherein the alkyl groups of the tri($C_1$-$C_8$)alkylsilyl may be the same or different;
(a86) a carboxyl group;
(a87) an aryloxycarbonyl group;
(a88) a $C(R^4)$=$NOSO_2R^5$ group wherein $R^4$ and $R^5$ are as defined above;
(a89) a heterocycylimino($C_1$-$C_8$)alkyl group;
(a90) a tri($C_1$-$C_8$)alkylsilyl($C_2$-$C_8$)alkynyl group wherein the alkyl groups of the tri($C_1$-$C_8$)alkylsilyl may be the same or different;
(a91) a ($C_1$-$C_8$)alkoxy($C_2$-$C_8$)alkynyl group;
(a92) a hydroxy($C_2$-$C_8$)alkynyl group;
(a93) a (hydroxy)(($C_1$-$C_8$)alkoxy($C_1$-$C_8$)alkoxy)($C_1$-$C_8$)alkyl group;
(a94) a dihydroxy($C_1$-$C_8$)alkyl group;
(a95) a (hydroxy)(($C_1$-$C_8$)alkoxy)($C_1$-$C_8$)alkyl group;
(a96) a di($C_1$-$C_8$)alkylsulfonyloxy($C_1$-$C_8$)alkyl group wherein the alkyl groups of the di($C_1$-$C_8$)alkylsulfonyloxy may be the same or different;
(a97) a di(($C_1$-$C_8$)alkoxy($C_1$-$C_8$)alkoxy)($C_1$-$C_8$)alkyl group wherein the alkoxy groups of the di(($C_1$-$C_8$)alkoxy($C_1$-$C_8$)alkoxy may be the same or different;
(a98) a di($C_1$-$C_8$)alkoxycarbonyl($C_2$-$C_8$)alkenyl group wherein the alkoxy groups of the di($C_1$-$C_8$)alkoxycarbonyl may be the same or different;
(a99) a ($C_1$-$C_8$)alkoxycarbonyl(cyano)($C_2$-$C_8$)alkenyl group;
(a100) a (($C_1$-$C_8$)alkoxy($C_1$-$C_8$)alkoxy)(hydroxy)($C_1$-$C_8$)alkyl group;
(a101) a dicyano($C_2$-$C_8$)alkenyl group;
(a102) a ($C_3$-$C_8$)cycloalkylidene($C_1$-$C_8$)alkyl group;
(a103) a ($C_3$-$C_8$)cycloalkyl(hydroxy)($C_1$-$C_8$)alkyl group;
(a104) a ($C_3$-$C_8$)cycloalkyl(($C_1$-$C_8$)alkoxy)($C_1$-$C_8$)alkyl group;
(a105) a heterocyclyl($C_2$-$C_8$)alkenyl group;
(a106) a heterocyclyl($C_2$-$C_8$)alkenyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, and (t) an oxo group;
(a107) a halo($C_1$-$C_8$)alkylcarbonyloxy($C_2$-$C_8$)alkenyl group;
(a108) a ($C_3$-$C_8$)cycloalkyl(halo($C_1$-$C_8$)alkylcarbonyloxy)($C_1$-$C_8$)alkyl group;
(a109) a ($C_1$-$C_8$)alkoxycarbonyl(hydroxy)($C_1$-$C_8$)alkyl group;
(a110) a carboxy(hydroxy)($C_1$-$C_8$)alkyl group;
(a111) a di($C_1$-$C_8$)alkoxycarbonyl($C_3$-$C_8$)cycloalkyl group wherein the alkoxy groups of the di($C_1$-$C_8$)alkoxycarbonyl may be the same or different;
(a112) a di($C_1$-$C_8$)alkoxycarbonyl($C_1$-$C_8$)alkyl group wherein the alkoxy groups of the di($C_1$-$C_8$)alkoxycarbonyl may be the same or different;
(a113) a ($C_1$-$C_8$)alkylcarbonyl($C_2$-$C_8$)alkenyl group;
(a114) a hydroxyhalo($C_1$-$C_8$)alkyl group;
(a115) a dihydroxyhalo($C_1$-$C_8$)alkyl group;
(a116) a ($C_1$-$C_8$)alkoxycarbonyl($C_3$-$C_8$)cycloalkyl group;

(a117) a cyano($C_3$-$C_8$)cycloalkyl group;
(a118) a ($C_1$-$C_8$)alkoxycarbonyl($C_2$-$C_8$)alkenyl group;
(a119) a cyano($C_2$-$C_8$)alkenyl group;
(a120) a (($C_1$-$C_8$)alkoxy)(hydroxy)halo($C_1$-$C_8$)alkyl group;
(a121) a $R^4(R^5)N(C_1$-$C_8)$alkyl$(R^5)N$ carbonyl group wherein $R^4$ and $R^5$ are as defined above;
(a122) a $R^4(R^5)NCO(R^5)N(C_1$-$C_8)$alkyl group wherein $R^4$ and $R^5$ are as defined above;
(a123) a tri($C_1$-$C_8$)alkylsilyl($C_2$-$C_8$)alkynyl($C_2$-$C_8$)alkenyl group wherein the alkyl groups of the tri($C_1$-$C_8$)alkylsilyl may be the same or different; or
(a124) a structural formula $Q^7$, $Q^8$, $Q^9$, $Q^{10}$, $Q^{11}$, $Q^{12}$, $Q^{13}$, $Q^{14}$, $Q^{15}$, $Q^{16}$, $Q^{17}$, $Q^{18}$, $Q^{19}$, $Q^{20}$, $Q^{21}$, $Q^{22}$, $Q^{23}$, $Q^{24}$, $Q^{25}$, $Q^{26}$, $Q^{27}$, $Q^{28}$, or $Q^{29}$ wherein each structural formula and the symbols therein are as defined above.

$R^2$ and $R^3$ may be the same or different and each is preferably
(b1) a hydrogen atom; or
(b6) a halo($C_1$-$C_8$)alkyl group.

Each X may be the same or different and is preferably
(c1) a hydrogen atom;
(c2) a halogen atom;
(c4) a cyano group;
(c5) a nitro group;
(c10) a $CO(R^4)$ group wherein $R^4$ is as defined above;
(c14) a ($C_1$-$C_8$)alkyl group;
(c18) a halo($C_1$-$C_8$)alkyl group;
(c22) a tri($C_1$-$C_8$)alkylsilyl group wherein the alkyl groups may be the same or different;
(c27) a ($C_1$-$C_8$)alkoxy group;
(c31) a halo($C_1$-$C_8$)alkoxy group;
(c40) a halo($C_1$-$C_8$)alkoxyhalo($C_1$-$C_8$)alkoxy group;
(c42) a ($C_1$-$C_8$)alkylthio group;
(c46) a halo($C_1$-$C_8$)alkylthio group;
(c76) an aryl group;
(c77) an aryl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)$=$NOR^5$ group wherein $R^4$ and $R^5$ are as defined above;

(c80) an aryloxy group; or
(c81) an aryloxy group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)$=$NOR^5$ group wherein $R^4$ and $R^5$ are as defined above.

As Y, CH is preferable.
As q, 1 is preferable.
As m, 1 or 2 is preferable.
As n, 0 is preferable.

Various derivatives of the present invention can be produced by, for example, the following production methods, and the present invention is not limited thereto.

Production Method

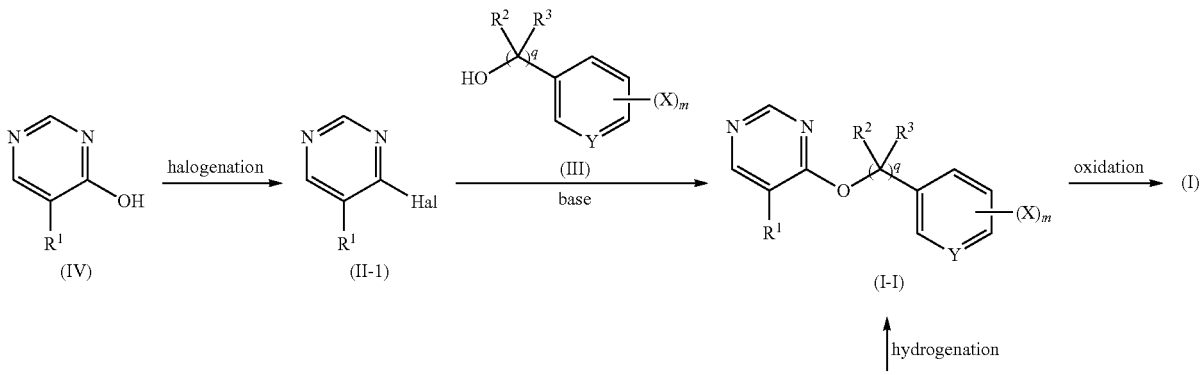

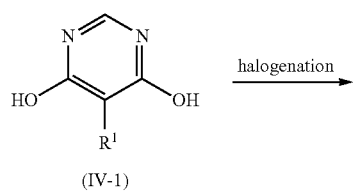 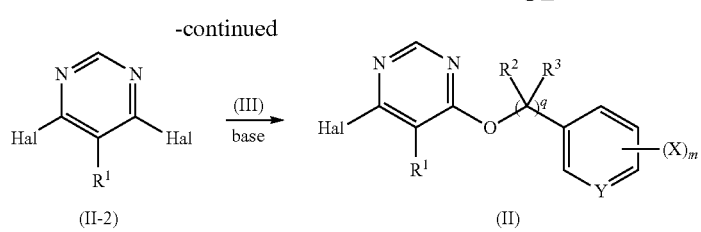

wherein $R^1$, $R^2$, $R^3$, X, q and m are as defined above, and Hal is a halogen atom.

Production Methods of the Formula (II-1) from the Formula (IV) and the Formula (II-2) from the Formula (IV-1)

The derivatives of the formula (IV) and the formula (IV-1) to be the starting materials can be produced by the methods disclosed in Organic Process Research and Development, 1, 300 (1997), J. Amer. Chem. Soc., 77, 745 (1955), WO2001-017975 and the like.

The halogenopyrimidine derivatives represented by the formulas (II-1) and (II-2) can be produced by reacting 4-hydroxypyrimidine derivative (IV) or 4,6-dihydroxypyrimidine derivative (IV-1) produced by the methods described in the above-mentioned documents with 1 to 10 equivalents of a halogenating agent in an inert solvent. Examples of the halogenating agent include thionyl chloride, phosphorus oxychloride, phosphorus pentachloride, phosphorus(III) bromide and the like. The inert solvent may be any as long as it does not markedly inhibit the progress of this reaction and, for example, aliphatic hydrocarbons such as hexane, cyclohexane, methylcyclohexane and the like, halogenated hydrocarbons such as chloroform, dichloromethane, carbon tetrachloride and the like, aromatic hydrocarbons such as benzene, xylene, toluene and the like, chain or cyclic ethers such as diethyl ether, t-butyl methyl ether, dioxane, tetrahydrofuran, 1,2-dimethoxyethane and the like, nitriles such as acetonitrile, propionitrile and the like, chain or cyclic ketones such as acetone, methyl isobutyl ketone, cyclohexanone and the like, esters such as ethyl acetate, butyl acetate and the like, and the like can be mentioned. These inert solvents can be used alone or a mixture of two or more kinds thereof may be used. The reaction temperature can be appropriately selected from 0° C. to the refluxing temperature of the inert solvent or halogenating agent to be used. While the reaction time varies depending on the scale of reaction, reaction temperature and the like and is not constant, it can be appropriately selected from several minutes to 100 hours. While the reaction also proceeds in the presence of oxygen and the like in the air, it may be performed in an inert gas atmosphere such as nitrogen gas, argon gas and the like. After completion of the reaction, the object product is isolated from the reaction system containing the object product by a conventional method and purified as necessary by a recrystallization method, a distillation method, a column chromatography method and the like to give the object product.

Production Methods of the Formula (I-1) from the Formula (II-1) and the Formula (II) from the Formula (II-2)

In this reaction, 1 to 3 equivalents of an arylalkylalcohol derivative represented by the formula (III) is reacted with 1 equivalent of a halogenopyrimidine derivative represented by the formula (II-1) in an inert solvent in the presence of a base to give an arylalkyloxypyrimidine derivative represented by the formula (I-1). In addition, 1 to 1.2 equivalents of an arylalkylalcohol derivative represented by the formula (III) is reacted with 1 equivalent of a halogenopyrimidine derivative represented by the formula (II-2) in an inert solvent in the presence of a base to give an arylalkyloxypyrimidine derivative represented by the formula (II). The inert solvent that can be used for this reaction may be any as long as it does not markedly inhibit the progress of the reaction and, for example, chain or cyclic ethers such as diethyl ether, tetrahydrofuran, dioxane and the like, ketones such as acetone, methyl ethyl ketone and the like, aromatic hydrocarbons such as benzene, chlorobenzene and the like, nitriles such as acetonitrile, propionitrile and the like, amides such as dimethylformamide, dimethylacetamide, N-methylpyrrolidone and the like, dimethyl sulfoxide, sulfolane and the like, and water can be mentioned. These inert solvents can be used alone or a mixture of two or more kinds thereof may be used. Examples of the base that can be used for this reaction include inorganic bases such as sodium hydroxide, potassium hydroxide, sodium carbonate, potassium carbonate, cesium carbonate, sodium hydrogen carbonate, potassium hydrogen carbonate and the like, alkali metal hydrides such as sodium hydride, potassium hydride and the like, alkali metal alkoxides such as sodium methoxide, sodium ethoxide, tertiary butoxy potassium and the like, alkyl lithiums such as methyl lithium, normal butyl lithium and the like, and the like. The amount of the base to be used is generally about 1.0- to 1.5-fold mol relative to the arylalkylalcohol derivative represented by the formula (III). This reaction may be performed under an inert gas (nitrogen gas, argon gas) atmosphere in some cases. The reaction temperature can be appropriately selected from 0° C. to the boiling point of the solvent to be used for the reaction. While the reaction time varies depending on the scale of reaction, reaction temperature and the like and is not constant, it can be appropriately selected from several minutes to 48 hours. After completion of the reaction, the object product is isolated from the reaction system containing the object product by a conventional method and purified as necessary by a recrystallization method, a distillation method, a column chromatography method and the like to give the object product.

An arylalkyloxypyrimidine derivative represented by the formula (II) is a novel compound, which is a synthetic intermediate useful for the production of an arylalkyloxypyrimidine derivative represented by of the formula (I). As the halogen atom represented by Hal, a chlorine atom and a bromine atom are preferable, and a chlorine atom is more preferable.

Production Method of the Formula (I-1) from the Formula (II)

This reaction is performed according to the method described in J. Org. Chem., 1955, 20, 225 and the like. That is, an arylalkyloxypyrimidine derivative represented by the formula (I-1) can be produced by catalytic hydrogenation of an arylalkyloxypyrimidine derivative represented by the formula (II) in the presence of a base and a catalyst in an inert solvent under a hydrogen atmosphere. Alternatively, it may be produced by generating hydrogen in the reaction system using formic acid instead of a hydrogen atmosphere.

Examples of the catalyst that can be used for this reaction include tetrakis(triphenylphosphine)palladium, palladium-carbon, platinum, Raney-nickel and the like. The amount of the catalyst to be used is about 0.0001- to 0.1-fold mol relative to the arylalkyloxypyrimidine derivative represented by the formula (II).

This reaction is performed in the presence of a phase-transfer catalyst (e.g., quaternary ammonium salts such as tetrabutylammonium bromide, benzyltriethylammonium bromide and the like, and the like) as necessary.

Examples of the base that can be used for this reaction include inorganic bases such as sodium hydroxide, potassium hydroxide, sodium carbonate, potassium carbonate, cesium carbonate, sodium hydrogen carbonate, potassium hydrogen carbonate and the like, organic bases such as triethylamine, pyridine, sodium acetate, potassium acetate and the like, and the like. The amount of the base to be used is generally about 0.5- to 10-fold mol relative to the arylalkyloxypyrimidine derivative represented by the formula (II).

Examples of the inert solvent that can be used for this reaction include alcohols such as methanol, ethanol and the like, ethers such as tetrahydrofuran, dioxane, dimethoxyethane (DME) and the like, amides such as dimethylformamide, dimethylacetamide, N-methylpyrrolidone and the like, water and the like. These inert solvents can be used alone or a mixture of two or more kinds thereof may be used.

The reaction temperature in this reaction may be generally from about 0° C. to the boiling point of the solvent to be used. While the reaction time varies depending on the reaction scale, reaction temperature and the like and is not constant, it can be appropriately selected from several minutes to 48 hours. For production under a hydrogen atmosphere, the hydrogen pressure can be appropriately selected from the normal pressure to 10 atm. When formic acid is used, the reaction is preferably performed under an inert gas atmosphere such as nitrogen gas and argon gas.

After completion of the reaction, the objective substance may be isolated from the reaction system containing the objective substance by a conventional method and the objective substance can be produced by purification using recrystallization method, distillation method or column chromatography method, etc., if necessary.

Production Method of the Formula (I) from the Formula (I-1)

An arylalkyloxypyrimidine derivative represented by the formula (I) can be produced by reacting an arylalkyloxypyrimidine derivative represented by the formula (I-1) with an oxidant in an inert solvent. Examples of the oxidant to be used in this reaction include manganese compounds such as manganese dioxide and the like; chromates such as sodium chromate and the like; lead compounds such as lead tetraacetate and the like; mercury compounds such as mercury oxide and the like; oxidants such as osmium tetroxide, ruthenium tetroxide, selenium dioxide and the like; metal halide agents such as ferric chloride, copper iodide and the like; halogens such as iodine, bromine and the like; palladiums such as palladium/carbon and the like; quinone oxidants such as DDQ and the like; peroxides such as aqueous hydrogen peroxide, perbenzoic acid, m-chloroperbenzoic acid and the like; and the like. Among these, aqueous hydrogen peroxide, perbenzoic acid and m-chloroperbenzoic acid are preferable. These oxidants can be appropriately selected from 0.8- to 10-fold mol, preferably 1- to 2-fold mol, relative to the arylalkyloxypyrimidine derivative represented by the formula (I-1).

The inert solvent usable in the present reaction may be any as long as it does not markedly inhibit this reaction and, for example, chain or cyclic ethers such as diethyl ether, tetrahydrofuran, dioxane and the like; aromatic hydrocarbons such as benzene, toluene, xylene and the like; halogenated hydrocarbons such as methylene chloride, chloroform, carbon tetrachloride and the like, halogenated aromatic hydrocarbons such as chlorobenzene, dichlorobenzene and the like; nitriles such as acetonitrile and the like; esters such as ethyl acetate and the like; organic acids such as formic acid, acetic acid and the like; polar solvents such as N,N-dimethylformamide, N,N-dimethylacetamide, 1,3-dimethyl-2-imidazolinone, water and the like can be mentioned. These inert solvents may be used alone or in a mixture of two or more kinds thereof.

The reaction temperature in this reaction can be appropriately selected from −30° C. to the refluxing temperature of the inert solvent to be used. While the reaction time varies depending on the reaction scale and is not constant, it can be appropriately selected from several minutes to 48 hours.

After completion of the reaction, the objective substance may be isolated from the reaction system containing the objective substance by a conventional method and the objective substance can be produced by purification using recrystallization or column chromatography, etc., if necessary.

Typical examples of the arylalkyloxypyrimidine derivative represented by the formula (I) of the present invention are shown in Table 1 to Table 12, Table 14 and Table 15, to which the present invention is not limited.

In the Tables, "Me" is a methyl group, "Et" is an ethyl group, "Pr" is a propyl group, "Bu" is a butyl group, "Pen" is a pentyl group, "Hex" is a hexyl group, "Hep" is a heptyl group, "Oct" is an octyl group, "Ms" is a methanesulfonyl group, "Bn" is a benzyl group, "Ph" is a phenyl group, "THF" is a tetrahydrofuranyl group, "THP" is a tetrahydropyranyl group, "Py" is a pyridyl group, "TMS" is a trimethylsilyl group, "TBDMS" is a tertiary butyldimethylsilyl group, "n-" is a normal, "i-" is iso, "neo-" is neo, "s-" is secondary, "t-" is tertiary, "c-" is a alicyclic hydrocarbon group, and "=c-Pr" is a cyclopropylidene. The property shown is melting point (° C.) or refractive index $n_D$ (measurement temperature; ° C.). Table 13 shows the $^1$H-NMR data of the compounds indicated with "NMR" in the column of property in Tables 8, 9, 14 and 15.

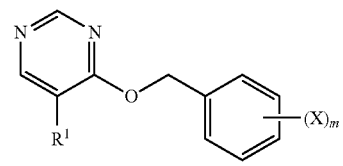

(I-3)

TABLE 1

| Comp. No. | $R^1$ | $(X)_m$ | property value |
|---|---|---|---|
| 1-1 | Me | 4-t-Bu | 50-51 |
| 1-2 | Et | 4-t-Bu | 1.3967(21.8) |
| 1-3 | n-Pr | 4-t-Bu | 1.3268(20.5) |
| 1-4 | i-Pr | 4-t-Bu | 49-50 |

TABLE 1-continued

| Comp. No. | R¹ | (X)$_m$ | property value |
|---|---|---|---|
| 1-5 | c-Pr | 4-t-Bu | 1.5510(21.3) |
| 1-6 | 1,1-Me$_2$-1-Pr | 4-t-Bu | |
| 1-7 | n-Bu | 4-t-Bu | 1.5360(27.5) |
| 1-8 | i-Bu | 4-t-Bu | 1.3067(22.0) |
| 1-9 | s-Bu | 4-t-Bu | 1.4161(17.0) |
| 1-10 | t-Bu | 4-t-Bu | |
| 1-11 | CH$_2$-c-Pr | 4-t-Bu | |
| 1-12 | 2-Me-1-Bu | 4-t-Bu | |
| 1-13 | 3-Me-1-Bu | 4-t-Bu | 1.3960(21.1) |
| 1-14 | n-Pen | 4-t-Bu | 1.5230(20.0) |
| 1-15 | 2-Pen | 4-t-Bu | |
| 1-16 | 3-Pen | 4-t-Bu | |
| 1-17 | neo-Pen | 4-t-Bu | |
| 1-18 | 2-Me-1-Pen | 4-t-Bu | |
| 1-19 | 3-Me-1-Pen | 4-t-Bu | |
| 1-20 | 4-Me-1-Pen | 4-t-Bu | |
| 1-21 | c-Pen | 4-t-Bu | 48-49 |
| 1-22 | n-Hex | 4-t-Bu | |
| 1-23 | 2-Hex | 4-t-Bu | |
| 1-24 | 3-Hex | 4-t-Bu | |
| 1-25 | 1-Me-1-Hex | 4-t-Bu | |
| 1-26 | 2-Me-1-Hex | 4-t-Bu | |
| 1-27 | 3-Me-1-Hex | 4-t-Bu | |
| 1-28 | 4-Me-1-Hex | 4-t-Bu | |
| 1-29 | 5-Me-1-Hex | 4-t-Bu | |
| 1-30 | c-Hex | 4-t-Bu | 105-106 |
| 1-31 | n-Hep | 4-t-Bu | 1.3058(20.5) |
| 1-32 | 2-Hep | 4-t-Bu | |
| 1-33 | 3-Hep | 4-t-Bu | |
| 1-34 | c-Hep | 4-t-Bu | |
| 1-35 | n-Oct | 4-t-Bu | |
| 1-36 | c-Oct | 4-t-Bu | |
| 1-37 | CH=CH$_2$ | 4-t-Bu | 33-34 |
| 1-38 | CH$_2$CH=CH$_2$ | 4-t-Bu | |
| 1-39 | CH$_2$CH=CH | 4-t-Bu | |
| 1-40 | CH$_2$F | 4-t-Bu | 1.5229(21.3) |
| 1-41 | CHF$_2$ | 4-t-Bu | |
| 1-42 | CF$_3$ | 4-t-Bu | |
| 1-43 | CH$_2$CH$_2$F | 4-t-Bu | |
| 1-44 | CH$_2$CHF$_2$ | 4-t-Bu | |
| 1-45 | CH$_2$CF$_3$ | 4-t-Bu | |
| 1-46 | CF$_2$CHF$_2$ | 4-t-Bu | |
| 1-47 | CF$_2$CF$_3$ | 4-t-Bu | |
| 1-48 | CH$_2$CH$_2$CF$_3$ | 4-t-Bu | |
| 1-49 | CH$_2$CF$_2$CF$_3$ | 4-t-Bu | |
| 1-50 | CF$_2$CF$_2$CF$_3$ | 4-t-Bu | |
| 1-51 | CN | 4-t-Bu | |
| 1-52 | CHO | 4-t-Bu | 1.5590(21.0) |
| 1-53 | CH=N—OH | 4-t-Bu | |
| 1-54 | CH=N—OMe | 4-t-Bu | 54-55 |
| 1-55 | CH=N—OEt | 4-t-Bu | 28-29 |
| 1-56 | CH=N—O—c-Pr | 4-t-Bu | |
| 1-57 | CH=N—O—i-Pr | 4-t-Bu | |
| 1-58 | CH=N—OBn | 4-t-Bu | |
| 1-59 | COMe | 4-t-Bu | |
| 1-60 | CMe=N—OH | 4-t-Bu | |
| 1-61 | CMe=N—OMe | 4-t-Bu | |
| 1-62 | CMe=N—OEt | 4-t-Bu | |
| 1-63 | CMe=N—O—c-Pr | 4-t-Bu | |
| 1-64 | CMe=N—O—i-Pr | 4-t-Bu | |
| 1-65 | CMe=N—OBn | 4-t-Bu | |
| 1-66 | CH$_2$OH | 4-t-Bu | |
| 1-67 | CH$_2$OMe | 4-t-Bu | |
| 1-68 | CH$_2$OEt | 4-t-Bu | |
| 1-69 | CH$_2$O—i-Pr | 4-t-Bu | |
| 1-70 | CH$_2$OPh | 4-t-Bu | 57-58 |
| 1-71 | CH$_2$O-2-F—Ph | 4-t-Bu | |
| 1-72 | CH$_2$OCH$_2$OMe | 4-t-Bu | 1.5327(20.5) |
| 1-73 | CH$_2$SMe | 4-t-Bu | |
| 1-74 | CH$_2$SOMe | 4-t-Bu | |
| 1-75 | CH$_2$SO$_2$Me | 4-t-Bu | |
| 1-76 | CH$_2$NMe$_2$ | 4-t-Bu | |
| 1-77 | CHMeOH | 4-t-Bu | |
| 1-78 | CHMeOMe | 4-t-Bu | |
| 1-79 | CHMeOEt | 4-t-Bu | |
| 1-80 | CHMeO—i-Pr | 4-t-Bu | |
| 1-81 | CHMeOPh | 4-t-Bu | |

TABLE 1-continued

| Comp. No. | R¹ | (X)$_m$ | property value |
|---|---|---|---|
| 1-82 | CHMeSMe | 4-t-Bu | |
| 1-83 | CHMeSOMe | 4-t-Bu | |
| 1-84 | CHMeSO$_2$Me | 4-t-Bu | |
| 1-85 | CHMeNMe$_2$ | 4-t-Bu | |
| 1-86 | CO$_2$H | 4-t-Bu | |
| 1-87 | CO$_2$Me | 4-t-Bu | |
| 1-88 | CO$_2$Et | 4-t-Bu | |
| 1-89 | CO$_2$—i-Pr | 4-t-Bu | |
| 1-90 | CO$_2$Ph | 4-t-Bu | |
| 1-91 | CONHMe | 4-t-Bu | |
| 1-92 | CONMe$_2$ | 4-t-Bu | |
| 1-93 | CONHEt | 4-t-Bu | |
| 1-94 | CONEt$_2$ | 4-t-Bu | |
| 1-95 | 2-THF | 4-t-Bu | 1.5418(25.8) |
| 1-96 | 3-THF | 4-t-Bu | |
| 1-97 | 2-THP | 4-t-Bu | |
| 1-98 | 3-THP | 4-t-Bu | |
| 1-99 | 4-THP | 4-t-Bu | |
| 1-100 | Ph | 4-t-Bu | 1.5535(23.0) |
| 1-101 | 2-Py | 4-t-Bu | |
| 1-102 | 3-Py | 4-t-Bu | |
| 1-103 | 4-Py | 4-t-Bu | |
| 1-104 | 2-thienyl | 4-t-Bu | |
| 1-105 | 3-thienyl | 4-t-Bu | |
| 1-106 | 2-furyl | 4-t-Bu | |
| 1-107 | 3-furyl | 4-t-Bu | |
| 1-108 | CH$_2$(1,2,4-triazol-1-yl) | 4-t-Bu | |
| 1-109 | CH$_2$(pyrazol-1-yl) | 4-t-Bu | |
| 1-110 | CH$_2$O-TBDMS | 4-t-Bu | 1.5166(22.0) |

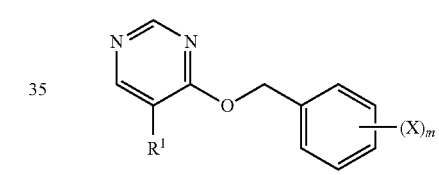

(I-3)

TABLE 2

| Comp. No. | R¹ | (X)$_m$ | property value |
|---|---|---|---|
| 2-1 | Me | 4-CF$_3$ | |
| 2-2 | Et | 4-CF$_3$ | 1.4133(21.6) |
| 2-3 | n-Pr | 4-CF$_3$ | 25 |
| 2-4 | i-Pr | 4-CF$_3$ | 1.4027(21.7) |
| 2-5 | c-Pr | 4-CF$_3$ | 55-57 |
| 2-6 | 1,1-Me$_2$-1-Pr | 4-CF$_3$ | |
| 2-7 | n-Bu | 4-CF$_3$ | 1.4950(27.5) |
| 2-8 | i-Bu | 4-CF$_3$ | 1.3546(19.7) |
| 2-9 | s-Bu | 4-CF$_3$ | 1.3789(20.0) |
| 2-10 | t-Bu | 4-CF$_3$ | |
| 2-11 | CH$_2$—c-Pr | 4-CF$_3$ | |
| 2-12 | 2-Me-1-Bu | 4-CF$_3$ | |
| 2-13 | 3-Me-1-Bu | 4-CF$_3$ | 1.3315(21.1) |
| 2-14 | n-Pen | 4-CF$_3$ | 1.4875(20.0) |
| 2-15 | 2-Pen | 4-CF$_3$ | |
| 2-16 | 3-Pen | 4-CF$_3$ | |
| 2-17 | neo-Pen | 4-CF$_3$ | |
| 2-18 | 2-Me-1-Pen | 4-CF$_3$ | |
| 2-19 | 3-Me-1-Pen | 4-CF$_3$ | |
| 2-20 | 4-Me-1-Pen | 4-CF$_3$ | |
| 2-21 | c-Pen | 4-CF$_3$ | 1.5092(28.5) |
| 2-22 | n-Hex | 4-CF$_3$ | |
| 2-23 | 2-Hex | 4-CF$_3$ | |
| 2-24 | 3-Hex | 4-CF$_3$ | |
| 2-25 | 1-Me-1-Hex | 4-CF$_3$ | |
| 2-26 | 2-Me-1-Hex | 4-CF$_3$ | |
| 2-27 | 3-Me-1-Hex | 4-CF$_3$ | |

TABLE 2-continued

| Comp. No. | R¹ | (X)_m | property value |
|---|---|---|---|
| 2-28 | 4-Me-1-Hex | 4-CF₃ | |
| 2-29 | 5-Me-1-Hex | 4-CF₃ | |
| 2-30 | c-Hex | 4-CF₃ | 35-36 |
| 2-31 | n-Hep | 4-CF₃ | 1.3376(19.2) |
| 2-32 | 2-Hep | 4-CF₃ | |
| 2-33 | 3-Hep | 4-CF₃ | |
| 2-34 | c-Hep | 4-CF₃ | |
| 2-35 | n-Oct | 4-CF₃ | |
| 2-36 | c-Oct | 4-CF₃ | |
| 2-37 | CH=CH₂ | 4-CF₃ | 56-57 |
| 2-38 | CH₂CH=CH₂ | 4-CF₃ | |
| 2-39 | CH₂CH=CH | 4-CF₃ | |
| 2-40 | CH₂F | 4-CF₃ | |
| 2-41 | CHF₂ | 4-CF₃ | 43-44 |
| 2-42 | CF₃ | 4-CF₃ | |
| 2-43 | CH₂CH₂F | 4-CF₃ | |
| 2-44 | CH₂CHF₂ | 4-CF₃ | |
| 2-45 | CH₂CF₃ | 4-CF₃ | |
| 2-46 | CF₂CHF₂ | 4-CF₃ | |
| 2-47 | CF₂CF₃ | 4-CF₃ | |
| 2-48 | CH₂CH₂CF₃ | 4-CF₃ | |
| 2-49 | CH₂CF₂CF₃ | 4-CF₃ | |
| 2-50 | CF₂CF₂CF₃ | 4-CF₃ | |
| 2-51 | CN | 4-CF₃ | 54-56 |
| 2-52 | CHO | 4-CF₃ | 38-39 |
| 2-53 | CH=N—OH | 4-CF₃ | |
| 2-54 | CH=N—OMe | 4-CF₃ | 29-35 |
| 2-55 | CH=N—OEt | 4-CF₃ | 1.5259(21.5) |
| 2-56 | CH=N—O—c-Pr | 4-CF₃ | |
| 2-57 | CH=N—O—i-Pr | 4-CF₃ | 1.5194(21.0) |
| 2-58 | CH=N—O-Bn | 4-CF₃ | |
| 2-59 | COMe | 4-CF₃ | 44-45 |
| 2-60 | CMe=N—OH | 4-CF₃ | |
| 2-61 | CMe=N—OMe | 4-CF₃ | |
| 2-62 | CMe=N—OEt | 4-CF₃ | 1.5142(21.8) |
| 2-63 | CMe=N—O—c-Pr | 4-CF₃ | |
| 2-64 | CMe=N—O—i-Pr | 4-CF₃ | |
| 2-65 | CMe=N—OBn | 4-CF₃ | |
| 2-66 | CH₂OH | 4-CF₃ | 90-91 |
| 2-67 | CH₂OMe | 4-CF₃ | 47-48 |
| 2-68 | CH₂OEt | 4-CF₃ | |
| 2-69 | CH₂O—i-Pr | 4-CF₃ | |
| 2-70 | CH₂OPh | 4-CF₃ | |
| 2-71 | CH₂O-2-F—Ph | 4-CF₃ | 59-60 |
| 2-72 | CH₂OCH₂OMe | 4-CF₃ | |
| 2-73 | CH₂SMe | 4-CF₃ | 1.5368(21.5) |
| 2-74 | CH₂SOMe | 4-CF₃ | 83-84 |
| 2-75 | CH₂SO₂Me | 4-CF₃ | 132-134 |
| 2-76 | CH₂NMe₂ | 4-CF₃ | 1.5047(22.3) |
| 2-77 | CHMeOH | 4-CF₃ | 72-73 |
| 2-78 | CHMeOMe | 4-CF₃ | |
| 2-79 | CHMeOEt | 4-CF₃ | |
| 2-80 | CHMeO—i-Pr | 4-CF₃ | |
| 2-81 | CHMeOPh | 4-CF₃ | |
| 2-82 | CHMeSMe | 4-CF₃ | |
| 2-83 | CHMeSOMe | 4-CF₃ | |
| 2-84 | CHMeSO₂Me | 4-CF₃ | |
| 2-85 | CHMeNMe₂ | 4-CF₃ | |
| 2-86 | CO₂H | 4-CF₃ | 144-146 |
| 2-87 | CO₂Me | 4-CF₃ | 103-105 |
| 2-88 | CO₂Et | 4-CF₃ | 97-98 |
| 2-89 | CO₂—i-Pr | 4-CF₃ | |
| 2-90 | CO₂Ph | 4-CF₃ | |
| 2-91 | CONHMe | 4-CF₃ | |
| 2-92 | CONMe₂ | 4-CF₃ | 66-67 |
| 2-93 | CONHEt | 4-CF₃ | |
| 2-94 | CONEt₂ | 4-CF₃ | |
| 2-95 | 2-THF | 4-CF₃ | 1.5139(26.8) |
| 2-96 | 3-THF | 4-CF₃ | |
| 2-97 | 2-THP | 4-CF₃ | 88-90 |
| 2-98 | 3-THP | 4-CF₃ | |
| 2-99 | 4-THP | 4-CF₃ | |
| 2-100 | Ph | 4-CF₃ | 110-111 |
| 2-101 | 2-Py | 4-CF₃ | |
| 2-102 | 3-Py | 4-CF₃ | 86-89 |
| 2-103 | 4-Py | 4-CF₃ | 88-92 |
| 2-104 | 2-thienyl | 4-CF₃ | 89-91 |
| 2-105 | 3-thienyl | 4-CF₃ | 68-70 |
| 2-106 | 2-furyl | 4-CF₃ | |
| 2-107 | 3-furyl | 4-CF₃ | 65-67 |
| 2-108 | CH₂(1,2,4-triazol-1-yl) | 4-CF₃ | 78-79 |
| 2-109 | CH₂(pyrazol-1-yl) | 4-CF₃ | |

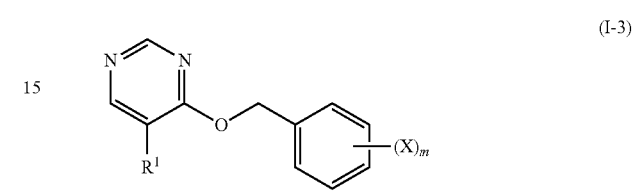

(I-3)

TABLE 3

| Comp. No. | R¹ | (X)_m | property value |
|---|---|---|---|
| 3-1 | Me | 4-OCF₃ | |
| 3-2 | Et | 4-OCF₃ | 1.3982(21.5) |
| 3-3 | n-Pr | 4-OCF₃ | 1.4876(20.5) |
| 3-4 | i-Pr | 4-OCF₃ | 1.4167(21.5) |
| 3-5 | c-Pr | 4-OCF₃ | 1.4986(21.3) |
| 3-6 | 1,1-Me₂-1-Pr | 4-OCF₃ | |
| 3-7 | n-Bu | 4-OCF₃ | 1.4986(28.7) |
| 3-8 | i-Bu | 4-OCF₃ | 1.4717(19.5) |
| 3-9 | s-Bu | 4-OCF₃ | 1.3604(19.9) |
| 3-10 | t-Bu | 4-OCF₃ | |
| 3-11 | CH₂—c-Pr | 4-OCF₃ | |
| 3-12 | 2-Me-1-Bu | 4-OCF₃ | |
| 3-13 | 3-Me-1-Bu | 4-OCF₃ | 1.3862(21.0) |
| 3-14 | n-Pen | 4-OCF₃ | 1.4914(20.0) |
| 3-15 | 2-Pen | 4-OCF₃ | |
| 3-16 | 3-Pen | 4-OCF₃ | |
| 3-17 | neo-Pen | 4-OCF₃ | |
| 3-18 | 2-Me-1-Pen | 4-OCF₃ | |
| 3-19 | 3-Me-1-Pen | 4-OCF₃ | |
| 3-20 | 4-Me-1-Pen | 4-OCF₃ | |
| 3-21 | c-Pen | 4-OCF₃ | 1.5105(20.6) |
| 3-22 | n-Hex | 4-OCF₃ | |
| 3-23 | 2-Hex | 4-OCF₃ | |
| 3-24 | 3-Hex | 4-OCF₃ | |
| 3-25 | 1-Me-1-Hex | 4-OCF₃ | |
| 3-26 | 2-Me-1-Hex | 4-OCF₃ | |
| 3-27 | 3-Me-1-Hex | 4-OCF₃ | |
| 3-28 | 4-Me-1-Hex | 4-OCF₃ | |
| 3-29 | 5-Me-1-Hex | 4-OCF₃ | |
| 3-30 | c-Hex | 4-OCF₃ | |
| 3-31 | n-Hep | 4-OCF₃ | 1.3446(19.5) |
| 3-32 | 2-Hep | 4-OCF₃ | |
| 3-33 | 3-Hep | 4-OCF₃ | |
| 3-34 | c-Hep | 4-OCF₃ | |
| 3-35 | n-Oct | 4-OCF₃ | |
| 3-36 | c-Oct | 4-OCF₃ | |
| 3-37 | CH=CH₂ | 4-OCF₃ | 1.4562(21.2) |
| 3-38 | CH₂CH=CH₂ | 4-OCF₃ | |
| 3-39 | CH₂CH=CH | 4-OCF₃ | |
| 3-40 | CH₂F | 4-OCF₃ | |
| 3-41 | CHF₂ | 4-OCF₃ | |
| 3-42 | CF₃ | 4-OCF₃ | |
| 3-43 | CH₂CH₂F | 4-OCF₃ | |
| 3-44 | CH₂CHF₂ | 4-OCF₃ | |
| 3-45 | CH₂CF₃ | 4-OCF₃ | |
| 3-46 | CF₂CHF₂ | 4-OCF₃ | |
| 3-47 | CF₂CF₃ | 4-OCF₃ | |
| 3-48 | CH₂CH₂CF₃ | 4-OCF₃ | |
| 3-49 | CH₂CF₂CF₃ | 4-OCF₃ | |
| 3-50 | CF₂CF₂CF₃ | 4-OCF₃ | |
| 3-51 | CN | 4-OCF₃ | 1.5156(20.1) |

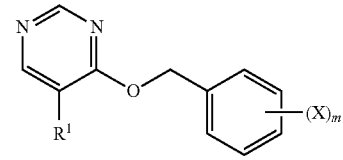

(I-3)

TABLE 3-continued

| Comp. No. | R¹ | (X)_m | property value |
|---|---|---|---|
| 3-52 | CHO | 4-OCF₃ | 1.5089(20.8) |
| 3-53 | CH=N—OH | 4-OCF₃ | |
| 3-54 | CH=N—OMe | 4-OCF₃ | |
| 3-55 | CH=N—OEt | 4-OCF₃ | |
| 3-56 | CH=N—O—c-Pr | 4-OCF₃ | |
| 3-57 | CH=N—O—i-Pr | 4-OCF₃ | |
| 3-58 | CH=N—O—Bn | 4-OCF₃ | |
| 3-59 | COMe | 4-OCF₃ | |
| 3-60 | CMe=N—OH | 4-OCF₃ | |
| 3-61 | CMe=N—OMe | 4-OCF₃ | |
| 3-62 | CMe=N—OEt | 4-OCF₃ | |
| 3-63 | CMe=N—O—c-Pr | 4-OCF₃ | |
| 3-64 | CMe=N—O—i-Pr | 4-OCF₃ | |
| 3-65 | CMe=N—OBn | 4-OCF₃ | |
| 3-66 | CH₂OH | 4-OCF₃ | |
| 3-67 | CH₂OMe | 4-OCF₃ | 35-36 |
| 3-68 | CH₂OEt | 4-OCF₃ | 1.4932(19.4) |
| 3-69 | CH₂O—i-Pr | 4-OCF₃ | |
| 3-70 | CH₂OPh | 4-OCF₃ | |
| 3-71 | CH₂O-2-F—Ph | 4-OCF₃ | |
| 3-72 | CH₂OCH₂OMe | 4-OCF₃ | |
| 3-73 | CH₂SMe | 4-OCF₃ | |
| 3-74 | CH₂SOMe | 4-OCF₃ | |
| 3-75 | CH₂SO₂Me | 4-OCF₃ | |
| 3-76 | CH₂NMe₂ | 4-OCF₃ | |
| 3-77 | CHMeOH | 4-OCF₃ | |
| 3-78 | CHMeOMe | 4-OCF₃ | 1.4922(21.5) |
| 3-79 | CHMeOEt | 4-OCF₃ | |
| 3-80 | CHMeO—i-Pr | 4-OCF₃ | |
| 3-81 | CHMeOPh | 4-OCF₃ | |
| 3-82 | CHMeSMe | 4-OCF₃ | |
| 3-83 | CHMeSOMe | 4-OCF₃ | |
| 3-84 | CHMeSO₂Me | 4-OCF₃ | |
| 3-85 | CHMeNMe₂ | 4-OCF₃ | |
| 3-86 | CO₂H | 4-OCF₃ | |
| 3-87 | CO₂Me | 4-OCF₃ | |
| 3-88 | CO₂Et | 4-OCF₃ | 28-29 |
| 3-89 | CO₂—i-Pr | 4-OCF₃ | |
| 3-90 | CO₂Ph | 4-OCF₃ | |
| 3-91 | CONHMe | 4-OCF₃ | |
| 3-92 | CONMe₂ | 4-OCF₃ | |
| 3-93 | CONHEt | 4-OCF₃ | |
| 3-94 | CONEt₂ | 4-OCF₃ | |
| 3-95 | 2-THF | 4-OCF₃ | 1.5086(25.8) |
| 3-96 | 3-THF | 4-OCF₃ | |
| 3-97 | 2-THP | 4-OCF₃ | |
| 3-98 | 3-THP | 4-OCF₃ | |
| 3-99 | 4-THP | 4-OCF₃ | |
| 3-100 | Ph | 4-OCF₃ | |
| 3-101 | 2-Py | 4-OCF₃ | |
| 3-102 | 3-Py | 4-OCF₃ | |
| 3-103 | 4-Py | 4-OCF₃ | |
| 3-104 | 2-thienyl | 4-OCF₃ | |
| 3-105 | 3-thienyl | 4-OCF₃ | |
| 3-106 | 2-furyl | 4-OCF₃ | |
| 3-107 | 3-furyl | 4-OCF₃ | |
| 3-108 | CH₂(1,2,4-triazol-1-yl) | 4-OCF₃ | |
| 3-109 | CH₂(pyrazol-1-yl) | 4-OCF₃ | |
| 3-110 | CH=N—OSO₂Me | 4-OCF₃ | 107-111 |
| 3-111 | (isoxazoline structure) | 4-OCF₃ | 51-52 |

TABLE 4

| Comp. No. | R¹ | (X)_m | property value |
|---|---|---|---|
| 4-1 | 1,3-dioxolan-2-yl | 4-t-Bu | 83-84 |
| 4-2 | 1,3-dioxolan-2-yl | 4-O—i-Pr | |
| 4-3 | 1,3-dioxolan-2-yl | 4-TMS | 68-69 |
| 4-4 | 1,3-dioxolan-2-yl | 4-CF₃ | 38-39 |
| 4-5 | 1,3-dioxolan-2-yl | 4-OCF₃ | |
| 4-6 | 4,5-Me₂-1,3-dioxolan(trans)-2-yl | 4-t-Bu | 59-60 |
| 4-7 | 4,5-Me₂-1,3-dioxolan(trans)-2-yl | 4-O—i-Pr | |
| 4-8 | 4,5-Me₂-1,3-dioxolan(trans)-2-yl | 4-TMS | |
| 4-9 | 4,5-Me₂-1,3-dioxolan(trans)-2-yl | 4-CF₃ | 54-55 |
| 4-10 | 4,5-Me₂-1,3-dioxolan(trans)-2-yl | 4-OCF₃ | 1.4965(20.0) |
| 4-11 | 4,5-Me₂-1,3-dioxolan(cis)-2-yl | 4-t-Bu | |
| 4-12 | 4,5-Me₂-1,3-dioxolan(cis)-2-yl | 4-O—i-Pr | |
| 4-13 | 4,5-Me₂-1,3-dioxolan(cis)-2-yl | 4-TMS | |
| 4-14 | 4,5-Me₂-1,3-dioxolan(cis)-2-yl | 4-CF₃ | |
| 4-15 | 4,5-Me₂-1,3-dioxolan(cis)-2-yl | 4-OCF₃ | |
| 4-16 | 1,3-dioxan-2-yl | 4-t-Bu | 84-85 |
| 4-17 | 1,3-dioxan-2-yl | 4-O—i-Pr | 1.4238(26.9) |
| 4-18 | 1,3-dioxan-2-yl | 4-TMS | 70-71 |
| 4-19 | 1,3-dioxan-2-yl | 4-CF₃ | 105-106 |
| 4-20 | 1,3-dioxan-2-yl | 4-OCF₃ | 86-87 |
| 4-21 | 1,3-dioxan-2-yl | 4-SCF₃ | 122-123 |
| 4-22 | 1,3-dioxan-2-yl | 4-Cl | 84-85 |
| 4-23 | 5,5-Me₂-1,3-dioxan-2-yl | 4-t-Bu | 61-62 |
| 4-24 | 5,5-Me₂-1,3-dioxan-2-yl | 4-O—i-Pr | |
| 4-25 | 5,5-Me₂-1,3-dioxan-2-yl | 4-TMS | |
| 4-26 | 5,5-Me₂-1,3-dioxan-2-yl | 4-CF₃ | 114-115 |
| 4-27 | 5,5-Me₂-1,3-dioxan-2-yl | 4-OCF₃ | |
| 4-28 | 4,6-Me₂-1,3-dioxan(trans)-2-yl | 4-t-Bu | 61-62 |
| 4-29 | 4,6-Me₂-1,3-dioxan(trans)-2-yl | 4-O—i-Pr | |
| 4-30 | 4,6-Me₂-1,3-dioxan(trans)-2-yl | 4-TMS | |
| 4-31 | 4,6-Me₂-1,3-dioxan(trans)-2-yl | 4-CF₃ | 91-92 |
| 4-32 | 4,6-Me₂-1,3-dioxan(trans)-2-yl | 4-OCF₃ | |
| 4-33 | 4,6-Me₂-1,3-dioxan(cis)-2-yl | 4-t-Bu | 68-69 |
| 4-34 | 4,6-Me₂-1,3-dioxan(cis)-2-yl | 4-O—i-Pr | |
| 4-35 | 4,6-Me₂-1,3-dioxan(cis)-2-yl | 4-TMS | |
| 4-36 | 4,6-Me₂-1,3-dioxan(cls)-2-yl | 4-CF₃ | 148-149 |
| 4-37 | 4,6-Me₂-1,3-dioxan(cis)-2-yl | 4-OCF₃ | |
| 4-38 | 1,3-dioxepan-2-yl | 4-t-Bu | 75-76 |
| 4-39 | 1,3-dioxepan-2-yl | 4-O—i-Pr | |
| 4-40 | 1,3-dioxepan-2-yl | 4-TMS | 1.5406(21.3) |
| 4-41 | 1,3-dioxepan-2-yl | 4-CF₃ | 95-96 |
| 4-42 | 1,3-dioxepan-2-yl | 4-OCF₃ | 92-93 |
| 4-43 | CH(OMe)₂ | 4-t-Bu | 68-69 |
| 4-44 | CH(OMe)₂ | 4-O—i-Pr | 1.4255(20.6) |
| 4-45 | CH(OMe)₂ | 4-TMS | 1.5284(21.3) |
| 4-46 | CH(OMe)₂ | 4-CF₃ | 45-46 |
| 4-47 | CH(OMe)₂ | 4-OCF₃ | 30-31 |
| 4-48 | CH(OEt)₂ | 4-t-Bu | |
| 4-49 | CH(OEt)₂ | 4-O—i-Pr | |
| 4-50 | CH(OEt)₂ | 4-TMS | |
| 4-51 | CH(OEt)₂ | 4-CF₃ | 40-41 |
| 4-52 | CH(OEt)₂ | 4-OCF₃ | 1.4843(21.9) |
| 4-53 | 1,3-oxathiolan-2-yl | 4-t-Bu | 111-113 |
| 4-54 | 1,3-oxathiolan-2-yl | 4-O—i-Pr | |
| 4-55 | 1,3-oxathiolan-2-yl | 4-TMS | |
| 4-56 | 1,3-oxathiolan-2-yl | 4-CF₃ | 94-96 |
| 4-57 | 1,3-oxathiolan-2-yl | 4-OCF₃ | 86-88 |
| 4-58 | oxazolidin-2-yl | 4-t-Bu | |
| 4-59 | oxazolidin-2-yl | 4-O—i-Pr | |
| 4-60 | oxazolidin-2-yl | 4-TMS | |
| 4-61 | oxazolidin-2-yl | 4-CF₃ | |
| 4-62 | oxazolidin-2-yl | 4-OCF₃ | |
| 4-63 | 1,3-dithiolan-2-yl | 4-t-Bu | 74-76 |
| 4-64 | 1,3-dithiolan-2-yl | 4-O—i-Pr | |

TABLE 4-continued

| Comp. No. | R¹ | (X)$_m$ | property value |
|---|---|---|---|
| 4-65 | 1,3-dithiolan-2-yl | 4-TMS | |
| 4-66 | 1,3-dithiolan-2-yl | 4-CF₃ | 88-89 |
| 4-67 | 1,3-dithiolan-2-yl | 4-OCF₃ | 72-73 |
| 4-68 | 1,3-dithian-2-yl | 4-t-Bu | 123-125 |
| 4-69 | 1,3-dithian-2-yl | 4-O—i-Pr | |
| 4-70 | 1,3-dithian-2-yl | 4-TMS | |
| 4-71 | 1,3-dithian-2-yl | 4-CF₃ | 124-126 |
| 4-72 | 1,3-dithian-2-yl | 4-OCF₃ | 116-117 |
| 4-73 | imidazolidin-2-yl | 4-t-Bu | |
| 4-74 | imidazolidin-2-yl | 4-O—i-Pr | |
| 4-75 | imidazolidin-2-yl | 4-TMS | |
| 4-76 | imidazolidin-2-yl | 4-CF₃ | |
| 4-77 | imidazolidin-2-yl | 4-OCF₃ | |
| 4-78 | CH(SMe)₂ | 4-t-Bu | 1.3999(20.8) |
| 4-79 | CH(SMe)₂ | 4-O—i-Pr | |
| 4-80 | CH(SMe)₂ | 4-TMS | |
| 4-81 | CH(SMe)₂ | 4-CF₃ | 73-74 |
| 4-82 | CH(SMe)₂ | 4-OCF₃ | 1.4826(21.0) |
| 4-83 | CH(SEt)₂ | 4-t-Bu | 1.4209(20.7) |
| 4-84 | CH(SEt)₂ | 4-O—i-Pr | |
| 4-85 | CH(SEt)₂ | 4-TMS | |
| 4-86 | CH(SEt)₂ | 4-CF₃ | 1.3869(20.6) |
| 4-87 | CH(SEt)₂ | 4-OCF₃ | 1.3941(20.6) |
| 4-88 | CH(OMe)(1,2,4-triazol-1-yl) | 4-CF₃ | 83-84 |
| 4-89 | CH(OMe)(pyrazol-1-yl) | 4-CF₃ | 41-42 |
| 4-90 | (see structure) | 4-CF₃ | 75-76 |
| 4-91 | (see structure) | 4-CF₃ | 67-68 |

(I-1)

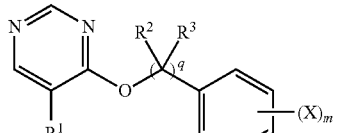

TABLE 5

(q = 1, Y = CH)

| Comp. No. | R¹ | R² | R³ | (X)$_m$ | property value |
|---|---|---|---|---|---|
| 5-1 | c-Hex | CF₃ | H | H | 1.5400(21.0) |
| 5-2 | c-Hex | CF₃ | H | 4-t-Bu | 1.4491(21.0) |
| 5-3 | c-Hex | H | H | 4-SCF₃ | 73-74 |

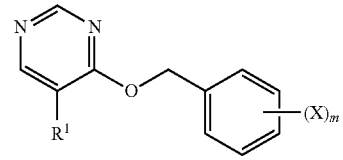

(I-3)

TABLE 6

| Comp. No. | R¹ | (X)$_m$ | property value |
|---|---|---|---|
| 6-1 | Me | 4-O—i-Pr | |
| 6-2 | Et | 4-O—i-Pr | |
| 6-3 | n-Pr | 4-O—i-Pr | |
| 6-4 | i-Pr | 4-O—i-Pr | |
| 6-5 | c-Pr | 4-O—i-Pr | |
| 6-6 | 1,1-Me₂-1-Pr | 4-O—i-Pr | |
| 6-7 | n-Bu | 4-O—i-Pr | |
| 6-8 | i-Bu | 4-O—i-Pr | |
| 6-9 | s-Bu | 4-O—i-Pr | |
| 6-10 | t-Bu | 4-O—i-Pr | |
| 6-11 | CH₂-c-Pr | 4-O—i-Pr | |
| 6-12 | 2-Me-1-Bu | 4-O—i-Pr | |
| 6-13 | 3-Me-1-Bu | 4-O—i-Pr | |
| 6-14 | n-Pen | 4-O—i-Pr | |
| 6-15 | 2-Pen | 4-O—i-Pr | |
| 6-16 | 3-Pen | 4-O—i-Pr | |
| 6-17 | neo-Pen | 4-O—i-Pr | |
| 6-18 | 2-Me-1-Pen | 4-O—i-Pr | |
| 6-19 | 3-Me-1-Pen | 4-O—i-Pr | |
| 6-20 | 4-Me-1-Pen | 4-O—i-Pr | |
| 6-21 | c-Pen | 4-O—i-Pr | |
| 6-22 | n-Hex | 4-O—i-Pr | |
| 6-23 | 2-Hex | 4-O—i-Pr | |
| 6-24 | 3-Hex | 4-O—i-Pr | |
| 6-25 | 1-Me-1-Hex | 4-O—i-Pr | |
| 6-26 | 2-Me-1-Hex | 4-O—i-Pr | |
| 6-27 | 3-Me-1-Hex | 4-O—i-Pr | |
| 6-28 | 4-Me-1-Hex | 4-O—i-Pr | |
| 6-29 | 5-Me-1-Hex | 4-O—i-Pr | |
| 6-30 | c-Hex | 4-O—i-Pr | |
| 6-31 | n-Hep | 4-O—i-Pr | |
| 6-32 | 2-Hep | 4-O—i-Pr | |
| 6-33 | 3-Hep | 4-O—i-Pr | |
| 6-34 | c-Hep | 4-O—i-Pr | |
| 6-35 | n-Oct | 4-O—i-Pr | |
| 6-36 | c-Oct | 4-O—i-Pr | |
| 6-37 | CH=CH₂ | 4-O—i-Pr | |
| 6-38 | CH₂CH=CH₂ | 4-O—i-Pr | |
| 6-39 | CH₂CH=CH | 4-O—i-Pr | |
| 6-40 | CH₂F | 4-O—i-Pr | |
| 6-41 | CHF₂ | 4-O—i-Pr | |
| 6-42 | CF₃ | 4-O—i-Pr | |
| 6-43 | CH₂CH₂F | 4-O—i-Pr | |
| 6-44 | CH₂CHF₂ | 4-O—i-Pr | |
| 6-45 | CH₂CF₃ | 4-O—i-Pr | |
| 6-46 | CF₂CHF₂ | 4-O—i-Pr | |
| 6-47 | CF₂CF₃ | 4-O—i-Pr | |
| 6-48 | CH₂CH₂CF₃ | 4-O—i-Pr | |
| 6-49 | CH₂CF₂CF₃ | 4-O—i-Pr | |
| 6-50 | CF₂CF₂CF₃ | 4-O—i-Pr | |
| 6-51 | CN | 4-O—i-Pr | |
| 6-52 | CHO | 4-O—i-Pr | |
| 6-53 | CH=N—OH | 4-O—i-Pr | |
| 6-54 | CH=N—OMe | 4-O—i-Pr | |
| 6-55 | CH=N—OEt | 4-O—i-Pr | |
| 6-56 | CH=N—O—c-Pr | 4-O—i-Pr | |
| 6-57 | CH=N—O—i-Pr | 4-O—i-Pr | |
| 6-58 | CH=N—OBn | 4-O—i-Pr | |
| 6-59 | COMe | 4-O—i-Pr | |
| 6-60 | CMe=N—OH | 4-O—i-Pr | |
| 6-61 | CMe=N—OMe | 4-O—i-Pr | |
| 6-62 | CMe=N—OEt | 4-O—i-Pr | |
| 6-63 | CMe=N—O—c-Pr | 4-O—i-Pr | |
| 6-64 | CMe=N—O—i-Pr | 4-O—i-Pr | |

TABLE 6-continued

| Comp. No. | R¹ | (X)ₘ | property value |
|---|---|---|---|
| 6-65 | CMe=N—OBn | 4-O—i-Pr | |
| 6-66 | CH₂OH | 4-O—i-Pr | |
| 6-67 | CH₂OMe | 4-O—i-Pr | |
| 6-68 | CH₂OEt | 4-O—i-Pr | |
| 6-69 | CH₂O—i-Pr | 4-O—i-Pr | |
| 6-70 | CH₂OPh | 4-O—i-Pr | |
| 6-71 | CH₂O-2-F—Ph | 4-O—i-Pr | |
| 6-72 | CH₂OCH₂OMe | 4-O—i-Pr | |
| 6-73 | CH₂SMe | 4-O—i-Pr | |
| 6-74 | CH₂SOMe | 4-O—i-Pr | |
| 6-75 | CH₂SO₂Me | 4-O—i-Pr | |
| 6-76 | CH₂NMe₂ | 4-O—i-Pr | |
| 6-77 | CHMeOH | 4-O—i-Pr | |
| 6-78 | CHMeOMe | 4-O—i-Pr | |
| 6-79 | CHMeOEt | 4-O—i-Pr | |
| 6-80 | CHMeO—i-Pr | 4-O—i-Pr | |
| 6-81 | CHMeOPh | 4-O—i-Pr | |
| 6-82 | CHMeSMe | 4-O—i-Pr | |
| 6-83 | CHMeSOMe | 4-O—i-Pr | |
| 6-84 | CHMeSO₂Me | 4-O—i-Pr | |
| 6-85 | CHMeNMe₂ | 4-O—i-Pr | |
| 6-86 | CO₂H | 4-O—i-Pr | |
| 6-87 | CO₂Me | 4-O—i-Pr | |
| 6-88 | CO₂Et | 4-O—i-Pr | |
| 6-89 | CO₂—i-Pr | 4-O—i-Pr | |
| 6-90 | CO₂Ph | 4-O—i-Pr | |
| 6-91 | CONHMe | 4-O—i-Pr | |
| 6-92 | CONMe₂ | 4-O—i-Pr | |
| 6-93 | CONHEt | 4-O—i-Pr | |
| 6-94 | CONEt₂ | 4-O—i-Pr | |
| 6-95 | 2-THF | 4-O—i-Pr | |
| 6-96 | 3-THF | 4-O—i-Pr | |
| 6-97 | 2-THP | 4-O—i-Pr | |
| 6-98 | 3-THP | 4-O—i-Pr | |
| 6-99 | 4-THP | 4-O—i-Pr | |
| 6-100 | Ph | 4-O—i-Pr | |
| 6-101 | 2-Py | 4-O—i-Pr | |
| 6-102 | 3-Py | 4-O—i-Pr | |
| 6-103 | 4-Py | 4-O—i-Pr | |
| 6-104 | 2-thienyl | 4-O—i-Pr | |
| 6-105 | 3-thienyl | 4-O—i-Pr | |
| 6-106 | 2-furyl | 4-O—i-Pr | |
| 6-107 | 3-furyl | 4-O—i-Pr | |
| 6-108 | CH₂(1,2,4-triazol-1-yl) | 4-O—i-Pr | |
| 6-109 | CH₂(pyrazol-1-yl) | 4-O—i-Pr | |

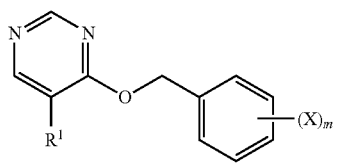

(I-3)

TABLE 7

| Comp. No. | R¹ | (X)ₘ | property value |
|---|---|---|---|
| 7-1 | Me | 4-TMS | |
| 7-2 | Et | 4-TMS | |
| 7-3 | n-Pr | 4-TMS | |
| 7-4 | i-Pr | 4-TMS | |
| 7-5 | c-Pr | 4-TMS | |
| 7-6 | 1,1-Me₂-1-n-Pr | 4-TMS | |
| 7-7 | n-Bu | 4-TMS | |
| 7-8 | i-Bu | 4-TMS | |
| 7-9 | s-Bu | 4-TMS | |
| 7-10 | t-Bu | 4-TMS | |
| 7-11 | CH₂—c-Pr | 4-TMS | |

TABLE 7-continued

| Comp. No. | R¹ | (X)ₘ | property value |
|---|---|---|---|
| 7-12 | 2-Me-1-n-Bu | 4-TMS | |
| 7-13 | 3-Me-1-n-Bu | 4-TMS | |
| 7-14 | n-Pen | 4-TMS | |
| 7-15 | 2-Pen | 4-TMS | |
| 7-16 | 3-Pen | 4-TMS | |
| 7-17 | neo-Pen | 4-TMS | |
| 7-18 | 2-Me-1-n-Pen | 4-TMS | |
| 7-19 | 3-Me-1-n-Pen | 4-TMS | |
| 7-20 | 4-Me-1-n-Pen | 4-TMS | |
| 7-21 | c-Pen | 4-TMS | |
| 7-22 | n-Hex | 4-TMS | |
| 7-23 | 2-Hex | 4-TMS | |
| 7-24 | 3-Hex | 4-TMS | |
| 7-25 | 1-Me-1-n-Hex | 4-TMS | |
| 7-26 | 2-Me-1-n-Hex | 4-TMS | |
| 7-27 | 3-Me-1-n-Hex | 4-TMS | |
| 7-28 | 4-Me-1-n-Hex | 4-TMS | |
| 7-29 | 5-Me-1-n-Hex | 4-TMS | |
| 7-30 | c-Hex | 4-TMS | |
| 7-31 | n-Hep | 4-TMS | |
| 7-32 | 2-Hep | 4-TMS | |
| 7-33 | 3-Hep | 4-TMS | |
| 7-34 | c-Hep | 4-TMS | |
| 7-35 | n-Oct | 4-TMS | |
| 7-36 | c-Oct | 4-TMS | |
| 7-37 | CH=CH₂ | 4-TMS | |
| 7-38 | CH₂CH=CH₂ | 4-TMS | |
| 7-39 | CH₂CH=CH | 4-TMS | |
| 7-40 | CH₂F | 4-TMS | |
| 7-41 | CHF₂ | 4-TMS | |
| 7-42 | CF₃ | 4-TMS | |
| 7-43 | CH₂CH₂F | 4-TMS | |
| 7-44 | CH₂CHF₂ | 4-TMS | |
| 7-45 | CH₂CF₃ | 4-TMS | |
| 7-46 | CF₂CHF₂ | 4-TMS | |
| 7-47 | CF₂CF₃ | 4-TMS | |
| 7-48 | CH₂CH₂CF₃ | 4-TMS | |
| 7-49 | CH₂CF₂CF₃ | 4-TMS | |
| 7-50 | CF₂CF₂CF₃ | 4-TMS | |
| 7-51 | CN | 4-TMS | |
| 7-52 | CHO | 4-TMS | 1.5488(21.3) |
| 7-53 | CH=N—OH | 4-TMS | |
| 7-54 | CH=N—OMe | 4-TMS | |
| 7-55 | CH=N—OEt | 4-TMS | |
| 7-56 | CH=N—O—c-Pr | 4-TMS | |
| 7-57 | CH=N—O—i-Pr | 4-TMS | |
| 7-58 | CH=N—OBn | 4-TMS | |
| 7-59 | COMe | 4-TMS | |
| 7-60 | CMe=N—OH | 4-TMS | |
| 7-61 | CMe=N—OMe | 4-TMS | |
| 7-62 | CMe=N—OEt | 4-TMS | |
| 7-63 | CMe=N—O—c-Pr | 4-TMS | |
| 7-64 | CMe=N—O—i-Pr | 4-TMS | |
| 7-65 | CMe=N—OBn | 4-TMS | |
| 7-66 | CH₂OH | 4-TMS | 70-71 |
| 7-67 | CH₂OMe | 4-TMS | |
| 7-68 | CH₂OEt | 4-TMS | |
| 7-69 | CH₂O—i-Pr | 4-TMS | |
| 7-70 | CH₂OPh | 4-TMS | |
| 7-71 | CH₂O-2-F—Ph | 4-TMS | |
| 7-72 | CH₂OCH₂OMe | 4-TMS | |
| 7-73 | CH₂SMe | 4-TMS | |
| 7-74 | CH₂SOMe | 4-TMS | |
| 7-75 | CH₂SO₂Me | 4-TMS | |
| 7-76 | CH₂NMe₂ | 4-TMS | |
| 7-77 | CHMeOH | 4-TMS | |
| 7-78 | CHMeOMe | 4-TMS | |
| 7-79 | CHMeOEt | 4-TMS | |
| 7-80 | CHMeO—i-Pr | 4-TMS | |
| 7-81 | CHMeOPh | 4-TMS | |
| 7-82 | CHMeSMe | 4-TMS | |
| 7-83 | CHMeSOMe | 4-TMS | |
| 7-84 | CHMeSO₂Me | 4-TMS | |
| 7-85 | CHMeNMe₂ | 4-TMS | |
| 7-86 | CO₂H | 4-TMS | |
| 7-87 | CO₂Me | 4-TMS | |
| 7-88 | CO₂Et | 4-TMS | |

TABLE 7-continued

| Comp. No. | R¹ | (X)$_m$ | property value |
|---|---|---|---|
| 7-89 | CO$_2$—i-Pr | 4-TMS | |
| 7-90 | CO$_2$Ph | 4-TMS | |
| 7-91 | CONHMe | 4-TMS | |
| 7-92 | CONMe$_2$ | 4-TMS | |
| 7-93 | CONHEt | 4-TMS | |
| 7-94 | CONEt$_2$ | 4-TMS | |
| 7-95 | 2-THF | 4-TMS | |
| 7-96 | 3-THF | 4-TMS | |
| 7-97 | 2-THP | 4-TMS | |
| 7-98 | 3-THP | 4-TMS | |
| 7-99 | 4-THP | 4-TMS | |
| 7-100 | Ph | 4-TMS | |
| 7-101 | 2-Py | 4-TMS | |
| 7-102 | 3-Py | 4-TMS | |
| 7-103 | 4-Py | 4-TMS | |
| 7-104 | 2-thienyl | 4-TMS | |
| 7-105 | 3-thienyl | 4-TMS | |
| 7-106 | 2-furyl | 4-TMS | |
| 7-107 | 3-furyl | 4-TMS | |
| 7-108 | CH$_2$(1,2,4-triazol-1-yl) | 4-TMS | |
| 7-109 | CH$_2$(pyrazol-1-yl) | 4-TMS | |

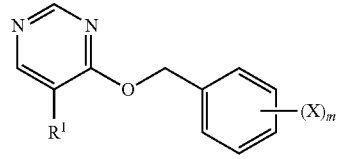

(I-3)

TABLE 8

| Comp. No. | R¹ | (X)$_m$ | property value |
|---|---|---|---|
| 8-1 | CH$_2$Ph | 4-CF$_3$ | 47-48 |
| 8-2 | CH$_2$Ph | 4-t-Bu | 1.5658(20.1) |
| 8-3 | CH$_2$Ph | 4-OCF$_3$ | 1.5374(20.1) |
| 8-4 | CH=N—OSO$_2$Me | 4-OCF$_3$ | 107-111 |
| 8-5 | CH=N—OCH$_2$C≡CH | 4-CF$_3$ | 47-49 |
| 8-6 | CH=N—O—i-Bu | 4-CF$_3$ | 1.5166(21.0) |
| 8-7 | n-Pr | 4-SCF$_3$ | 30-31 |
| 8-8 | n-Pr | 4-Cl | 1.3476(21.2) |
| 8-9 | CMe=N—OEt | 4-CF$_3$ | 1.5096(21.8) |
| 8-10 | CH=N-3-Py | 4-t-Bu | NMR |
| 8-11 | CONHCH$_2$CF$_3$ | 4-t-Bu | 32-33 |
| 8-12 | CH=CH$_2$ | 4-Cl | 40-42 |
| 8-13 | CONHCH$_2$CF$_3$ | 4-CF$_3$ | 94-96 |
| 8-14 | i-Bu | 2,4-Cl$_2$ | 1.3916(19.4) |
| 8-15 | CH$_2$CH$_2$SPh | 4-CF$_3$ | 76-77 |
| 8-16 | CH$_2$CH$_2$SOPh | 4-CF$_3$ | 85-86 |
| 8-17 | CH$_2$CH$_2$SO$_2$Ph | 4-CF$_3$ | 98-99 |
| 8-18 | C≡CTMS | 4-CF$_3$ | 82-83 |
| 8-19 | C≡CH | 4-CF$_3$ | 120-121 |
| 8-20 | CH$_2$CH$_2$OEt | 4-t-Bu | 1.3662(21.5) |
| 8-21 | CONHPh | 4-CF$_3$ | 158-159 |
| 8-22 | 2-F—Ph | 4-CF$_3$ | 120-122 |
| 8-23 | CH$_2$CH$_2$OEt | 4-CF$_3$ | 1.4067(19.9) |
| 8-24 | CH$_2$CH$_2$OEt | 4-OCF$_3$ | 1.3869(19.8) |
| 8-25 | CH(OH)CH$_2$OH | 4-t-Bu | 1.3494(21.2) |
| 8-26 | CH$_2$CH$_2$OMe | 4-t-Bu | 1.3577(21.5) |
| 8-27 | CH$_2$CH$_2$OMe | 4-CF$_3$ | 1.3899(21.4) |
| 8-28 | CH$_2$CH$_2$OMe | 4-OCF$_3$ | 1.3677(21.3) |
| 8-29 | C≡CH$_2$OMe | 4-CF$_3$ | 52-54 |
| 8-30 | (5-methyl-3-phenyl-4,5-dihydroisoxazol-5-yl) | 4-t-Bu | 1.3329(21.1) |
| 8-31 | CH$_2$CH$_2$CH$_2$Cl | 4-OCF$_3$ | 1.4369(21.0) |
| 8-32 | C≡CMe | 4-CF$_3$ | 84-85 |
| 8-33 | C≡CCMe$_2$OH | 4-CF$_3$ | 121-122 |
| 8-34 | (3,6-dihydro-2H-pyran-4-yl) | 4-CF$_3$ | 68-70 |
| 8-35 | N—Me-pyrazol-4-yl | 4-CF$_3$ | 101-103 |
| 8-36 | C≡CCH$_2$OH | 4-CF$_3$ | 98-100 |
| 8-37 | CH$_2$CH$_2$CH$_2$Cl | 4-t-Bu | 1.4169(20.8) |
| 8-38 | CH(OH)CH$_2$OCMe$_2$OMe | 4-t-Bu | 1.3542(24.3) |
| 8-39 | C≡CCH$_2$F | 4-CF$_3$ | 66-69 |
| 8-40 | CONHCH$_2$CH$_2$OH | 4-CF$_3$ | 86-89 |
| 8-41 | CH(OH)CH$_2$OH | 4-CF$_3$ | 102-104 |
| 8-42 | CH(OMe)CH$_2$OMe | 4-CF$_3$ | 1.3546(20.7) |
| 8-43 | CH(OEt)CH$_2$OEt | 4-CF$_3$ | 1.3627(20.7) |
| 8-44 | CH(OH)CH$_2$OEt | 4-CF$_3$ | 1.3039(20.6) |
| 8-45 | CH$_2$NHCOMe | 4-CF$_3$ | 134-135 |
| 8-46 | (5-oxo-4,5-dihydro-1,3,4-oxadiazol-2-yl) | 4-t-Bu | 207-208 |
| 8-47 | CHBrCH$_2$Br | 4-CF$_3$ | 118-120 |
| 8-48 | (3-methyl-4,5-dihydroisoxazol-5-yl) | 4-CF$_3$ | 1.2996(23.6) |
| 8-49 | CH=C(CO$_2$Me)$_2$ | 4-OCF$_3$ | 1.4840(22.6) |
| 8-50 | (3-chloro-4,5-dihydroisoxazol-5-yl) | 4-CF$_3$ | 96-97 |
| 8-51 | CH(OMs)CH$_2$OMs | 4-CF$_3$ | 1.3084(22.8) |
| 8-52 | CH$_2$CH$_2$SMe | 4-CF$_3$ | 1.3713(25.6) |
| 8-53 | CH$_2$NHMe | 4-TMS | 1.5327(22.7) |
| 8-54 | CMe$_2$OH | 4-CF$_3$ | 90-91 |
| 8-55 | CH$_2$CH$_2$SOMe | 4-CF$_3$ | 1.3600(25.7) |
| 8-56 | CH$_2$CH$_2$SO$_2$Me | 4-CF$_3$ | 88-89 |
| 8-57 | (3-methylthio-4,5-dihydroisoxazol-5-yl) | 4-CF$_3$ | 1.3243(25.5) |
| 8-58 | Et | 4-(4-OCF$_3$—Ph) | 1.3208(26.4) |
| 8-59 | 3-F—Ph | 4-CF$_3$ | 99-100 |
| 8-60 | 4-F—Ph | 4-CF$_3$ | 59-61 |
| 8-61 | oxiranyl | 4-CF$_3$ | 1.3405(23.7) |
| 8-62 | CH(OCH$_2$OMe)CH$_2$OCH$_2$OMe | 4-CF$_3$ | 1.3199(23.6) |
| 8-63 | CMe$_2$OMe | 4-CF$_3$ | 78-79 |
| 8-64 | C≡C—n-Pr | 4-CF$_3$ | 32-34 |

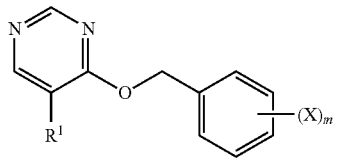

(I-3)

TABLE 9

| Comp. No. | R¹ | (X)ₘ | property value |
|---|---|---|---|
| 9-1 | 1,3-dioxan-2-yl | 4-i-Bu | 78-79 |
| 9-2 | 1,3-dioxan-2-yl | 4-s-Bu | NMR |
| 9-3 | 1,3-dioxan-2-yl | 2-F-4-CF₃ | 121-122 |
| 9-4 | 1,3-dioxan-2-yl | 4-OCF₂CF₂H | 87-88 |
| 9-5 | 1,3-dithian-2-yl | 4-CN | 154-158 |
| 9-6 | 1,3-dithian-2-yl | 4-NO₂ | 162-171 |
| 9-7 | imidazolin-2-yl | 4-OCF₃ | 104-105 |
| 9-8 | 1,3-dioxan-2-yl | 3-Cl-4-i-Pr | 1.3783(20.7) |
| 9-9 | 1,3-oxathian-2-yl | 4-t-Bu | 102-104 |
| 9-10 | 1,3-oxathian-2-yl | 4-CF₃ | 125-126 |
| 9-11 | 1,3-oxathian-2-yi | 4-OCF₃ | 118-120 |
| 9-12 | [structure] | 4-t-Bu | 212-215 |
| 9-13 | [structure] | 4-CF₃ | 226-230 |
| 9-14 | [structure] | 4-OCF₃ | 227-231 |
| 9-15 | [structure] | 4-t-Bu | 125-126 |
| 9-16 | [structure] | 4-OCF₃ | 86-89 |
| 9-17 | [structure] | 4-t-Bu | 139-140 |
| 9-18 | 2,2-dimethyl-1,3-dioxolan-4-yl | 4-t-Bu | 1.3345(24.4) |
| 9-19 | thiazolin-2-yl | 4-CF₃ | 91-92 |
| 9-20 | 1,3-dioxolan-2-yl | 2-F-4-CF₃ | 48-50 |
| 9-21 | 1,3-dioxepan-2-yl | 2-F-4-CF₃ | 114-115 |
| 9-22 | [structure] | 4-CF₃ | 109-110 |
| 9-23 | [structure] | 4-CF₃ | 158-160 |
| 9-24 | [structure] | 4-t-Bu | 97-100 |
| 9-25 | [structure] | 4-CF₃ | 155-177 |
| 9-26 | [structure] | 4-OCF₃ | 171-182 |
| 9-27 | [structure] | 4-CF₃ | 205-206 |
| 9-28 | [structure] | 4-OCF₃ | 194-195 |
| 9-29 | [structure] | 4-OCF₃ | 1.5117(22.4) |
| 9-30 | 1,3-dimethylimidazolidin-2-yl | 4-OCF₃ | 1.5084(22.3) |
| 9-31 | 4-ethyl-1,3-dioxolan-2-yl | 4-CF₃ | 32-33 |
| 9-32 | 4-methyl-1,3-dioxan-2-yl | 4-CF₃ | 98-100 |
| 9-33 | [structure] | 4-CF₃ | 67-69 |
| 9-34 | 1,1-(OMe)₂Et | 4-CF₃ | 120-122 |
| 9-35 | 1-(2-Me-1,3-dioxolan-2-yl) | 4-CF₃ | 64-65 |
| 9-36 | 1-(2-Me-1,3-dioxan-2-yl) | 4-CF₃ | 89-90 |

TABLE 9-continued

| Comp. No. | R¹ | (X)ₘ | property value |
|---|---|---|---|
| 9-37 | (3-acetyl-thiazolidin-4-one structure) | 4-OCF₃ | 119-121 |
| 9-38 | 4-methyl-1,3-dioxan-2-yl | 4-CF₃ | 112-120 |
| 9-39 | 2,2-dimethyl-1,3-dioxolan-4-yl | 4-CF₃ | 1.3314(22.5) |
| 9-40 | (bicyclic dioxa structure) | 4-t-Bu | 1.4558(27.2) |
| 9-41 | (spiro dioxolane-cyclohexane structure) | 4-CF₃ | 1.4058(25.8) |
| 9-42 | 1,3-dioxan-2-yl | 4-i-Pr | 63-68 |
| 9-43 | 1,3-dioxan-2-yl | 4-OCH₂CF₃ | 103-105 |
| 9-44 | 4-n-Pr-1,3-dioxolan-2-yl | 4-CF₃ | 1.3655(26.8) |
| 9-45 | 4-Me-1,3-dioxolan-2-yl | 4-CF₃ | 68-72 |
| 9-46 | (spiro dioxane-cyclopropane structure) | 4-CF₃ | 173-174 |
| 9-47 | (bicyclic dioxolane-furan structure) | 4-CF₃ | 140-145 |

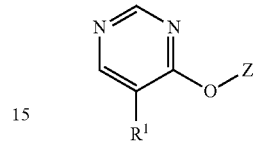

(I-4)

TABLE 10

| Comp. No. | R¹ | (X)ₘ | property value |
|---|---|---|---|
| 10-1 | n-Bu | 4-OCF₃ | 99-101 |
| 10-2 | 1,3-dioxan-2-yl | 4-OCF₃ | 145-147 |
| 10-3 | 3-Me—n-Bu | 4-OCF₃ | 88-99 |
| 10-4 | n-Pr | 4-OCF₃ | 86-87 |
| 10-5 | n-Pr | 4-CF₃ | 128-129 |
| 10-6 | n-Pr | 4-t-Bu | 54-55 |
| 10-7 | Et | 4-t-Bu | 143-144 |
| 10-8 | Et | 4-OCF₃ | 97-98 |
| 10-9 | i-Pr | 4-OCF₃ | 111-112 |

TABLE 10-continued

| Comp. No. | R¹ | (X)ₘ | property value |
|---|---|---|---|
| 10-10 | CH=CH₂ | 4-CF₃ | 136-139 |
| 10-11 | i-Bu | 4-t-Bu | 106 |

(I-5)

(pyrimidine-O-Z structure with R¹)

TABLE 11

| Comp. No. | R¹ | Z | property value |
|---|---|---|---|
| 11-1 | 1,3-dioxan-2-yl | -CH₂CH₂-C₆H₄-4-OCF₃ | 55-56 |
| 11-2 | n-Pr | -CH₂-(6-OCH₂CF₃-pyridin-3-yl) | 1.3420 (23.6) |
| 11-3 | 1,3-dioxan-2-yl | -CH₂CH₂-C₆H₄-4-OCF₃ | 45-46 |
| 11-4 | 1,3-dioxan-2-yl | -CH₂CH₂-C₆H₄-4-CF₃ | 69-71 |
| 11-5 | n-Pr | -CH₂-(6-Cl-pyridin-3-yl) | 29-30 |
| 11-6 | 1,3-dioxan-2-yl | -CH₂-(6-OCH₂CF₃-pyridin-3-yl) | 83-84 |

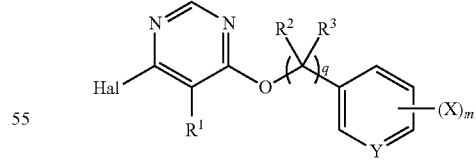

(II)

TABLE 12

(Hal = Cl, R², R³ = H, q = 1, Y = CH)

| Comp. No. | R¹ | (X)ₘ | property value |
|---|---|---|---|
| 12-1 | 1,3-dioxolan-2-yl | 4-t-Bu | 109-110 |
| 12-2 | 1,3-dioxolan-2-yl | 4-TMS | 104-105 |

TABLE 12-continued (Hal = Cl, $R^2$, $R^3$ = H, q = 1, Y = CH)

| Comp. No. | $R^1$ | $(X)_m$ | property value |
|---|---|---|---|
| 12-3 | 1,3-dithiolan-2-yl | 4-t-Bu | 95-102 |
| 12-4 | 1,3-dithiolan-2-yl | 4-CF$_3$ | 79-81 |
| 12-5 | 1,3-dithiolan-2-yl | 4-OCF$_3$ | 65-70 |
| 12-6 | 1,3-oxathian-2-yl | 4-t-Bu | 121-122 |
| 12-7 | 1,3-oxathian-2-yl | 4-CF$_3$ | 88-90 |
| 12-8 | 1,3-oxathian-2-yl | 4-OCF$_3$ | 61-62 |
| 12-9 | 1,3-dioxan-2-yl | 4-i-Bu | 1.3962(18.0) |
| 12-10 | 1,3-dioxan-2-yl | 2-F-4-CF$_3$ | 113-115 |
| 12-11 | 1,3-dioxan-2-yl | 4-OCF$_2$CF$_2$H | 105-106 |
| 12-12 | 1,3-dioxan-2-yl | 4-OCF$_3$ | 65-72 |
| 12-13 | 1,3-dithian-2-yl | 4-OCF$_3$ | 103-111 |
| 12-14 | 1,3-dithian-2-yl | 4-CN | 138-141 |
| 12-15 | 1,3-dithian-2-yl | 4-NO$_2$ | 147-150 |
| 12-16 | 1,3-dithian-2-yl | 4-t-Bu | 149-153 |
| 12-17 | 1,3-dithian-2-yl | 4-CF$_3$ | 114-122 |
| 12-18 | 1,3-oxathian-2-yl | 4-t-Bu | 98-100 |
| 12-19 | 1,3-oxathian-2-yl | 4-CF$_3$ | 118-119 |
| 12-20 | 1,3-oxathian-2-yl | 4-OCF$_3$ | 98 |
| 12-21 | CH(SEt)$_2$ | 4-t-Bu | 1.4087(21.3) |
| 12-22 | CH(SEt)$_2$ | 4-CF$_3$ | 1.4541(21.3) |
| 12-23 | CH(SEt)$_2$ | 4-OCF$_3$ | 1.4326(21.3) |
| 12-24 | CH(SMe)$_2$ | 4-t-Bu | 91-95 |
| 12-25 | CH(SMe)$_2$ | 4-CF$_3$ | 77-79 |
| 12-26 | CH(SMe)$_2$ | 4-OCF$_3$ | 51-54 |
| 12-27 | CHO | 4-CF$_3$ | 64-66 |
| 12-28 | CH=N—OH | 4-CF$_3$ | 182-184 |

TABLE 13

NMR data

| Comp. No. | $^1$H-NMR data |
|---|---|
| 8-10 | 9.24(1H, s), 8.89(1H, s), 8.74(1H, s), 8.51-8.47(1H, m), 7.57-7.50(1H, m), 7.46-7.39(4H, m), 7.35-7.30(1H, m), 5.54(2H, s), 1.33(9H, s) |
| 9-2 | 8.76(1H, s), 8.72(1H, s), 7.22-7.17(2H, m), 7.38-7.34(2H, m), 5.77(1H, s), 5.46(2H, s), 4.28-4.21(2H, m), 4.02-3.93(2H, m), 2.61(1H, tq), 2.31-2.17(1H, m), 1.60(dq, 2H), 1.48-1.41(1H, m), 1.24(3H, d), 0.84(3H, t) |
| 14-7 | 8.73(1H, s), 8.68(1H, d), 7.64(2H, d), 7.54(2H, d), 5.53(2H, dd), 5.10-5.07(1H, m), 4.75-4.68(1H, m), 3.61-3.34(4H, m), 1.32-1.24(3H, m), 1.18-1.17(3H, m) |
| 14-8 | 8.73(1H, s), 8.68(1H, d), 7.64(2H, d), 7.54(2H, d), 5.53(2H, dd), 5.10-5.07(1H, m), 4.40-4.37(1H, m), 3.88-3.84(1H, m), 3.59-3.49(1H, m), 3.27(3H, d), 1.63-1.53(2H, t), 1.26-1.24(1H, br), 0.89(3H, q) |
| 14-9 | 9.28(1H, s), 8.93(1H, s), 8.00(1H, s), 7.71-7.66(2H, m), 7.60-7.55(2H, m), 5.62(2H, s) |
| 14-12 | 8.61(1H, s), 8.50(1H, s), 7.65(2H, d), 7.56(2H, d), 6.51-6.38(2H, m), 5.55(2H, s), 2.30-2.23(2H, m), 1.10(3H, t) |
| 14-13 | 8.64(1H, s), 8.51(1H, s), 7.65(2H, d), 7.57(2H, d), 6.53-6.40(1H, m), 6.49(1H, d), 5.56(2H, s), 3.63(2H, t), 2.71(2H, dd) |
| 14-15 | 8.71(1H, s), 8.60(1H, s), 7.64(2H, d), 7.55(2H, d), 6.75(1H, d), 5.91(1H, dd), 5.52(2H, s), 5.37(1H, d), 4.08-4.05(2H, m), 3.93-3.90(2H, m) |
| 14-17 | 8.65(1H, s), 8.32(1H, s), 7.64(2H, d), 7.56(2H, d), 5.53(2H, s), 4.90(1H, t), 3.97-3.95(2H, m), 3.87-3.85(2H, m), 2.74(2H, dd), 2.00-1.96(2H, m) |
| 14-19 | 8.93(1H, s), 8.77(1H, s), 7.66(2H, d), 7.53(2H, d), 5.62(2H, dd), 5.55(1H, d), 1.55-1.48(1H, m), 0.90-0.78(2H, m), 0.70-0.64(1H, m), 0.47-0.41(1H, m) |

TABLE 13-continued

NMR data

| Comp. No. | $^1$H-NMR data |
|---|---|
| 14-28 | 9.01(1H, s), 8.84(1H, s), 7.66(2H, d), 7.52(2H, d), 5.63(2H, s), 5.32(1H, d), 3.72(3H, s), 2.89(1H, dd), 2.69(1H, dd), 1.75(1H, br) |
| 14-45 | 8.66(1H, s), 8.43(1H, s), 7.66(2H, d), 7.55(2H, d), 5.51(2H, s), 2.50(2H, d), 1.03-1.00(1H, m), 0.57-0.55(2H, m), 0.20(2H, dd) |
| 14-54 | 8.81(1H, s), 8.68(1H, s), 7.69-7.63(2H, m), 7.55-7.50(2H, m), 5.61(1H, d), 5.48(1H, d), 4.98(1H, q), 3.49(3H, s) |
| 14-56 | 8.70(1H, s), 8.35(1H, s), 7.63(2H, d), 7.50(2H, d), 5.56(2H, s), 3.57(3H, s), 1.68(2H, dd), 1.15(2H, dd) |
| 14-60 | 8.71(1H, s), 8.55(1H, s), 7.64(2H, d), 7.55(2H, d), 5.53(2H, s), 4.51(2H, s), 3.72(1H, sep), 1.23(6H, d) |
| 14-68 | 9.30(1H, s), 8.87(1H, s), 7.73-7.68(2H, m), 7.63-7.57(2H, m), 7.35-7.24(1H, m), 5.65(2H, s), 4.29-4.16(1H, m), 1.15(6H, d) |
| 14-69 | 9.29(1H, s), 8.86(1H, s), 7.73-7.68(2H, m), 7.64-7.58(2H, m), 7.40-7.30(1H, br), 5.61(2H, s), 1.33(9H, s) |
| 14-70 | 9.31(1H, s), 8.87(1H, s), 7.74-7.68(2H, m), 7.64-7.58(2H, m), 7.39(1H, d), 5.64(2H, s), 4.05-3.94(1H, m), 1.90-1.81(2H, m), 1.48-1.42(3H, m), 1.42-1.29(2H, m), 1.21-1.08(3H, m) |
| 14-71 | 8.80(1H, s), 8.54(1H, s), 7.67-7.60(2H, m), 7.57-7.50(2H, m), 5.58(2H, s), 3.65(2H, t), 3.24(2H, t), 2.20-1.91(2H, m), 1.91-1.83(2H, m) |
| 14-72 | 8.82(1H, s), 8.54(1H, s), 7.67-7.62(2H, m), 7.57-7.52(2H, m), 5.57(2H, s), 3.82-3.77(2H, m), 3.75-3.70(2H, m), 3.56-3.50(2H, m), 3.27-3.21(2H, m) |
| 14-73 | 9.22(1H, s), 8.77(1H, s), 7.94-7.83(2H, m), 7.62-7.57(2H, m), 7.57-7.51(2H, m), 5.58(2H, s), 3.42(2H, q), 2.33(2H, t), 2.01(6H, s) |
| 14-74 | 9.33(1H, s), 8.87(1H, s), 7.97-7.86(1H, br), 7.62-7.56(2H, m), 7.52-7.46(2H, m), 7.40-7.35(1H, m), 7.33-7.27(1H, m), 7.26-7.16(2H, m), 5.60(2H, s), 4.65(2H, d) |
| 14-75 | 9.34(1H, s), 8.89(1H, s), 7.80-7.65(1H, br), 7.60-7.54(2H, m), 7.46-7.41(2H, m), 7.30-7.27(3H, m), 7.12-7 06(1H, m), 5.61(2H, s), 4.56(2H, d) |
| 14-76 | 9.34(1H, s), 8.89(1H, s), 7.74-7.64(1H, br), 7.60-7.54(2H, m), 7.44-7.39(2H, m), 7.29-7.23(2H, m), 7.17-7.12(2H, m), 5.60(2H, s), 4.56(2H, d) |
| 14-77 | 9.25(1H, s), 8.76(1H, s), 7.83-7.73(1H, br), 7.50-7.44(2H, m), 7.38-7.32(2H, m), 7.23-7.14(2H, m), 6.84-6.78(1H, m), 6.73-6.68(1H, m), 5.53(2H, s), 4.52(2H, d), 3.51(3H, s) |
| 14-78 | 9.35(1H, s), 8.88(1H, s), 7.76-7.65(1H, br), 7.56-7.50(2H, m), 7.42-7.36(2H, m), 7.23-7.17(1H, m), 6.87-6.82(1H, m), 6.81-6.77(2H, m), 5.59(2H, s), 4.56(2H, d), 3.77(3H, s) |
| 14-79 | 9.35(1H, s), 8.87(1H, s), 7.67-7.59(1H, br), 7.56-7.50(2H, m), 7.40-7.35(2H, m), 7.17-7.12(2H, m), 6.85-6.80(2H, m), 5.57(2H, s), 4.52(2H, d), 3.80(3H, s) |
| 14-80 | 9.31(1H, s), 8.88(1H, s), 7.91 (1H, d), 7.67-7.61(2H, m), 7.56-7.51(2H, m), 7.34-7.29(1H, m), 7.22-7.09(3H, m), 5.69-5.51(3H, m), 1.48(3H, d) |
| 14-81 | 9.30(1H, s), 8.89(1H, s), 7.70 (1H, d), 7.68-7.63(2H, m), 7.55-7.50(2H, m), 7.25-7.15(3H, m), 7.10-7.05(2H, m), 5.65(1H, d), 5.59(1H, d), 5.22(1H, dq), 1.44(3H, d) |
| 14-82 | 9.30(1H, s), 8.88(1H, s), 7.70-7.63 (2H, m), 7.54-7.48(2H, m), 7.25-7.19(2H, m), 7.14-7.08(2H, m), 5.60(2H, s), 5.22(1H, dq), 1.43(3H, d) |
| 14-83 | 9.31(1H, s), 8.84(1H, s), 7.67-7.62 (2H, m), 7.47-7.35(3H, m), 7.24-7.19(2H, m), 7.10-7.04(2H, m), 5.57(2H, s), 3.70(2H, dt), 2.84(2H, t) |

TABLE 13-continued

NMR data

| Comp. No. | ¹H-NMR data |
|---|---|
| 14-84 | 9.31(1H, s), 8.82(1H, s), 7.64-7.58 (2H, m), 7.50-7.41(1H, br), 7.38-7.32(2H, m), 7.11-7.05(2H, m), 6.84-6.77(2H, m), 5.55(2H, s), 3.74(3H, s), 3.71(2H, dt), 2.82(2H, t) |
| 14-85 | 9.31(1H, s), 8.88(1H, s), 7.68-7.62 (2H, m), 7.59-7.54(2H, m), 7.46-7.37(1H, br), 7.24-7.18(2H, m), 7.04-6.97(2H, m), 5.65(2H, s), 3.43(2H, dt), 2.54(2H, t), 1.80(2H, tt) |
| 14-86 | 10.0-9.90(1H, br), 9.42(1H, s), 8.92(1H, s), 8.63-8.56(1H, m), 7.70-7.62(4H, m), 7.38-7.28(2H, m), 7.10-7.04(1H, m), 5.79(2H, s) |
| 14-87 | 9.38(1H, s), 9.36-9.30(1H, br), 8.94(1H, s), 7.79-7.74(2H, m), 7.70-7.65(2H, m), 7.49-7.45(1H, m), 7.23-7.18(2H, m), 7.13-7.05(1H, m), 5.71(2H, s) |
| 14-88 | 9.38(1H, s), 9.34-9.27(1H, br), 8.94(1H, s), 7.77-7.72(2H, m), 7.69-7.64(2H, m), 7.35-7.29(2H, m), 7.27-7.22(2H, m), 5.71(2H, s) |
| 14-89 | 9.87(1H, s), 9.46-9.37(1H, br), 8.94(1H, s), 8.60-8.54(1H, m), 7.70-7.66(2H, m), 7.66-7.61(2H, m), 7.36-7.34(1H, m), 7.30-7.25(1H, m), 5.78(2H, s) |
| 14-90 | 9.40-9.34(2H, m), 8.95(1H, s), 7.82-7.76(2H, m), 7.71-7.66(2H, m), 7.31-7.28(2H, m), 7.10-7.07(1H, m), 5.70(2H, s) |
| 14-91 | 8.66(1H, s), 8.45(1H, s), 7.69-7.62(2H, m), 7.53-7.45(2H, m), 7.18-7.10(1H, m), 7.10-6.98(1H, m), 6.89-6.76(1H, m), 5.37(2H, s), 3.43(3H, s) |
| 14-92 | 8.65(1H, s), 8.44(1H, s), 7.68-7.63(2H, m), 7.50-7.41(2H, m), 7.12-7.01(2H, m), 6.92-6.82(2H, m), 5.38(2H, s), 3.43(3H, s) |
| 14-93 | 10.0-9.90 (1H, br), 9.40(1H, s), 8.89(1H, s), 8.58-8.52(1H, m), 7.71-7.63(4H, m), 7.11-7.04(1H, m), 7.03-6.96(1H, m), 6.86-6.80(1H, m), 5.76(2H, s), 3.45(3H, s) |
| 14-94 | 9.37(1H, s), 9.33-9.26(1H, br), 8.92(1H, s), 7.77-7.71(2H, d), 7.70-7.65(2H, d), 7.20-7.13(1H, m), 7.13-7.10 (1H, m), 6.85-6.80(1H, m), 6.69-6.63(1H, m), 5.69(2H, s), 3.74(3H, s) |
| 14-95 | 9.38(1H, s), 9.24-9.15(1H, br), 8.91(1H, s), 7.76-7.70(2H, m), 7.68-7.62(2H, m), 7.35-7.28(2H, m), 6.86-6.79(2H, m), 5.70(2H, s), 3.78(3H, s) |
| 14-96 | 9.36(1H, s), 9.06-8.94(1H, br), 8.85(1H, s), 8.10-8.04(1H, m), 7.64-7.58(2H, m), 7.57-7.52(2H, m), 7.20-7.11(1H, m), 7.06-7.01(1H, m), 7.01-6.94(1H, m), 5.66(2H, s), 1.78(3H, s) |
| 14-97 | 9.39(1H, s), 9.33-9.22(1H, br), 8.92(1H, s), 7.78-7.72(2H, m), 7.71-7.65(2H, m), 7.30-7.23(2H, m), 7.21-7.14(2H, m), 7.11-7.06(1H, m), 6.96-6.90(1H, m), 5.69(2H, s), 2.28(3H, s) |
| 14-98 | 9.41(1H, s), 9.29-9.20(1H, br), 8.93(1H, s), 7.76-7.72(2H, m), 7.69-7.63(2H, m), 7.31-7.26(2H, m), 7.14-7.08(2H, m), 5.71(2H, s), 2.32(3H, s) |
| 14-99 | 9.39(1H, s), 9.29-9.21(1H, br), 8.92(1H, s), 7.75-7.70(2H, m), 7.68-7.62(2H, m), 7.38-7.33(2H, m), 7.16-7.10(2H, m), 6.96-6.91(2H, m), 6.91-6.86(2H, m), 5.72(2H, s), 2.33(3H, s) |
| 14-100 | 9.39(1H, s), 9.32-9.25(1H, br), 8.93(1H, s), 7.76-7.71(2H, m), 7.69-7.64(2H, m), 7.41-7.35(2H, m), 7.30-7.24(2H, m), 6.98-6.93(2H, m), 6.93-6.88(2H, m), 5.73(2H, s) |
| 14-101 | 9.35 (1H, s), 8.89(1H, s), 7.74-7.66(1H, br), 7.60-7.55(2H, m), 7.46-7.40(1H, m), 7.29-7.25(2H, m), 7.23-7.18(2H, m), 7.02-6.91(4H, m), 5.61(2H, s), 4.58(2H, d) |
| 14-110 | 8.72(1H, s), 8.43(1H, s), 7.65(2H, d), 7.55(2H, d), 5.52(2H, s), 4.39(2H, s), 2.80(3H, s), 2.78(3H, s) |
| 14-111* | 8.73(1H, s), 8.45(1H, bs), 7.65(2H, d), 7.55(2H, d), 5.53(2H, s), 4.48(2H, bs), 3.75(3H, bs), 2.91(3H, bs) 8.73(1H, s), 8.39(1H, bs), 7.65(2H, d), 7.55(2H, d), 5.53(2H, s), 4.43(2H, bs), 3.66(3H, bs), 2.95(3H, bs) |
| 15-5 | 8.74(1H, s), 8.66(1H, s), 7.55(1H, d), 7.45(1H, d), 7.28(1H, dd), 5.58(1H, s), 5.46(2H, s), 4.67(1H, d), 3.37(6H, s) |
| 15-72 | 8.78(1H, s), 8.71(1H, s), 7.66-7.62(2H, m), 7.59-7.53(2H, m), 6.09(1H, s), 5.57(2H, s), 4.51-4.44(1H, m), 4.24(1H, dd), 4.19(1H, dd), 4.14(1H, dd), 3.96(1H, dd), 2.08(3H, s) |
| 15-73 | 8.77(1H, s), 8.63(1H, s), 7.67-7.62(2H, m), 7.59-7.53(2H, m), 6.20(1H, s), 5.57(2H, s), 4.54-4.48(1H, m), 4.28-4.22(3H, m), 3.83(1H, dd), 2.10(3H, s) |
| 15-90 | 8.74(1H, s), 8.65(1H, s), 7.65(2H, d), 7.52(2H, d), 5.53(2H, dd) 5.22-5.18(2H, m), 4.23 (1H, dd), 3.82(1H, dd), 1.55(3H, s) |
| 15-91 | 8.73(1H, s), 8.66(1H, s), 7.64(2H, d), 7.52(2H, d), 5.55(2H, dd), 5.22(1H, t), 5.02 (1H, t), 4.44(1H, dd), 3.78(1H, dd), 1.86-1.75(2H, m), 1.07-1.01(3H, m) |
| 15-92 | 8.74-8.59(2H, m), 7.64(2H, d), 7.53(2H, d), 5.60-5.53(2H, m), 5.19-5.05(1H, m), 4.35-4.31(1H, m), 3.78-3.35(2H, m), 1.68-1.57(2H, m), 0.92-0.79(2H, m) |
| 15-112 | 8.80(1H, s), 8.69(1H, s), 7.65(2H, d), 7.54(2H, d), 6.07(1H, s), 5.57(2H, s), 4.08-3.99 (4H, m) |

*mixture of two kinds of rotamers

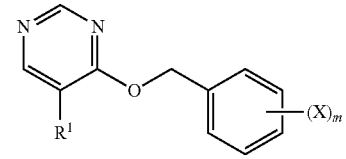

(I-3)

TABLE 14

| Comp. No. | R¹ | (X)$_m$ | property value |
|---|---|---|---|
| 14-1 | CH=C(CN)CO₂Me | 4-CF₃ | 125-131 |
| 14-2 | CH₂CH₂SEt | 4-CF₃ | 1.3286(21.8) |
| 14-3 | CH₂CH₂CH₂SMe | 4-OCF₃ | 1.3081(27.8) |
| 14-4 | CH₂CO₂Me | 4-CF₃ | 1.5082(27.6) |
| 14-5 | CH₂CH₂CH₂Cl | 4-CF₃ | 1.5038(24.9) |
| 14-6 | CH₂CO₂H | 4-CF₃ | 175-180 |
| 14-7 | CH(OH)CH₂OCH(OEt)Me | 4-CF₃ | NMR |
| 14-8 | CH(OH)CH₂OCH(OMe)Et | 4-CF₃ | NMR |
| 14-9 | CH=C(CN)₂ | 4-CF₃ | NMR |
| 14-10 | CH=c-Pr | 4-CF₃ | 53-56 |
| 14-11 | CH(OH)c-Pr | 4-CF₃ | 1.3532(25.8) |
| 14-12 | CH=CHEt | 4-CF₃ | NMR |
| 14-13 | CH=CHCH₂CH₂Cl | 4-CF₃ | NMR |
| 14-14 | CH(OMe)c-Pr | 4-CF₃ | 1.4978(25.7) |
| 14-15 | CH=C-(1,3-dioxolan-2-yl) | 4-CF₃ | NMR |
| 14-16 | CH=C-(1,3-dioxolan-2-yl) | 4-CF₃ | 70-74 |
| 14-17 | CH₂CH₂-(1,3-dioxolan-2-yl) | 4-CF₃ | NMR |
| 14-18 | CH=CHCH₂CH₂OCOCF₃ | 4-CF₃ | 1.3688(25.1) |
| 14-19 | CH(OCOCF₃)—c-Pr | 4-CF₃ | NMR |
| 14-20 | CO—c-Pr | 4-CF₃ | 91-92 |
| 14-21 | CH(OH)CH₂CO₂Me | 4-CF₃ | 88-90 |
| 14-22 | CH(OH)CH₂CO₂H | 4-CF₃ | 144-145 |
| 14-23 | CH=C(CO₂Me)₂ | 4-CF₃ | 1.4172(24.3) |
| 14-24 | (2,2-(CO₂Me)₂)—c-Pr | 4-CF₃ | 84-87 |
| 14-25 | CH₂Cl | 4-CF₃ | 82-85 |
| 14-26 | CH₂CH(CO₂Me)₂ | 4-CF₃ | 70-71 |
| 14-27 | CH=CHCOMe | 4-CF₃ | 95-98 |

TABLE 14-continued

| Comp. No. | R¹ | (X)$_m$ | property value |
|---|---|---|---|
| 14-28 | CH(OH)CH$_2$CO$_2$Me | 4-CF$_3$ | NMR |
| 14-29 | CH$_2$-(pyrrolidin-1-yl) | 4-CF$_3$ | 1.5172(22.2) |
| 14-30 | CH$_2$NHCOEt | 4-CF$_3$ | 123-124 |
| 14-31 | CH$_2$NHCOCH$_2$CH$_2$CH$_2$Cl | 4-CF$_3$ | 84-88 |
| 14-32 | 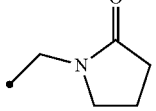 | 4-CF$_3$ | 1.5215(18.8) |
| 14-33 | 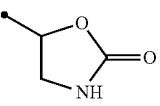 | 4-CF$_3$ | 129-132 |
| 14-34 | CH(OH)CF$_3$ | 4-CF$_3$ | 132-134 |
| 14-35 | C(OH)$_2$CF$_3$ | 4-CF$_3$ | 75-79 |
| 14-36 | 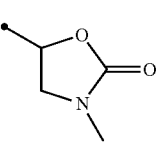 | 4-CF$_3$ | 143-144 |
| 14-37 | CH$_2$NHMe | 4-CF$_3$ | 1.5020(22.5) |
| 14-38 | CH$_2$N(Me)COMe | 4-CF$_3$ | 101-102 |
| 14-39 | CH$_2$NHPh | 4-CF$_3$ | 1.5641(21.4) |
| 14-40 | CH$_2$N(Ph)COMe | 4-CF$_3$ | 1.5396(21.3) |
| 14-41 | CH$_2$N(Ph)COCF$_3$ | 4-CF$_3$ | 1.5173(21.7) |
| 14-42 | CH$_2$NH—c-Pr | 4-CF$_3$ | 1.5132(21.4) |
| 14-43 | CH$_2$-(piperidin-1-yl) | 4-CF$_3$ | 1.5098(21.6) |
| 14-44 | CHMe=CH$_2$ | 4-CF$_3$ | 1.4006(21.1) |
| 14-45 | CH$_2$—c-Pr | 4-CF$_3$ | NMR |
| 14-46 | CONH(CH$_2$-(4-F—Ph)) | 4-CF$_3$ | 107-108 |
| 14-47 | CH=CMe$_2$ | 4-CF$_3$ | 1.4781(21.4) |
| 14-48 | CH=CHMe | 4-CF$_3$ | 1.4537(21.6) |
| 14-49 | CH$_2$NEt$_2$ | 4-CF$_3$ | 1.4973(21.5) |
| 14-50 | CH$_2$NHCH$_2$CF$_3$ | 4-CF$_3$ | 1.4815(21.5) |
| 14-51 | 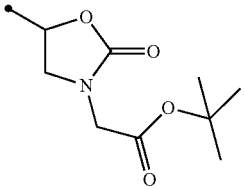 | 4-CF$_3$ | 95-96 |
| 14-52 | CBr=CH$_2$ | 4-CF$_3$ | 1.3921(21.4) |
| 14-53 | c-Pr-(1-CO$_2$Me) | 4-CF$_3$ | NMR |
| 14-54 | CH$_2$OEt | 4-CF$_3$ | 1.4027(21.7) |
| 14-55 | CMe$_2$CO$_2$Me | 4-CF$_3$ | 1.4679(20.5) |
| 14-56 | CH(OMe)CF$_3$ | 4-CF$_3$ | NMR |
| 14-57 | CH$_2$SEt | 4-CF$_3$ | 1.5173(20.9) |
| 14-58 | CH$_2$SOEt | 4-CF$_3$ | 70-71 |
| 14-59 | CH$_2$SO$_2$Et | 4-CF$_3$ | 77-78 |
| 14-60 | CH$_2$O—i-Pr | 4-CF$_3$ | NMR |
| 14-61 | CH$_2$N(CH$_2$CF$_3$)COMe | 4-CF$_3$ | 1.4869(21.2) |
| 14-62 | CH=CHCO$_2$Me | 4-CF$_3$ | 93-96 |
| 14-63 | CH—CHCN | 4-CF$_3$ | 88-91 |
| 14-64 | CH=CHCN | 4-CF$_3$ | 70-72 |
| 14-65 | CH$_2$CN | 4-CF$_3$ | 88-89 |
| 14-66 | C(=CH$_2$)C=CTMS | 4-CF$_3$ | 52-54 |
| 14-67 | CH$_2$S(=NCN)Et | 4-CF$_3$ | 1.3767(21.9) |
| 14-68 | CONH—i-Pr | 4-CF$_3$ | NMR |
| 14-69 | CONH—t-Bu | 4-CF$_3$ | NMR |
| 14-70 | CONH—c-Hex | 4-CF$_3$ | NMR |
| 14-71 | CO-(pyrrolidin-1-yl) | 4-CF$_3$ | NMR |
| 14-72 | CO-(morpholin-1-yl) | 4-CF$_3$ | NMR |
| 14-73 | CONHCH$_2$CH$_2$NMe$_2$ | 4-CF$_3$ | NMR |
| 14-74 | CONH(CH$_2$-(2-Cl—Ph)) | 4-CF$_3$ | NMR |
| 14-75 | CONH(CH$_2$-(3-Cl—Ph)) | 4-CF$_3$ | NMR |
| 14-76 | CONH(CH$_2$-(4-Cl—Ph)) | 4-CF$_3$ | NMR |
| 14-77 | CONH(CH$_2$-(2-OMe—Ph)) | 4-CF$_3$ | NMR |
| 14-78 | CONH(CH$_2$-(3-OMe—Ph)) | 4-CF$_3$ | NMR |
| 14-79 | CONH(CH$_2$-(4-OMe—Ph)) | 4-CF$_3$ | NMR |
| 14-80 | CONH(CHMe-(2-Cl—Ph)) | 4-CF$_3$ | NMR |
| 14-81 | CONH(CHMe-(3-Cl—Ph)) | 4-CF$_3$ | NMR |
| 14-82 | CONH(CHMe-(4-Cl—Ph)) | 4-CF$_3$ | NMR |
| 14-83 | CONH(CH$_2$CH$_2$-(4-Cl—Ph)) | 4-CF$_3$ | NMR |
| 14-84 | CONH(CH$_2$CH$_2$-(4-OMe—Ph)) | 4-CF$_3$ | NMR |
| 14-85 | CONH(CH$_2$CH$_2$CH$_2$-(4-Cl—Ph)) | 4-CF$_3$ | NMR |
| 14-86 | CONH-(2-Cl—Ph) | 4-CF$_3$ | NMR |
| 14-87 | CONH-(3-Cl—Ph) | 4-CF$_3$ | NMR |
| 14-88 | CONH-(4-Cl—Ph) | 4-CF$_3$ | NMR |
| 14-89 | CONH-(2,4-Cl$_2$—Ph) | 4-CF$_3$ | NMR |
| 14-90 | CONH-(3,5-Cl$_2$—Ph) | 4-CF$_3$ | NMR |
| 14-91 | CON(Me)(3-Cl—Ph) | 4-CF$_3$ | NMR |
| 14-92 | CON(Me)(4-Cl—Ph) | 4-CF$_3$ | NMR |
| 14-93 | CONH-(2-OMe—Ph) | 4-CF$_3$ | NMR |
| 14-94 | CONH-(3-OMe—Ph) | 4-CF$_3$ | NMR |
| 14-95 | CONH-(4-OMe—Ph) | 4-CF$_3$ | NMR |
| 14-96 | CONH-(2-Me—Ph) | 4-CF$_3$ | NMR |
| 14-97 | CONH-(3-Me—Ph) | 4-CF$_3$ | NMR |
| 14-98 | CONH-(4-Me—Ph) | 4-CF$_3$ | NMR |
| 14-99 | CONH-(4-(4-Me—PhO)—Ph) | 4-CF$_3$ | NMR |
| 14-100 | CONH-(4-(4-Cl—PhO)—Ph) | 4-CF$_3$ | NMR |
| 14-101 | CONH-(CH$_2$-(4-(4-OCF$_3$—PhO)—Ph)) | 4-CF$_3$ | NMR |
| 14-102 | c-Pr-(2-CO$_2$Me) | 4-CF$_3$ | 112-114 |
| 14-103 | C(OH)(OMe)CF$_3$ | 4-CF$_3$ | 62-65 |
| 14-104 | Et | 4-CF(CF$_3$)$_2$ | 1.4578(20.1) |
| 14-105 | Et | 4-SCF$_3$ | 43-44 |
| 14-106 | c-Pr-(1-CN) | 4-CF$_3$ | 119-121 |
| 14-107 | CH$_2$S(=NCOCF$_3$)Et | 4-CF$_3$ | 127-129 |
| 14-108 | CH$_2$N(Me)(CO—c-Pr) | 4-CF$_3$ | 1.5280(20.7) |
| 14-109 | CH$_2$N(Me)(SO$_2$Me) | 4-CF$_3$ | 94-96 |
| 14-110 | CH$_2$N(Me)(CONMe$_2$) | 4-CF$_3$ | NMR |
| 14-111 | CH$_2$N(Me)(CO$_2$Me) | 4-CF$_3$ | NMR |
| 14-112 | CH$_2$N(Me)(CO—i-Pr) | 4-CF$_3$ | 1.4311(20.7) |
| 14-113 | CH$_2$N(Me)(CO—n-Pr) | 4-CF$_3$ | 1.4300(20.7) |
| 14-114 | CH$_2$NH(CO—i-Pr) | 4-CF$_3$ | 155-165 |
| 14-115 | CH$_2$NH(CO—n-Pr) | 4-CF$_3$ | 80-85 |
| 14-116 | CH$_2$N(n-Pr)$_2$ | 4-CF$_3$ | 1.4974(21.9) |
| 14-117 | c-Pr | 4-CF(CF$_3$)$_2$ | 1.4050(21.4) |
| 14-118 | c-Pr | 4-CF$_2$CF$_3$ | 1.5002(21.4) |
| 14-119 | c-Pr | 4-Cl | 38-40 |
| 14-120 | c-Pr | 4-Br | 40-41 |
| 14-121 | c-Pr | 2-F-4-CF$_3$ | 1.4920(21.4) |
| 14-122 | Et | 4-CH$_2$CF$_3$ | 66-68 |
| 14-123 | CMe$_2$CN | 4-CF$_3$ | 58-59 |

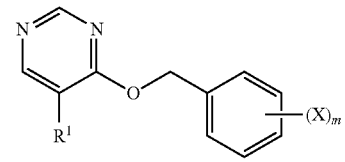

(I-3)

TABLE 15

| Comp. No. | R¹ | (X)$_m$ | property value |
|---|---|---|---|
| 15-1 | CH(OMe)$_2$ | 4-Br | 1.4476(25.2) |
| 15-2 | CH(OMe)$_2$ | 4-I | 1.4313(25.4) |
| 15-3 | CH(OMe)$_2$ | 4-F | 1.4741(23.5) |
| 15-4 | CH(OMe)$_2$ | 4-Cl | 1.4752(23.4) |
| 15-5 | CH(OMe)$_2$ | 3,4-Cl$_2$ | NMR |
| 15-6 | CH(OMe)$_2$ | 2,4-Cl$_2$ | 50-51 |
| 15-7 | CH(OMe)$_2$ | 2,4-F$_2$ | 59-60 |

TABLE 15-continued

| Comp. No. | R¹ | (X)$_m$ | property value |
|---|---|---|---|
| 15-8 | CH(OMe)$_2$ | 3,4-F$_2$ | 1.5038(18.5) |
| 15-9 | 4-Me-1,3-dioxolan-2-yl | 4-Br | 72-74 |
| 15-10 | 4-Me-1,3-dioxolan-2-yl | 4-Br | 1.3813(23.4) |
| 15-11 | 4-Me-1,3-dioxolan-2-yl | 4-I | 1.4034(23.3) |
| 15-12 | 4-Me-1,3-dioxolan-2-yl | 4-I | 1.4433(23.3) |
| 15-13 | 4-Me-1,3-dioxolan-2-yl | 4-t-Bu | 1.5201(26.7) |
| 15-14 | 4-Me-1,3-dioxolan-2-yl | 4-OCF$_3$ | 1.4885(26.7) |
| 15-15 | 4-Me-1,3-dioxolan-2-yl | 4-F | 1.4648(26.7) |
| 15-16 | 4-Me-1,3-dioxolan-2-yl | 4-Cl | 1.4316(26.7) |
| 15-17 | 4-Me-1,3-dioxolan-2-yl | 3,4-Cl$_2$ | 1.4264(26.7) |
| 15-18 | 4-Me-1,3-dioxolan-2-yl | 3,4-F$_2$ | 1.4627(26.7) |
| 15-19 | 4-Me-1,3-dioxolan-2-yl | 2,4-F$_2$ | 1.4989(26.7) |
| 15-20 | 1,3-dioxan-2-yl | 4-Me | 94-95 |
| 15-21 | 1,3-dioxan-2-yl | 4-F | 94-95 |
| 15-22 | 1,3-dioxan-2-yl | 4-Br | 114-116 |
| 15-23 | 1,3-dioxan-2-yl | 4-OMe | 1.5553(25.3) |
| 15-24 | 1,3-dioxan-2-yl | 4-SMe | 1.4365(25.1) |
| 15-25 | 1,3-dioxan-2-yl | 4-Et | 1.4075(24.5) |
| 15-26 | 1,3-dioxan-2-yl | 4-OEt | 67-69 |
| 15-27 | 1,3-dioxan-2-yl | 4-NO$_2$ | 175-179 |
| 15-28 | 1,3-dioxan-2-yl | 3,4-Cl$_2$ | 141-145 |
| 15-29 | 1,3-dioxan-2-yl | 2,4-Cl$_2$ | 147-149 |
| 15-30 | 1,3-dioxan-2-yl | 3,4-F$_2$ | 145-149 |
| 15-31 | 1,3-dioxan-2-yl | 2,4-F$_2$ | 110-111 |
| 15-32 | 1,3-dioxan-2-yl | 2-Br | 107-110 |
| 15-33 | 1,3-dioxan-2-yl | 3-CF$_3$ | 85-90 |
| 15-34 | 1,3-dioxan-2-yl | 4-I | 133-135 |
| 15-35 | 1,3-dioxan-2-yl | 2-F-4-Cl | 139-140 |
| 15-36 | 1,3-dioxan-2-yl | 4-OCHF$_2$ | 87-88 |
| 15-37 | 1,3-dioxan-2-yl | 2-Cl-4-F | 117-118 |
| 15-38 | 1,3-dioxan-2-yl | 2-Cl-4-Br | 141-142 |
| 15-39 | 1,3-dioxan-2-yl | 2-F-4-Br | 133-134 |
| 15-40 | 1,3-dioxan-2-yl | 4-CF(CF$_3$)$_2$ | 130-131 |
| 15-41 | 1,3-dioxan-2-yl | 3-F-4-CF$_3$ | 166-167 |
| 15-42 | 1,3-dioxan-2-yl | 3-Br | 109-111 |
| 15-43 | 1,3-dioxan-2-yl | 2-CF$_3$ | 93-94 |
| 15-44 | 1,3-dioxan-2-yl | 2,5-Cl$_2$ | 170-172 |
| 15-45 | 1,3-dioxan-2-yl | 2,6-Cl$_2$ | 119-121 |
| 15-46 | 1,3-dioxan-2-yl | 2-F-5-CF$_3$ | 96-97 |
| 15-47 | 1,3-dioxan-2-yl | 4-CHF$_2$ | 105-106 |
| 15-48 | 1,3-dioxan-2-yl | 4-CF$_2$CF$_2$CF$_3$ | 99-100 |
| 15-49 | 1,3-dioxan-2-yl | 4-COMe(CF$_3$)$_2$ | 142-147 |
| 15-50 | 1,3-dioxan-2-yl | 4-(4-SCF$_3$—Ph) | 103-104 |
| 15-51 | 1,3-dioxan-2-yl | 4-(4-OCF$_3$—Ph) | 72-75 |
| 15-52 | 1,3-dioxan-2-yl | 4-CF$_2$CF$_3$ | 105-107 |
| 15-53 | 1,3-dioxan-2-yl | 4-OCF$_2$CHFCF$_3$ | 49-50 |
| 15-54 | 1,3-dioxan-2-yl | 4-SCF$_2$CF$_3$ | 129-130 |
| 15-55 | 1,3-dioxan-2-yl | 4-(3-CF$_3$—Ph) | 117-118 |
| 15-56 | 1,3-dioxan-2-yl | 4-(2-CF$_3$—Ph) | 71-72 |
| 15-57 | 1,3-dioxan-2-yl | 4-(4-OCF$_3$—PhO) | 1.3391(21.0) |
| 15-58 | 1,3-dioxan-2-yl | 4-CH$_2$Cl | 139-140 |
| 15-59 | 1,3-dioxan-2-yl | 4-OCF$_2$CHFOCF$_3$ | 64-66 |
| 15-60 | 1,3-dioxan-2-yl | 4-CF$_3$ | 1.4924(27.4) |
| 15-61 | 1,3-dioxan-2-yl | 4-Br | 1.4364(25.2) |
| 15-62 | 1,3-dioxepan-2-yl | 4-CF$_3$ | 39-41 |
| 15-63 | 1,3-dioxolan-2-yl | 4-CF$_3$ | 1.3338(24.8) |
| 15-64 | 1,3-dioxepan-2-yl | 4-Br | 56-61 |
| 15-65 | 1,3-dioxepan-2-yl | 4-I | 91-94 |
| 15-66 | 1,3-dioxepan-2-yl | 4-F | 85-90 |
| 15-67 | 1,3-dioxepan-2-yl | 4-Cl | 85-87 |
| 15-68 | 1,3-dioxepan-2-yl | 2,4-F$_2$ | 133-134 |
| 15-69 | 1,3-dioxepan-2-yl | 3,4-F$_2$ | 108-111 |
| 15-70 | 1,3-dioxepan-2-yl | 3,4-Cl$_2$ | 124-125 |
| 15-71 | 1,3-dioxepan-2-yl | 2,4-Cl$_2$ | 120-122 |
| 15-72 | (4-CH$_2$OCOMe)-1,3-dioxolan-2-yl | 4-CF$_3$ | NMR |
| 15-73 | (4-CH$_2$OCOMe)-1,3-dioxolan-2-yl | 4-CF$_3$ | NMR |
| 15-74 | 4-Ph-1,3-dioxolan-2-yl | 4-CF$_3$ | 1.3289(25.6) |
| 15-75 | (4-CH$_2$OMe)-1,3-dioxolan-2-yl | 4-CF$_3$ | 1.4392(25.6) |
| 15-76 | (4,4,5,5-Me$_4$)-1,3-dioxolan-2-yl | 4-CF$_3$ | 1.3793(25.4) |
| 15-77 | (4-CH$_2$Cl)-1,3-dioxolan-2-yl | 4-CF$_3$ | 86-88 |
| 15-78 | (4-CH$_2$Cl)-1,3-dioxolan-2-yl | 4-CF$_3$ | 1.4772(25.7) |
| 15-79 | (4-CH$_2$OH)-1,3-dioxolan-2-yl | 4-CF$_3$ | 85-87 |
| 15-80 | (4-CH$_2$OH)-1,3-dioxolan-2-yl | 4-CF$_3$ | 110-113 |
| 15-81 | (4-CH$_2$OCH$_2$CH=CH$_2$)-1,3-dioxolan-2-yl | 4-CF$_3$ | 1.4660(25.5) |
| 15-82 | (4-CH$_2$OPh)-1,3-dioxolan-2-yl | 4-CF$_3$ | 40-42 |
| 15-83 | (4-CH$_2$OPh)-1,3-dioxolan-2-yl | 4-CF$_3$ | 69-70 |
| 15-84 | (4-CH=CH$_2$)-1,3-dioxolan-2-yl | 4-CF$_3$ | 1.4984(25.6) |
| 15-85 | [bicyclic structure] | 4-CF$_3$ | 76-77 |
| 15-86 | (4,5-(CH$_2$Cl)$_2$)-1,3-dioxolan-2-yl | 4-CF$_3$ | 76-79 |
| 15-87 | (4-CH$_2$F)-1,3-dioxolan-2-yl | 4-CF$_3$ | 80-83 |
| 15-88 | (4-CH$_2$F)-1,3-dioxolan-2-yl | 4-CF$_3$ | 70-72 |
| 15-89 | (4-CH$_2$SO$_2$Me)-1,3-dioxolan-2-yl | 4-CF$_3$ | 98-101 |
| 15-90 | (2-Me)-1,3-dioxolan-4-yl | 4-CF$_3$ | NMR |
| 15-91 | (2-Et)-1,3-dioxolan-4-yl | 4-CF$_3$ | NMR |
| 15-92 | (2-Et)-1,3-dioxolan-4-yl | 4-CF$_3$ | NMR |
| 15-93 | (2-Ph)-1,3-dioxolan-4-yl | 4-CF$_3$ | 1.5144(25.5) |
| 15-94 | (2-Ph)-1,3-dioxolan-4-yl | 4-CF$_3$ | 1.5054(25.4) |
| 15-95 | [cyclic structure] | 4-CF$_3$ | 130-137 |
| 15-96 | [spiro structure] | 4-CF$_3$ | 147-150 |
| 15-97 | (4,4-Me$_2$)-1,3-dioxan-2-yl | 4-CF$_3$ | 78-81 |
| 15-98 | (4,4,6-Me$_3$)-1,3-dioxan-2-yl | 4-CF$_3$ | 137-138 |
| 15-99 | (4,4,6,6-Me$_4$)-1,3-dioxan-2-yl | 4-CF$_3$ | 128-130 |
| 15-100 | [benzodioxin structure] | 4-CF$_3$ | 91-93 |
| 15-101 | (5-Me)-(5-CH$_2$OH)-1,3-dioxan-2-yl | 4-CF$_3$ | 143-145 |
| 15-102 | (5-Me)-(5-CH$_2$OH)-1,3-dioxan-3-yl | 4-CF$_3$ | 149-151 |
| 15-103 | (5-Ph)-1,3-dioxan-2-yl | 4-CF$_3$ | 152-155 |
| 15-104 | (5-CH$_2$OH)-1,3-dioxan-2-yl | 4-CF$_3$ | 186-187 |
| 15-105 | (5-CH$_2$OH)-1,3-dioxan-2-yl | 4-CF$_3$ | 160-162 |
| 15-106 | [bicyclic structure] | 4-CF$_3$ | 1.5074(25.1) |
| 15-107 | (5-CH$_2$OSO$_2$Me)-1,3-dioxan-2-yl | 4-CF$_3$ | 114-116 |
| 15-108 | [spiro dithiolane structure] | 4-CF$_3$ | 172-175 |
| 15-109 | (5-CH$_2$F)-1,3-dioxan-2-yl | 4-CF$_3$ | 115-117 |
| 15-110 | (4-CF$_3$)-1,3-dioxan-2-yl | 4-CF$_3$ | 122-124 |
| 15-111 | (5,5-F$_2$)-1,3-dioxan-2-yl | 4-CF$_3$ | 153-156 |
| 15-112 | (5,5,6,6-F$_4$)-1,3-dioxepan-2-yl | 4-CF$_3$ | NMR |

TABLE 15-continued

| Comp. No. | R¹ | (X)$_m$ | property value |
|---|---|---|---|
| 15-113 | 1,3-dioxepan-2-yl | 4-CF(CF$_3$)$_2$ | 78-79 |
| 15-114 | CH(OMe)$_2$ | 4-CF(CF$_3$)$_2$ | 48-49 |

The agrohorticultural insecticides containing the arylalkyloxypyrimidine derivative represented by the formula (I) or salts thereof of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers and ornamental plants, etc.

Examples of the above-mentioned noxious insect, nematodes and the like include the following.

Examples of the insect pest of Lepidoptera include *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura, Eucosma aporema, Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis Loparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicate, Archips fuscocupreanus, Acanthoplusia agnata, Bambalina sp., Carposina niponensis, Conogethes punctiferalis, Synanthedon sp., Lyonetia clerkella, Papilio helenus, Colias erate poliographus, Phalera flavescens*, Pieridae such as *Pieris rapae crucivora, Pieris rapae* and the like, *Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens, Earias cupreoviridis* and the like.

Examples of the noxious insect pest of Hemiptera include *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissusleucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzusmumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleate, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsianarosae, Pinnaspisaspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca* sp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisi-* coccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens, Aphis gossypii and the like.

Examples of the insect pest of Coleoptera include *Xystrocera globosa, Paederus fuscipes, Eucetonia roelofsi, Callosobruchus chinensis, Cylas formicarius, Hypera postica, Echinocnemus squameus, Oulema oryzae, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomolpha tunebrosa, Phyllotreta striolata, Psacothea hilaris, Aeolesthes chrysothrix, Curculio sikkimensis, Carpophilus hemipterus, Oxycetonia jucunda, Diabrotica spp., Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes spp., Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea, Anthonomus grandis* and the like.

Examples of the insect pest of Diptera include *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans*, Phoridae such as *Megaselia spiracularis* and the like, *Clogmia albipunctata, Tipula aino, Phormia regina, Culex tritaeniorhynchus, Anopheles sinensis, Hylemya brassicae, Asphondylia sp., Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens, Rhagoletis pomonella* and the like.

Examples of the insect pest of Hymenoptera include *Pristomyrmex pungens*, Bethylidae, *Monomorium pharaohnis, Pheidole noda, Athalia rosae, Dryocosmus kuriphilus, Formica fusca japonica*, Vespoidea, *Athalia infumata infumata, Arge pagana, Athalia japonica, Acromyrmex* spp., *Solenopsis* spp., *Arge mali, Ochetellus glaber* and the like.

Examples of the insect pest of Orthoptera include *Homorocoryphus lineosus, Gryllotalpa* sp., *Oxya hyla intricata, Oxya yezoensis, Locusta migratoria, Oxya japonica, Homorocoryphus jezoensis, Teleogryllus emma* and the like.

Examples of the insect pest of Thripidae include *Selenothrips rubrocinctus, Stenchaetothrips biformis, Haplothrips aculeates, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora, Liothrips vaneeckei* and the like.

Examples of the pest of Acari include *Leptotrombidium akamushi, Tetranychus ludeni, Dermacentor variabilis, Tetranychus truncatus, Ornithonyssus bacoti, Demodex canis, Tetranychus viennensis, Tetranychus kanzawai*, Ixodes such as *Rhipicephalus sanguineus* and the like, *Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini, Sancassania* sp. and the like.

Examples of the pest of Termitidaenoxious include *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapriterrmes nitobei, Reticulitermes speratus* and the like.

Examples of the insect pest of Blattaria include *Periplaneta fuliginosa, Blattella germanica, Blatta orientalis, Periplaneta brunnea, Blattella lituricollis, Periplaneta japonica, Periplaneta americana* and the like.

Examples of the Aphaniptera include *Pulex irritans, Ctenocephalides felis, Ceratophyllus gallinae* and the like.

Examples of the Nematoda include *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus, Tylenchus semipenetrans* and the like.

Examples of the Malacozoa include *Pomacea canaliculata, Achatina fulica, Meghimatium bilineatum, Lehmannina valentiana, Limax flavus, Acusta despecta sieboldiana* and the like.

The agrohorticultural insecticide of the present invention also has a strong controlling effect on Tomato leaf miner (*Tuta absoluta*) as other insect pest.

In addition, as zoobiotic Acari, which is one of the control targets, for example, Ixodes such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulates* and *Dermacentor taiwanesis*, Ornithonyssus such as *Dermanyssus gallinae, Ornithonyssus sylviarum* and *Ornithonyssus bursa*, Trombicula such as *Eutrombicula wichmanni, Leptotrombidium akamushi, Leptotrombidium pallidum, Leptotrombidium fuji, Leptotrombidium tosa, Neotromhicula autumnalis, Eutrombicula alfreddugesi* and *Helenicula miyagawai*, Cheyletidae such as *Cheyletiella yasguri, Cheyletiella parasitivorax* and *Cheyletiella blakei*, Sarcoptes such as *Psoroptes cuniculi, Chorioptes bovis, Otodectes cynotis, Sarcoptes scabiei* and *Notoedres cati*, Demodicidae such as *Demodex canis*, and the like can be mentioned.

As flea, which is another control target, for example, ectoparasitic wingless insects belonging to Siphonaptera, more specifically, flea belonging to Pulicidae, Ceratephyllus and the like can be mentioned. Examples of the flea belonging to Pulicidae include *Ctenocephalides canis, Ctenocephalides fells, Pulex irritans, Echidnophaga gallinacea, Xenopsylla cheopis, Leptopsylla segnis, Nosopsyllus fasciatus, Monopsyllus anisus* and the like.

Examples of the external parasite, which is another control target, include Anoplura such as shortnosed cattle louse (*Haematopinus eurysternus*), horse sucking louse (*Haematopinus asini*), sheep louse (*Dalmalinia ovis*), longnosed cattle louse (*Linognathus vituli*), pig louse (*Haematopinus suis*), crab louse (*Phthirus pubis*), and head louse (*Pediculus capitis*); biting lice such as dog biting louse (*Trichodectes canis*); and blood-sucking dipterous insects such as horsefly (*Tabanus trigonus*), biting midges (*Culicoides schultzei*), and blackfly (*Simulium ornatum*). Further, examples of the internal parasites include nematodes such as lung worms, whipworms, tuberous worms, gastric parasites, ascaris, and filarioidea; cestoda such as *Spirometra erinacei, Diphyllobothrium latum, Dipylidium caninum, Taenia multiceps, Echinococcus granulosus*, and *Echinococcus multilocularis*; trematoda such as *Schistosoma japonicum* and *Fasciola hepatica*; and protozoa such as coccidia, malaria parasites, intestinal sarcocystis, toxoplasma, and cryptosporidium.

The agrohorticultural insecticide containing the arylalkyloxypyrimidine derivative represented by the formula (I) or salts thereof of the present invention as an active ingredient has a marked controlling effect on the above-exemplified insect pests, which are injurious to paddy field crops, upland crops, fruit trees, vegetables and other crops, flowers and ornament plants, and the like. Therefore, the desired effect of the agrohorticultural insecticides of the present invention can be exhibited by applying the agents to the cultivation carrier such as seeds, paddy field water, stalks and leaves or soil of propagation facility, paddy field, field, fruit trees, vegetables, other crops or flowers and ornament plants and the like, at a season at which the insect pests are expected to appear, before their appearance or at the time when their appearance is confirmed. Particularly, preferable use form is application utilizing what is called penetration transferability by allowing absorption of the compound of the present invention from roots via or not via soil, by treating propagation soil for crops, flowers and ornamental plants and the like, planting hole soil for transplantation, plant foot, irrigation water, culture water for hydroponic culture and the like.

The useful plants, for which the agrohorticultural insecticide of the present invention can be used, are not specifically limited and, for example, plants such as cereals (e.g. rice, barley, wheat, rye, oat, corn etc.); legume (soybean, adzuki bean, fava bean, bean, kidney bean, peanut, etc.); fruit trees and fruits (apple, citrus fruits, pear, grapes, peach, plum, cherry fruit, walnut, sweet chestnut, almond, banana, etc.); vegetables (cabbage, tomato, spinach, broccoli, lettuce, onion, welsh onion (chives, welsh onion), green pepper, eggplant, strawberry, pepper, okra, leek etc,), root vegetables (carrot, potato, sweet potato, tannia, radish, turnip, lotus root, burdock, garlic, Japanese leek etc.), crop for processing (cotton, hemp, beet, hop, sugar cane, sugar beet, olive, rubber, coffee, tobacco, tea, etc.); gourd (pumpkin, cucumber, watermelon, oriental melon, melon, etc.); feed crop (orchard grass, sorghum, timothy, clover, alfalfa, etc.); grass (Korean lawn grass, bent grass, etc.); crop for spicery (lavender, rosemary, thyme, parsley, pepper, ginger, etc.); flowers (chrysanthemum, rose, carnation, orchid, tulip, lily etc.), garden tree (gingko, Japanese cherry, aucuba etc.), forest tree (*Abies sachalinensis, Picea jezoensis*, pines, *Thujopsis dolabrata*, Japanese cedar, Japanese cypress, eucalyptus etc.) and the like can be mentioned.

The above-mentioned "plant" also includes plants imparted with resistance to herbicides, for example, HPPD inhibitors such as isoxaflutole and the like, ALS inhibitors such as imazethapyr, thifensulfuron methyl and the like, EPSP synthase inhibitors such as glyphosate and the like, glutamine synthase inhibitors such as glufosinate and the like, acetyl CoA carboxylase inhibitors such as sethoxydim and the like, Broxynil, dicamba, 2,4-D and the like, by a classical breeding method or gene recombination technique.

Examples of the "plant" imparted with resistance by a classical breeding method include colza, wheat, sunflower and rice resistant to imidazolinone ALS inhibitory herbicides such as imazethapyr and the like, which are already commercially available as a trade name of Clearfield (registered trade mark). Similarly, soybean resistant to sulfonylurea ALS inhibitory herbicides such as thifensulfuron methyl and the like by a classical breeding method is already commercially available as a trade name of STS soybean. Similarly, examples of the plant imparted with resistance to acetyl CoA carboxylase inhibitors such as trione oxime and aryloxyphenoxypropionic acid herbicides and the like, by a classical breeding method include SR corn and the like.

The plant imparted with resistance to acetyl CoA carboxylase inhibitors is described in Proc. Natl. Acad. Sci. USA, vol. 87, pages 7175-7179 (1990) and the like. In addition, mutated acetyl CoA carboxylase resistant to acetyl CoA carboxylase inhibitors is reported in Weed Science, vol. 53, pages 728-746 (2005) and the like, and a plant resistant to acetyl CoA carboxylase inhibitors can be created by introducing such mutated acetyl CoA carboxylase gene into a plant by a gene recombination technique or introducing a mutation involved in imparting resistance into acetyl CoA carboxylase of the plant. Furthermore, a plant resistant to acetyl CoA carboxylase inhibitor, ALS inhibitor and the like can be created by introducing a mutation of site-specific amino acid substitution into the acetyl CoA carboxylase gene, ALS gene and the like of the plant by introducing a base substitution mutation-introducing nucleic acid represented by a chimeraplasty technique (Gura T. 1999. Repairing the Genome's Spelling Mistakes. Science 285: 316-318.)

into the plant cell. The agrihorticultural insecticide of the present invention can also be used for these plants.

Furthermore, examples of the toxins produced in such genetically modified plants include insecticidal proteins derived from *Bacillus cereus* and *Bacillus popilliae*; insecticidal proteins such as δ-endotoxins (e.g. CrylAb, CrylAc, CrylF, CrylFa2, Cry2Ab, Cry3A, Cry3Bbl and Cry9C), VIP1, VIP2, VIP3 and VIP3A, which are derived from *Bacillus thuringiensis*; toxins derived from nematodes; toxins produced by animals, such as scorpion toxin, spider toxin, bee toxin and insect-specific neurotoxins; filamentous fungi toxins; plant lectins; agglutinin; protease inhibitors such as trypsin inhibitors, serine protease inhibitor, patatin, cystatin and papain inhibitors; ribosome-inactivating proteins (RIP) such as ricin, corn-RIP, abrin, rufin, sapolin and priodin; steroid metabolic enzymes such as 3-hydroxysteroid oxidase, ecdysteroid-UDP-glucosyltransferase and cholesterol oxidase; ecdysone inhibitors; HMG-CoA reductase; ion channel inhibitors such as a sodium channel inhibitors and calcium channel inhibitors; juvenile hormone esterase; diuretic hormone acceptors; stilbene synthetase; bibenzyl synthetase; chitinase; glucanase and the like.

The toxins produced in such genetically modified plants also include hybrid toxins, partially deficient toxins and modified toxins of insecticidal proteins, such as δ-endotoxin proteins (e.g. CrylAb, CrylAc, CrylF, CrylFa2, Cry2Ab, Cry3A, Cry3Bbl, Cry9C, Cry34Ab and Cry35Ab), VIP1, VIP2, VIP3 and VIP3A. The hybrid toxins are produced by a novel combination of the different domains of such a protein by adopting recombination technology. The known partially deficient toxin is CrylAb, in which a part of amino acid sequence is deficient. In the modified toxins, one or a plurality of amino acids of a natural toxin is/are replaced.

Examples of such toxins and genetically modified plants capable of synthesizing such toxins are described in EP-A-0 374 753, WO 93/07278, WO 95/34656, EP-A-0 427 529, EP-A-451 878, WO 03/052073, etc.

The toxins contained in such genetically modified plants impart resistance to insect pests of Coleoptera, insect pests of Hemipteria, insect pests of Diptera, insect pests of Lepidoptera and Nematoda to the plants. The agrihorticultural insecticide of the present invention can also be used in combination with or by systematization with such technique.

For control of various pests, the agrohorticultural insecticide of the present invention need only be applied to the plant expected to allow occurrence of pests and nematode, as it is or after being properly diluted with or suspended in water or the like, in an amount effective for control of the pests or nematode. For example, for pests and nematodes that occur in fruit trees, cereals, vegetables and the like, the insecticide is sprayed on the stem and leaf parts, or absorbed from the root by seed treatments such as dipping the seeds in a drug, dressing of seeds, Calper treatment and the like, soil treatment such as soil whole layer blending, planting row application, bed soil blending, cell seedling treatment, planting hole treatment, plant foot treatment, top dress, box treatment of rice, water surface application etc., and the like. In addition, the agrohorticultural insecticide can also be used by application to a culture fluid for culture fluid (hydroponic) culture, application by smoking or tree stem injection and the like.

The agrohorticultural insecticide of the present invention need only be applied to the place expected to allow development of pests, as it is or after being properly diluted with or suspended in water or the like, in an amount effective for control of the pests. For example, spraying on grain-storage insects, house pests, hygiene pests, forest pests and the like, as well as application, smoking, bait to house and architectural materials and the like can also be employed for use.

As methods for seed treatment, conventional methods such as a method comprising penetration of the agent by dipping of seeds in the liquid agent obtained by diluting or not a liquid formulation or a solid formulation, a method comprising adhering a solid formulation or liquid formulation to the seed surface by admixing the formulation with seeds, dressing and the like, a method comprising admixing the formulation with adhesive carriers such as resin, polymer and the like and forming a coat on the seeds, a method comprising application near the seeds simultaneously with planting and the like can be mentioned.

The "seed" to be subjected to the seed treatment means a plant body in an early stage of growth, which is used for propagation, and includes seeds, as well as bulb, tuber, seed tuber, germ, propagule, scaly bulb, a plant body for vegetative propagation by cutting propagation, and the like.

The "soil" and "cultivation carrier" for plant when practicing the method of use of the present invention mean supports for cultivation of plants, particularly supports for growing roots, and the material is not particularly limited. The material may be any as long as plants can grow therein and specific materials include, for example, soils, nursery mat, water and the like. As a specific material, sand, pumice, vermiculite, diatomaceous earth, agar, gelled substance, polymer substance, rock wool, glass wool, wood chip, bark and the like can also be used.

As a method of application to crop plant stem and leaves, or grain-storage insect, house pest, hygiene pest or forest pest, a method including appropriately diluting a liquid formulation such as emulsion, flowable formulation and the like or a solid formulation such as a wettable powder or water dispersible granule and the like with water and spraying same, a method of spraying a dust, or smoking and the like can be mentioned.

For application to the soil, for example, a method comprising application of a liquid formulation to the plant foot of plant body, nursery for raising seedling and the like with or without dilution in water, a method comprising application of granules to the plant foot of plant body or nursery for raising seedling, a method comprising application of dust, wettable powder, water dispersible granule, granule and the like before sowing or transplantation to allow them to be incorporated into the entire soil, a method comprising application planting pit, planting row and the like with dust, wettable powder, water dispersible granule, granule and the like before sowing or planting and the like can be mentioned.

In the case of the paddy rice nursery box, the formulation may vary depending on the timing of, for example, application on sowing, application during greening, application during transplanting and the like. The formulations of dust, water dispersible granule, granule and the like can be employed. Application is also possible by incorporation into the grove soil, wherein the grove soil may be mixed with dust, water dispersible granule, granule and the like and, for example, incorporation into bed soil, incorporation into cover soil, incorporation into the entire grove soil and the like can be employed. Simply, a grove soil and various formulations may be applied in alternate layers.

As a method of application to a paddy field, a solid formulation such as jumbo, pack, granule, water dispersible granule and the like, a liquid formulation such as flowable, emulsion and the like are generally sprayed on a flooded paddy field. Alternatively, during rice planting, a suitable formulation can also be applied or injected to soil directly or after blending with a fertilizer. Moreover, by utilizing a liquid agent such as emulsion, flowable and the like to a water inlet and the flow source of water into paddy fields such as an irrigation apparatus and the like, a saving application along with the supply of water can also be performed.

For upland crops, treatment of seeds, a cultivation carrier to be placed near the plant body and the like during the period of from sowing to raising seedling is possible. For plants to be directly sown in the field, a direct treatment of seeds, a treatment of a plant foot of the plant under cultivation and the like are preferable. An application of granules, a soil injection treatment with a liquid agent with or without dilution with water and the like can be performed. It is also a preferable treatment to blend granules with a cultivation carrier before seeding, and seed the blend.

For a treatment on sowing or during raising seedling of a cultivated plant to be transplanted, a direct treatment of seeds, an soil injection treatment of nursery for raising seedling with a liquid agent or a dispersal treatment thereof with granules are preferable. In addition, treatment of a planting pit with granules and mixing of a cultivation carrier to be placed near the transplantation site with the granules during fix planting are also preferable treatments.

The agrohorticultural insecticide of the present invention is generally prepared into conveniently usable forms according to an ordinary manner for preparation of agrochemicals.

That is, the arylalkyloxypyrimidine oxide derivative represented by the formula (I) or salts thereof of the present invention are blended with a suitable inert carrier and, optionally, an adjuvant in a proper proportion and prepared into a suitable preparation form such as a suspension, emulsifiable concentrate, soluble concentrate, wettable powder, granular wettable powder, granules, dust, tablets, pack or the like through dissolution, dispersion, suspension, mixing, impregnation, adsorption or sticking.

The composition (agrohorticultural insecticide or animal parasite controlling agent) of the present invention can contain, besides active ingredients as necessary, additional components generally used for pesticide preparation or animal parasite controlling agent. Examples of the additional component include carriers such as solid carrier, liquid carrier and the like, surfactant, dispersant, wetting agent, binder, tackifies, thickener, colorant, spreader, sticker, antifreezing agent, anticaking agent, disintegrant, stabilizing agent and the like. Where necessary, preservative, plant detritus and the like may be used as other additional components. These addition components may be used alone or in a mixture of two or more kinds thereof.

Examples of the solid carrier include natural minerals such as quartz, clay, kaolinite, pyrophyllite, sericite, talc, bentonite, acid clay, attapulgite, zeolite, diatomaceous earth and the like; inorganic salts such as calcium carbonate, ammonium sulfate, sodium sulfate, potassium chloride and the like; organic solid carriers such as synthetic silicic acid, synthetic silicate, starch, cellulose, a vegetable powder (e.g., sawdust, coconut shell, corn cob, tobacco stalk and the like) and the like; plastic carriers such as polyethylene, polypropylene, poly(vinylidene chloride) and the like; urea, hollow inorganic bodies, hollow plastic bodies, fumed silica (white carbon) and the like. These may be used alone or in a mixture of two or more kinds thereof.

Examples of the liquid carrier include alcohols including monovalent alcohols such as methanol, ethanol, propanol, isopropanol, butanol and the like and polyvalent alcohols such as ethylene glycol, diethylene glycol, propylene glycol, hexylene glycol, polyethylene glycol, polypropylene glycol, glycerol and the like; polyhydric alcohol compounds such as propylene glycol ether and the like; ketones such as acetone, methyl ethyl ketone, methyl isobutyl ketone, diisobutyl ketone, cyclohexanone and the like; ethers such as ethyl ether, dioxane, ethylene glycol monoethyl ether, dipropyl ether, tetrahydrofuran and the like; aliphatic hydrocarbons such as normal paraffins, naphthenes, isoparaffins, kerosenes, mineral oils and the like; aromatic hydrocarbons such as benzene, toluene, xylene, solvent naphtha, alkylnaphthalenes and the like; halogenated hydrocarbons such as dichloromethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water and the like. These may be used alone or in a mixture of two or more kinds thereof.

Examples of the surfactant to be used as a dispersant or moistening agent include nonionic surfactants such as sorbitan ester of fatty acids, polyoxyethylene sorbitan ester of fatty acids, sucrose ester of fatty acids, polyoxyethylene fatty acid esters, polyoxyethylene resinate esters, polyoxyethylene fatty acid diesters, polyoxyethylene alkyl ethers, polyoxyethylene alkylaryl ethers, polyoxyethylene alkylphenyl ethers, polyoxyethylene dialkyl phenyl ethers, polyoxyethylene alkyl phenyl ether-formalin condensates, polyoxyethylene-polyoxypropylene block copolymers, polyoxystyrene-polyoxyethylene block copolymers, alkyl polyoxyethylene-polypropylene block copolymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, alkylarylsulfonate salts, lignin sulfonate salts, alkylsulfosuccinate salts, naphthalenesulfonate salts, alkylnaphthalenesulfonate salts, salts of formalin condensate of naphthalenesulfonic acid, salts of formalin condensate of alkylnaphthalenesulfonic acid, fatty acid salts, polycarboxylate salts, polyacrylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylaminopropylamine acetate salts, alkylamine salts including alkyltrimethylammonium chloride and alkyldimethylbenzalkonium chloride and the like; ampholytic surfactants such as amino acid or betaine surfactants and the like, and the like. These surfactants may be used alone or in a mixture of two or more kinds thereof.

Examples of the binder and tackifier include carboxymethylcellulose or salt thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, phospholipid (e.g. cephalin or lecithin), cellulose powder, dextrin, processed starch, polyaminocarboxylic acid chelate compound, crosslinked polyvinylpyrrolidone, maleic acid-styrene copolymer, (meth)acrylic acid copolymer, half ester between polyhydric alcohol and dicarboxylic anhydride, water-soluble salt of polystyrenesulfonic acid, paraffin, terpene, polyamide resin, polyacrylic acid salt, polyoxyethylene, wax, polyvinylalkyl ether, alkylphenol formaldehyde condensate, and synthetic resin emulsion and the like.

Examples of the thickener include water-soluble polymers such as xanthan gum, guar gum, diutan gum, carboxymethylcellulose, polyvinylpyrrolidone, a carboxyvinyl polymer, an acrylic polymer, a starch derivative and a polysaccharide; inorganic fine powders such as high-purity bentonite and fumed silica (white carbon) and the like.

Examples of the colorant include inorganic pigments such as iron oxide, titanium oxide, and Prussian blue; organic dyes such as an alizarin dye, azo dye, and metal phthalocyanine dye and the like.

Examples of the antifreezing agent include polyvalent alcohols such as ethylene glycol, diethylene glycol, propylene glycol, glycerol and the like, and the like.

Examples of the aids for anticaking or disintegrating include polysaccharides (e.g. starch, alginic acid, mannose and galactose), polyvinylpyrrolidone, fumed silica (white carbon), ester gum, petroleum resin, sodium tripolyphosphate, sodium hexametaphosphate, metal stearate, cellulose powder, dextrin, methacrylic acid ester copolymer, polyvinylpyrrolidone, polyaminocarboxylic acid chelate compound, sulfonated styrene-isobutylene-maleic anhydride copolymer, and starch-polyacrylonitrile graft copolymer and the like.

Examples of the stabilizing agent include desiccants such as zeolite, calcined lime and magnesium oxide; antioxidants such as phenol compounds, amine compounds, sulfur compounds, phosphoric acid compounds and the like; ultraviolet absorbers such as salicylic acid compounds, benzophenone compounds and the like, and the like.

Examples of the preservative include potassium sorbate, 1,2-benzothiazolin-3-one and the like.

Further, if necessary, functional spreading agents, active enhancers such as metabolic decomposition inhibitor like piperonyl butoxide, anti-freezing agents such as propylene glycol, antioxidizing agents such as BHT, ultraviolet absorbers, and other aids may also be used.

The content of the compound as active ingredient may be varied as required, and the compound as active ingredient may be used in a proportion properly chosen in the range of 0.01 to 90 parts by weight per 100 parts of the agrohorticultural agents of the present invention. For example, in dusts, granules, emulsion or wettable powders, the suitable content of the compound as an active ingredient is from 0.01 to 50 parts by weight (0.01 to 50 wt % of the total weight of the agrohorticultural insecticide).

The applicable dosage of the agrohorticultural insecticide of the present invention varies depending upon various factors such as a purpose, insect pests to be controlled, a growth state of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient) per 10 ares depending upon purposes.

The agrohorticultural insecticide of the present invention may be used in admixture with other agrohorticultural insecticides, acaricides, nematocides, fungicides, biotic pesticides or the like in order to expand both spectrum of controllable disease and insect pest and the period of time when effective application are possible or to reduce the dosage. Furthermore, the agrohorticultural insecticide of the present invention may be used in admixture with herbicides, plant growth regulators, fertilizers or the like, depending upon application situations.

Examples of other agrohorticultural insecticides, acaricides and nematocides to be used for such purpose include 3,5-xylyl methylcarbamate (XMC), crystal protein toxin produced by *Bacillus thuringienses aizawai*, *Bacillus thuringienses israelensis*, *Bacillus thuringienses japonensis*, *Bacillus thuringienses kurstaki*, *Bacillus thuringienses tenebrionis*, or *Bacillus thuringienses*, BPMC, Bt toxin insecticide compound, CPCBS (chlorfenson), DCIP (dichlorodiisopropyl ether), D-D (1,3-Dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb: MIPC, ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos: ESP, oxibendazole, oxfendazole, Potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, dicofol, salithion, cyanophos: CYAP, diafenthiuron, diamidafos, cyantraniliprole, theta-cypermethrin, dienochlor, cyenopyrafen, dioxabenzofos, diofenolan, sigma-cypermethrin, dichlofenthion: ECP, cycloprothrin, dichlorvos: DDVP, disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon: DEP, triflumuron, tolfenpyrad, naled: BRP, nithiazine, nitenpyram, novaluron, noviflumuron, hydroprene, vaniliprole, vamidothion, parathion, parathion-methyl, halfenprox, halofenozide, bistrifluoron, bisultap, hydramethylnon, hydroxy propyl starch, binapacryl, bifenazate, bifenthrin, pymetrozine, pyraclorfos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion: MEP, fenoxycarb, fenothiocarb, phenothrin, fenobucarb, fensulfothion, fenthion: MPP, phenthoate: PAP, fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenoprox, fluproxyfen, flubrocythrinate, flubendiamide, flumethrin, flurimfen, prothiofos, protrifenbute, flonicamid, propaphos, propargite: BPPS, profenofos, profluthrin, propoxur: PHC, bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet: PMP, polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion: DMTP, methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisol hydrochloride, fenbutatin oxide, morantel tartarate, methyl bromide, cyhexatin, calcium cyanamide, calcium polysulfide, sulfur, nicotine-sulfate and the like.

Examples of the agrohorticultural fungicides to be used for the same purpose as above include soil fungicides such as aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium and the like, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloranifoLInethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfuram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecylbenzenesulphonic acid bisethylenediamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metamsodium, metalaxyl, metalaxyl-M, metiram, methyl isothiocyanate, mepthyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, inorganic antimicrobial agents such as basic copper sulfate, silver and the like, sodium hypochlorote, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as oxine copper, zinc sulfate, copper sulfate pentahydrate and the like.

Similarly, examples of the herbicide include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate ethyl, ethidimuron, etinofen, ethephon, ethoxysulfuron, ethoxyfen, etniproinid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosaur, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluoron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluoron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluoron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluoroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluoroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide, methyl bromide and the like.

As to the biotic pesticides, the same effect as above can be expected by using the agrohorticultural agent of the present invention in admixture with, for example, viral formulations obtained from Nuclear polyhedrosis virus (NPV), Granulosis virus (GV), Cytoplasmic polyhedrosis virus (CPV), Entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobacter*, nonpathogenic *Erwinia carotovora, Bacillus subtilis*, etc.; and biotic pesticides utilized as herbicides, such as *Xanthomonas campestris*, etc.

In addition, the agrohorticultural agent of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as *Beauveria brongniartii*, etc.; and pheromones such as (Z)-10-tetradecenyl acetate, (E,Z)-4,10-tetradecadieniel acetate, (Z)-8-dodecenyl acetate, (Z)-11-tetradecenyl acetate, (Z)-13-icosen-10-one, 14-methyl-1-octadecene, etc.

Representative examples of the present invention are shown below, which are not to be construed as limitative.

REFERENCE EXAMPLE 1-1

Production of 5-butyl-4-hydroxypyrimidine

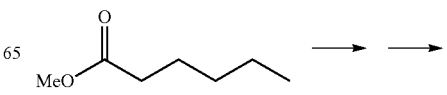

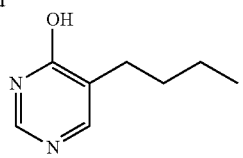

To a solution of sodium methoxide (8.3 g, 154 mmol) in dehydrated tetrahydrofuran (40 mL) were successively added dropwise under an argon atmosphere at 5-10° C. ethyl formate (7.4 g, 100 mmol), and hexanoic acid methyl ester (10 g, 77 mmol), and the mixture was stirred at room temperature for 3 hr. To the reaction solution were added dropwise a solution of formamidine acetate (8.0 g, 77 mmol) in methanol (70 mL) and a 28% solution (16 g, 81 mmol) of sodium methoxide in methanol, and the mixture was stirred with heating under reflux for 10 hr. The reaction solution was cooled to room temperature, water (10 mL) was added to dissolve the precipitated salt, and the mixture was concentrated under reduced pressure. Concentrated hydrochloric acid (15 mL) was added, and the mixture was extracted with ethyl acetate. The organic layer was dried over anhydrous magnesium sulfate, concentrated under reduced pressure, and purified by silica gel column chromatography to give 5-n-butyl-4-hydroxypyrimidine (1.3 g, 11%).

yield: 11% property: $^1$H-NMR (400 MHz, CDCl$_3$):δ 8.05 (s, 1H), 7.85 (s, 1H), 2.50 (t, 2H), 1.65-1.66 (m, 2H), 1.45-1.35 (m, 2H), 0.95 (t, 3H)

REFERENCE EXAMPLE 1-2

Production of 5-butyl-4-chloropyrimidine

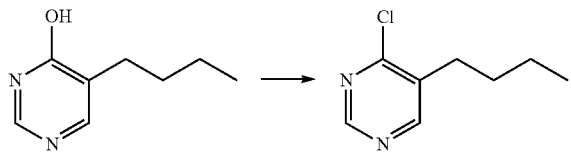

To a solution of 5-butyl-4-hydroxypyrimidine (1.3 g, 8.5 mmol) produced in the previous production method in toluene (5 mL) was added phosphorus oxychloride (3.9 g, 26 mmol), and the mixture was stirred with heating under reflux for 2 hr. The mixture was cooled to room temperature, and concentrated under reduced pressure to remove excess phosphorus oxychloride. The residue was poured into saturated aqueous sodium hydrogen carbonate, and the mixture was extracted with MTBE. The organic layer was dried over anhydrous magnesium sulfate, and concentrated under reduced pressure to give 5-butyl-4-chloropyrimidine (1.1 g, 76%) as a crude purified product.

yield: 76% property: $^1$H-NMR (400 MHz, CDCl$_3$):δ 8.84 (s, 1H), 8.51 (s, 1H), 2.72 (t, 2H), 1.70-1.60 (m, 2H), 1.50-1.40 (m, 2H), 0.98 (t, 3H)

EXAMPLE 1

Production of 5-butyl-4-(4-t-butylbenzyloxy)pyrimidine (compound No. 1-7)

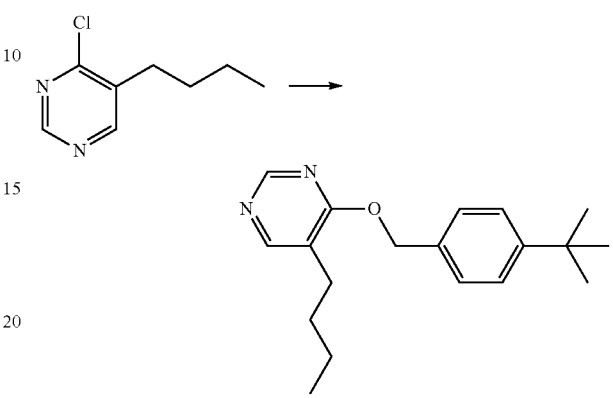

To a solution of 5-butyl-4-chloropyrimidine (0.20 g, 1.2 mmol) produced in the previous production method and 4-t-butylbenzyl alcohol (0.19 g, 1.2 mmol) in THF (5 mL) was added at 0° C. sodium hydride (0.051 g, 1.3 mmol), and the mixture was stirred at room temperature for 3 hr. The reaction mixture was poured into ice water and the mixture was extracted with ethyl acetate. The organic layer was dried over anhydrous magnesium sulfate and the solvent was concentrated under reduced pressure. The residue was purified by silica gel column chromatography to give 5-butyl-4-(4-t-butylbenzyloxy)pyrimidine (0.26 g, 74%).

yield: 74% property: 1.5360 (27.5° C.)

REFERENCE EXAMPLE 2-1

Production of 4,6-dichloro-5-(1,3-dioxolan-2-yl)pyrimidine

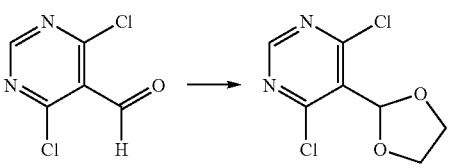 [SMILES: O=Cc1c(Cl)ncnc1Cl ; Clc1ncnc(Cl)c1C1OCCO1]

To a solution of 4,6-dichloro-5-formylpyrimidine (10 g, 56.5 mmol) synthesized in reference to WO2001/017975 in toluene (60 ml) were added at room temperature p-toluenesulfonic acid (1 g, 5.65 mmol) and ethylene glycol (7 g, 113 mmol), and the mixture was azeotropically stirred with heating under reflux for 30 min. To the reaction solution was added ethyl acetate, and the mixture was washed with saturated aqueous sodium hydrogen carbonate and saturated brine. The organic layer was dried over anhydrous magnesium sulfate, and concentrated under reduced pressure. The residue was purified by silica gel column chromatography to give 4,6-dichloro-5-(1,3-dioxolan-2-yl)pyrimidine (8.4 g).

yield: 67% property: $^1$H-NMR (400 MHz, CDCl$_3$):δ 8.75 (s, 1H), 6.37 (s, 1H), 4.28-4.37 (m, 2H), 4.06-4.15 (m, 2H)

REFERENCE EXAMPLE 2-2

Production of 6-chloro-4-(4-trifluoromethylbenzyloxy)-5-(1,3-dioxolan-2-yl)pyrimidine

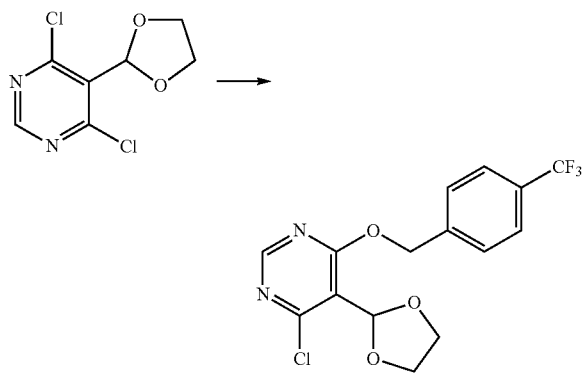

To a solution of 4,6-dichloro-5-(1,3-dioxolan-2-yl)pyrimidine (2.0 g, 9.1 mmol), and 4-trifluoromethylbenzyl alcohol (1.8 g, 10 mmol) in DMA (10 mL) was added at 0° C. sodium hydride (0.43 g, 11 mmol), and the mixture was stirred at room temperature for 3 hr. The reaction mixture was poured into ice water and the mixture was extracted with ethyl acetate. The organic layer was dried over anhydrous magnesium sulfate and the solvent was concentrated under reduced pressure. The residue was purified by silica gel column chromatography to give 6-chloro-4-(4-trifluoromethylbenzyloxy)-5-(1,3-dioxolan-2-yl)pyrimidine (2.2 g, 67%).

yield: 67% property: $^1$H-NMR (400 MHz, CDCl$_3$):δ 8.53 (s, 1H), 7.64 (d, 2H), 7.53 (d, 2H), 6.34 (s, 1H), 4.15-4.10 (m, 2H), 4.05-3.95 (m, 2H)

EXAMPLE 2

Production of 4-(4-trifluoromethylbenzyloxy)-5-(1,3-dioxolan-2-yl)pyrimidine (compound No. 4-4)

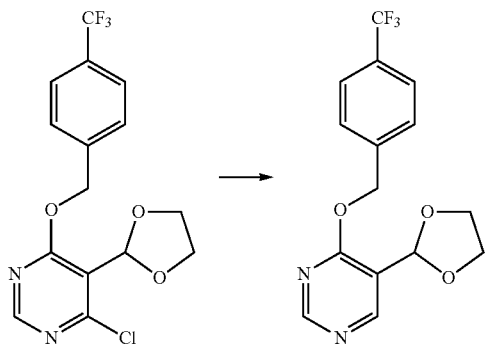 [SMILES: FC(F)(F)c1ccc(COc2ncnc(Cl)c2C2OCCO2)cc1 ; FC(F)(F)c1ccc(COc2ncncc2C2OCCO2)cc1]

To a solution of 6-chloro-4-(4-trifluoromethylbenzyloxy)-5-(2-dioxolanyl)pyrimidine (2.2 g, 6.1 mmol) in DMA (10 mL) were added under an argon atmosphere triethylamine (1.0 g, 10 mmol), formic acid (0.42 g, 9.1 mmol) and tetrakis(triphenylphosphine)palladium (0.70 g, 0.61 mmol), and the mixture was stirred at 80° C. for 3 hr. To the reaction solution was added water, and the mixture was extracted with tertiary butyl methyl ether. The organic layer was washed with water and saturated brine, and dried over anhydrous magnesium sulfate, and concentrated under reduced pressure. The residue was purified by silica gel column chromatography to give 4-(4-trifluoromethylbenzyloxy)-5-(1,3-dioxolan-2-yl)pyrimidine (0.47 g, 24%).

yield: 24% property: 38-39° C.

Formulation Examples are shown in the following, which do not limit the present invention. In Formulation Examples, part means parts by weight.

FORMULATION EXAMPLE 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate is prepared by mixing uniformly the above ingredients to allow dissolution.

FORMULATION EXAMPLE 2

| | |
|---|---|
| Compound of the present invention | 3 parts |
| Clay powder | 82 parts |
| Diatomaceous earth powder | 15 parts |

A dust is prepared by mixing uniformly and grinding the above ingredients.

FORMULATION EXAMPLE 3

| | |
|---|---|
| Compound of the present invention | 5 parts |
| Mixed powder of bentonite and clay | 90 parts |
| Calcium ligninsulfonate | 5 parts |

Granules are prepared by mixing the above ingredients uniformly, and kneading the resulting mixture together with a suitable amount of water, followed by granulation and drying.

FORMULATION EXAMPLE 4

| | |
|---|---|
| Compound of the present invention | 20 parts |
| Mixture of kaolin and synthetic High-dispersion silicic acid | 75 parts |
| Mixture of polyoxyethylene nonylphenyl ether and calcium alkylbenzenesulfonate | 5 parts |

A wettable powder is prepared by mixing uniformly and grinding the above ingredients.

EXPERIMENTAL EXAMPLE 1

Control Efficacy Against Green Peach Aphid (*Myzus persicae*)

A Chinese cabbage plant was planted in each of plastic pots with a diameter of 8 cm and a height of 8 cm and green peach aphids were propagated on the plant, after which the aphids in each pot were counted. Each arylalkyloxypyrimidine derivative of the general formula (I) or a salt thereof of the present invention was dispersed in and diluted with water to obtain a 500 ppm liquid chemical. The stalks and leaves of the potted Chinese cabbage plants were sprayed with the liquid chemical and air-dried, and then the pots were stored in a greenhouse. Six days after the spraying, green peach aphids parasitic on each Chinese cabbage plant were counted and the control efficacy degree was calculated by the following equation, whereby the insecticidal effect was judged according to the criterion shown below.

Control efficacy=100−{(T×Ca)/(Ta×C)}×100

Ta: number of parasites before spraying in treated group,
T: number of parasites after spraying in treated group,
Ca: number of parasites before spraying in untreated group,
C: number of parasites after spraying in untreated group.
A . . . control efficacy 100%
B . . . control efficacy 99%-90%
C . . . control efficacy 89%-80%
D . . . control efficacy 79%-50%

EXPERIMENTAL EXAMPLE 2

Insecticidal Effect on Brown Rice Planthopper (*Nilaparvata Lugens*)

Each arylalkyloxypymidine derivative of the general formula (I) or a salt thereof of the present invention was dispersed in and diluted with water to obtain a 500 ppm liquid chemical. Rice seedlings (cultivar: Nihonbare) were immersed in the liquid chemical for 30 seconds and air-dried, after which each seedling was placed in a glass test tube and inoculated with 10 third-instar nymphs of brown rice planthopper, and the test tube was plugged with a cotton plug. Eight days after the inoculation, the dead and alive were counted. The corrected mortality was calculated by the following equation and the control effect was judged according to the criterion described below.

$$\text{Corrected mortality}(\%) = \frac{(\text{survival rate in untreated group}) - (\text{survival rate in treated group})}{(\text{survival rate in untreated group})} \times 100$$

diagnostic criteria . . . same as in Experimental Example 1.

As a result, in Experimental Example 1, among the arylalkyloxypyrimidine derivatives of the present invention represented by the formula (I), the compounds of compound Nos. 1-1, 1-2, 1-3, 1-4, 1-5, 1-7, 1-8, 1-13, 1-14, 1-21, 1-30, 1-37, 1-40, 1-54, 1-55, 1-70, 1-95, 1-110, 2-2, 2-3, 2-4, 2-5, 2-7, 2-8, 2-9, 2-13, 2-14, 2-21, 2-30, 2-37, 2-41, 2-51, 2-52, 2-54, 2-55, 2-59, 2-62, 2-66, 2-67, 2-73, 2-76, 2-77, 2-87, 2-88, 2-95, 2-97, 2-100, 2-102, 2-103, 2-104, 2-107, 2-108, 3-2, 3-3, 3-4, 3-5, 3-7, 3-8, 3-9, 3-13, 3-14, 3-21, 3-31, 3-37, 3-51, 3-52, 3-67, 3-68, 3-78, 3-95, 3-111, 4-1, 4-3, 4-4, 4-6, 4-9, 4-10, 4-18, 4-19, 4-20, 4-21, 4-22, 4-23, 4-26, 4-28, 4-31, 4-33, 4-38, 4-40, 4-41, 4-42, 4-43, 4-45, 4-46, 4-47, 4-51, 4-52, 4-53, 4-56, 4-57, 4-63, 4-66, 4-67, 4-68, 4-71, 4-72, 4-78, 4-81, 4-82, 4-86, 4-88, 4-89, 4-90, 5-1, 5-2, 5-3, 7-52, 8-1, 8-2, 8-5, 8-7, 8-8, 8-9, 8-10, 8-12, 8-13, 8-14, 8-15, 8-16, 8-17, 8-18, 8-19, 8-20, 8-21, 8-22, 8-23, 8-24, 8-26, 8-27, 8-28, 8-29, 8-31, 8-32, 8-34, 8-35, 8-37, 8-39, 8-40, 8-42, 8-49, 8-50, 8-51, 8-52, 8-53, 8-54, 8-57, 8-58, 8-59, 8-60, 8-61, 8-62, 8-63, 8-64, 9-2, 9-3, 9-6, 9-7, 9-10, 9-11, 9-12, 9-13, 9-14, 9-18, 9-19, 9-20, 9-21, 9-25, 9-26, 9-27, 9-28, 9-29, 9-31, 9-32, 9-33, 9-34, 9-41, 9-42, 9-43, 9-44, 9-45, 9-46, 10-1, 10-2, 10-3, 10-4, 10-5, 10-6, 10-7, 10-8, 10-9, 10-10, 10-11, 12-3, 12-4, 12-5, 12-10, 12-11, 12-12, 12-13, 12-19, 12-20, 12-23, 14-2, 14-3, 14-5, 14-8, 14-10, 14-11, 14-12, 14-13, 14-14, 14-15, 14-16, 14-17, 14-18, 14-19, 14-20, 14-23, 14-25, 14-27, 14-41, 14-44, 14-46, 14-47, 14-49, 14-50, 14-52, 14-52, 14-54, 14-55, 14-56, 14-57, 14-60, 14-64, 14-65, 14-66, 14-86, 14-90, 14-98, 14-102, 14-104, 14-105, 14-106, 14-112, 14-117, 14-118, 14-119, 14-120, 14-121, 14-122, 14-123, 15-1, 15-2, 15-4, 15-5, 15-6, 15-8, 15-9, 15-10, 15-11, 15-12, 15-13, 15-14, 15-15, 15-16, 15-17, 15-22, 15-24, 15-27, 15-29, 15-30, 15-31, 15-33, 15-34, 15-40, 15-43, 15-44, 15-45, 15-46, 15-47, 15-52, 15-60, 15-61, 15-62, 15-63, 15-65, 15-74, 15-75, 15-76, 15-77, 15-78, 15-81, 15-83, 15-84, 15-86, 15-87, 15-88, 15-90, 15-91, 15-92, 15-93, 15-94, 15-95, 15-96, 15-97, 15-101, 15-106, 15-108, 15-110, 15-113 and 15-114 showed insecticidal effects of not less than D against green peach aphid, and particularly, the compounds of 1-1, 1-2, 1-4, 1-5, 1-7, 1-8, 1-13, 1-37, 2-3, 2-4, 2-7, 2-8, 2-9, 2-13, 2-21, 2-30, 2-37, 2-54, 2-59, 2-100, 2-104, 2-107, 3-2, 3-3, 3-5, 3-7, 3-8, 3-9, 3-21, 3-37, 3-52, 3-67, 3-68, 3-78, 3-95, 4-1, 4-3, 4-4, 4-9, 4-19, 4-20, 4-23, 4-31, 4-33, 4-38, 4-41, 4-46, 4-47, 4-51, 4-52, 4-56, 4-57, 4-63, 4-66, 4-67, 4-72, 4-78, 4-81, 4-82, 5-3, 7-52, 8-7, 8-8, 8-14, 8-18, 8-19, 8-22, 8-26, 8-27, 8-28, 8-31, 8-32, 8-37, 8-39, 8-49, 8-59, 8-63, 9-3, 9-10, 9-11, 9-19, 9-25, 9-33, 9-34, 9-43, 9-45, 10-1, 10-4, 10-5, 10-6, 10-8, 10-9, 14-5, 14-10, 14-12, 14-15, 14-17, 14-23, 14-25, 14-46, 14-47, 14-49, 14-50, 14-52, 14-54, 14-60, 14-102, 14-104, 14-105, 14-117, 14-118, 14-119, 14-120, 14-121, 14-122, 15-2, 15-4, 15-11, 15-12, 15-14, 15-22, 15-27, 15-33, 15-60, 15-61, 15-62, 15-75, 15-76, 15-77, 15-78, 15-84, 15-86, 15-87, 15-88, 15-90, 15-92, 15-93, 15-110 and 15-114 showed superior insecticidal effects of A.

In addition, in Experimental Example 2, among the arylalkyloxypyrimidine derivatives of the present invention represented by the formula (I), the compounds of compound Nos. 1-1, 1-2, 1-3, 1-4, 1-5, 1-7, 1-8, 1-9, 1-13, 1-14, 1-21, 1-30, 1-31, 1-37, 1-40, 1-52, 1-54, 1-55, 1-72, 1-100, 2-2, 2-3, 2-4, 2-5, 2-7, 2-8, 2-9, 2-13, 2-14, 2-21, 2-30, 2-31, 2-37, 2-41, 2-52, 2-54, 2-55, 2-57, 2-66, 2-67, 2-73, 2-76, 2-87, 2-95, 2-97, 2-100, 2-105, 2-107, 2-108, 3-2, 3-3, 3-4, 3-5, 3-7, 3-8, 3-9, 3-13, 3-14, 3-21, 3-37, 3-52, 3-67, 3-68, 3-78, 3-88, 3-95, 4-1, 4-3, 4-4, 4-6, 4-9, 4-10, 4-16, 4-18, 4-19, 4-20, 4-21, 4-22, 4-28, 4-31, 4-38, 4-40, 4-41, 4-42, 4-43, 4-44, 4-45, 4-51, 4-52, 4-53, 4-56, 4-57, 4-63, 4-66, 4-67, 4-68, 4-71, 4-72, 4-78, 4-81, 4-82, 5-1, 5-2, 5-3, 7-52, 8-2, 8-5, 8-6, 8-7, 8-8, 8-9, 8-10, 8-14, 8-15, 8-16, 8-17, 8-18, 8-19, 8-20, 8-22, 8-23, 8-24, 8-26, 8-28, 8-29, 8-31, 8-32, 8-33, 8-34, 8-35, 8-36, 8-37, 8-39, 8-40, 8-45, 8-47, 8-49, 8-52, 8-53, 8-54, 8-58, 8-59, 8-60, 8-63, 8-64, 9-1, 9-2, 9-3, 9-4, 9-6, 9-9, 9-10, 9-11, 9-12, 9-18, 9-19, 9-20, 9-21, 9-22, 9-25, 9-26, 9-31, 9-32, 9-33, 9-35, 9-36, 9-38, 9-39, 9-40, 9-42, 9-43, 9-45, 9-47, 10-1, 10-2, 10-3, 10-4, 10-5, 10-6, 10-7, 10-8, 10-10, 10-11, 14-1, 14-5, 14-9, 14-10, 14-11, 14-12, 14-13, 14-14, 14-16, 14-17, 14-18, 14-19, 14-20, 14-22, 14-25, 14-27, 14-29, 14-36, 14-37, 14-39, 14-40, 14-41, 14-43, 14-44, 14-46, 14-47, 14-49, 14-50, 14-51, 14-52, 14-53, 14-54, 14-55, 14-56, 14-57, 14-58, 14-59, 14-60, 14-62, 14-63, 14-65, 14-67, 14-69, 14-86, 14-102, 14-103, 14-104, 14-105, 14-106, 14-109, 14-116, 14-117, 14-118, 14-119, 14-120, 14-121, 14-122, 14-123, 15-1, 15-2, 15-4, 15-5, 15-6, 15-7, 15-8, 15-9, 15-10, 15-11, 15-12, 15-13, 15-14, 15-15, 15-16, 15-17, 15-19, 15-20, 15-21, 15-22, 15-23, 15-24, 15-25, 15-26, 15-28, 15-29, 15-30, 15-31, 15-34, 15-35, 15-36, 15-37, 15-38, 15-39, 15-40, 15-41, 15-46, 15-47, 15-48, 15-49, 15-50, 15-52, 15-53, 15-54, 15-55, 15-56, 15-57, 15-58, 15-59, 15-60, 15-61, 15-62, 15-63, 15-64, 15-66, 15-67, 15-70, 15-71, 15-72, 15-75, 15-76, 15-77, 15-78, 15-79, 15-80, 15-81, 15-83, 15-84, 15-85, 15-86, 15-87, 15-88, 15-90, 15-91, 15-92, 15-93, 15-95, 15-97, 15-100, 15-106, 15-109, 15-110, 15-111, 15-112, 5-113 and 15-114 showed insecticidal effects of not less than D against brown rice planthopper, and particularly, the compounds of 1-1, 1-2, 1-3, 1-4, 1-5, 1-7, 1-8, 1-9, 1-13, 1-21, 1-30, 1-37, 1-40, 1-54, 1-55, 1-72, 1-100, 2-2, 2-3, 2-4, 2-5, 2-7, 2-8, 2-9, 2-13, 2-14, 2-21, 2-30, 2-37, 2-41, 2-54, 2-55, 2-67, 2-73, 2-87, 2-97, 2-100, 2-105, 3-3, 3-4, 3-5, 3-7, 3-8, 3-9, 3-13, 3-14, 3-21, 3-37, 3-68, 3-78, 3-95, 4-1, 4-3, 4-4, 4-6, 4-9, 4-16, 4-18, 4-19, 4-20, 4-21, 4-22, 4-38, 4-40, 4-41, 4-43, 4-45, 4-53, 4-57, 4-63, 4-66, 4-67, 4-71, 4-72, 4-78, 5-1, 5-2, 5-3, 8-6, 8-7, 8-8, 8-14, 8-19, 8-22, 8-24, 8-26, 8-28, 8-29, 8-31, 8-32, 8-34, 8-35, 8-37, 8-39, 8-49, 8-53, 8-59, 8-60, 9-1, 9-2, 9-3, 9-4, 9-10, 9-18, 9-20, 9-21, 9-22, 9-26, 9-31, 9-32, 9-38, 9-39, 9-43, 9-47, 10-1, 10-2, 10-3, 10-4, 10-5, 10-6, 10-7, 10-8, 10-10, 10-11, 14-5, 14-10, 14-12, 14-14, 14-20, 14-27, 14-46, 14-47, 14-49, 14-50, 14-52, 14-54, 14-55, 14-56, 14-60, 14-102, 14-104, 14-105, 14-117, 14-118, 14-119, 14-120, 14-121, 14-122, 14-123, 15-4, 15-6, 15-10, 15-13, 15-14, 15-31, 15-35, 15-36, 15-39, 15-40, 15-41, 15-47, 15-48, 15-49, 15-52, 15-54, 15-55, 15-56, 15-59, 15-60, 15-61, 15-62, 15-63, 15-77, 15-78, 15-86, 15-88, 15-106, 15-110, 15-111, 5-113 and 15-114 showed superior insecticidal effects of A.

EXPERIMENTAL EXAMPLE 3

Acaricidal Effect on Cattle Tick (*Haemaphysalis longicornis*)

An absorbent cotton was placed on the basement of a glass bottle (diameter 3 cm× height 4.5 cm). The arylalkyloxypyrimidine derivative of the present invention represented by the formula (I) or a salt thereof was dispersed in water to give a diluted drug solution (200 ppm). The drug solution (2 ml) was added dropwise. Cattle ticks were inoculated by 5 each, and the bottle was capped with a mesh. After 4 days from the inoculation, the dead ticks and live ticks were counted, and the corrected mortality was calculated by the following formula and the acaricidal effect was judged according to the criterion of Experimental Example 1.

Corrected mortality(%)=(survival rate in untreated group−survival rate in treated group)/(survival rate in untreated group)×100

As a result, among the arylalkyloxypyrimidine derivatives of the present invention represented by the formula (I), the compounds of compound Nos. 1-2, 2-5, 2-37, 2-54, 3-21, 3-111, 4-19, 4-41, 4-53, 4-67, 8-22, 8-26, 9-45, 10-7 and 15-78 showed acaricidal effects of not less than D against cattle tick, and particularly, the compounds of 1-2, 2-5, 2-54, 3-21, 3-111, 4-67, 9-45 and 15-78 showed superior acaricidal effects of A.

INDUSTRIAL APPLICABILITY

The arylalkyloxypyrimidine derivative of the present invention or a salt thereof has a superior effect as an agrohorticultural insecticide. On the other hand, the derivative shows an effect on pests being parasitic in pet animals such as dogs and cats, and domestic animals such as cattle, sheep and the like.

This application is based on patent application Nos. 019768/2012 and 171532/2012 filed in Japan, the contents of which are hereby incorporated by reference.

The invention claimed is:

1. An arylalkyloxypyrimidine derivative represented by the formula (I):

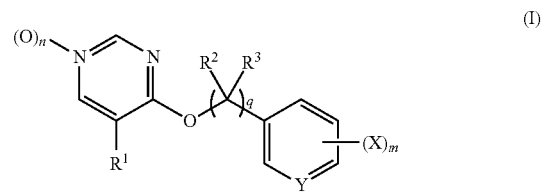

wherein $R^1$ is (a124) the following structural formula $Q^1$, $Q^2$, $Q^3$, $Q^4$, $Q^5$, $Q^6$, $Q^7$, $Q^8$, $Q^9$, $Q^{10}$, $Q^{11}$, $Q^{12}$, $Q^{13}$, $Q^{14}$, $Q^{15}$, $Q^{16}$, $Q^{17}$, $Q^{18}$, $Q^{19}$, $Q^{20}$, $Q^{21}$, $Q^{22}$, $Q^{23}$, $Q^{24}$, $Q^{25}$, $Q^{26}$, $Q^{27}$, $Q^{28}$ or $Q^{29}$

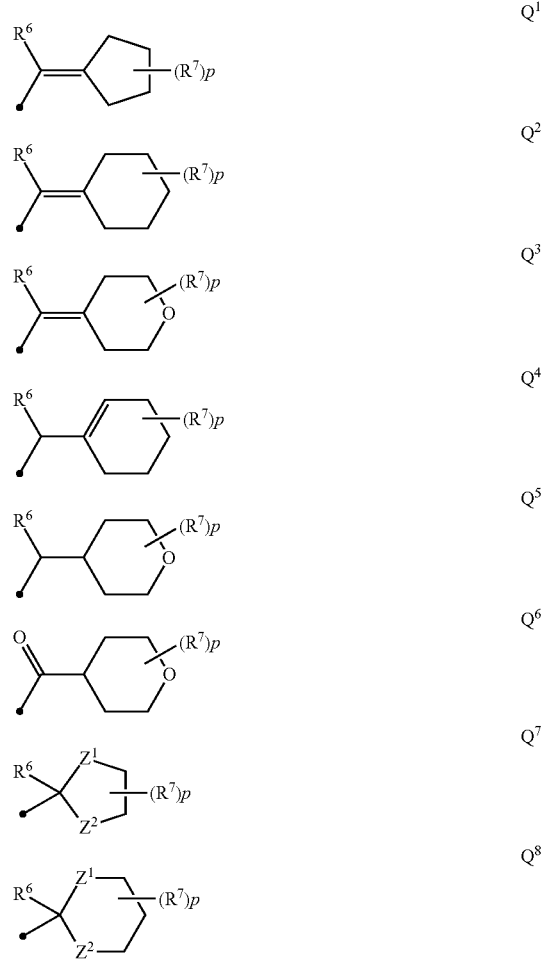

Q⁹ 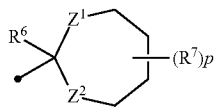

Q¹⁰ 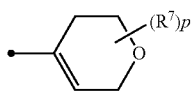

Q¹¹ 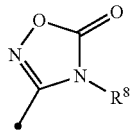

Q¹² 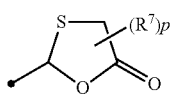

Q¹³ 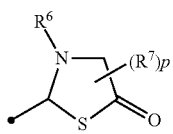

Q¹⁴ 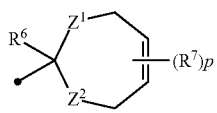

Q¹⁵ 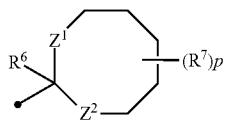

Q¹⁶ 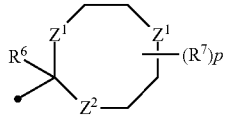

Q¹⁷ 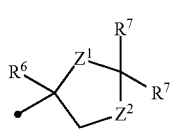

Q¹⁸ 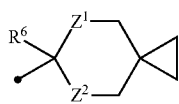

Q¹⁹ 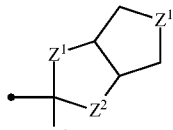

Q²⁰ 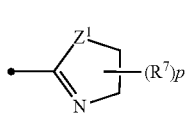

Q²¹ 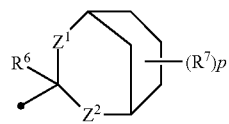

Q²² 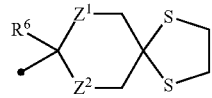

Q²³ 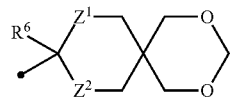

Q²⁴ 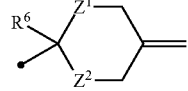

Q²⁵ 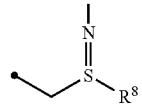

Q²⁶ 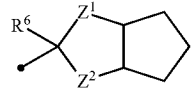

Q²⁷ 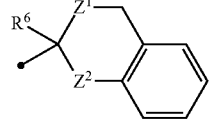

Q²⁸ 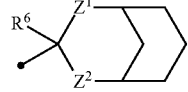

Q²⁹ 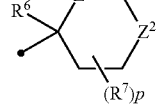

wherein $R^6$, $R^7$ and $R^8$ may be the same or different and each is a hydrogen atom, a $(C_1-C_6)$alkyl group, a $(C_3-C_6)$cycloalkyl group, a $(C_2-C_6)$alkenyl group, a $(C_2-C_6)$alkynyl group, a $(C_3-C_6)$cycloalkyl$(C_1-C_6)$alkyl group, a halo$(C_1-C_6)$alkyl group, a halo$(C_3-C_6)$cycloalkyl group, a halo$(C_2-C_6)$alkenyl group, a halo$(C_2-C_6)$alkynyl group, a halo$(C_3-C_6)$cycloalkyl$(C_1-C_6)$alkyl group, a $(C_1-C_6)$alkylcarbonyloxy$(C_1-C_6)$alkyl group, a $(C_1-C_6)$alkoxy$(C_1-C_6)$alkyl group, a hydroxy$(C_1-C_6)$alkyl group, a $(C_2-C_6)$alkenyloxy$(C_1-C_6)$alkyl group, a phenoxy$(C_1-C_6)$alkyl group, a $(C_1-C_6)$alkylsulfonyl$(C_1-C_6)$alkyl group, a $(C_1-C_6)$alkylsulfonyloxy$(C_1-C_6)$alkyl group, a halogen atom, a phenyl group, a phenyl$(C_1-C_6)$alkyl group, or a $(C_1-C_6)$alkylcarbonyl group, $R^9$ is a cyano group, a halo$(C_1-C_6)$alkyl group, or a halo$(C_1-C_6)$alkylcarbonyl group, p is an integer of 0 to 5, and $Z^1$ and $Z^2$ may be the same or different and each is a carbon atom, an oxygen atom, S, SO, SO$_2$ or NR$^6$ wherein R$^6$ is as defined above, or when p is 2, the adjacent two R$^7$ can be bonded to form a 3- to 8-membered aliphatic ring, R$^2$ and R$^3$ may be the same or different and each is
- (b1) a hydrogen atom;
- (b2) a (C$_1$-C$_8$)alkyl group;
- (b3) a (C$_3$-C$_8$)cycloalkyl group;
- (b4) a (C$_2$-C$_8$)alkenyl group;
- (b5) a (C$_2$-C$_8$)alkynyl group;
- (b6) a halo(C$_1$-C$_8$)alkyl group;
- (b7) a halo(C$_3$-C$_8$)cycloalkyl group;
- (b8) a halo(C$_2$-C$_8$)alkenyl group;
- (b9) a halo(C$_2$-C$_8$)alkynyl group;
- (b10) a (C$_3$-C$_8$)cycloalkyl(C$_1$-C$_8$)alkyl group;
- (b11) a (C$_1$-C$_8$)alkoxy(C$_1$-C$_8$)alkyl group;
- (b12) a (C$_1$-C$_8$)alkylthio(C$_1$-C$_8$)alkyl group; or
- (b13) a (C$_1$-C$_8$)alkoxycarbonyl group, q is an integer of 1 to 3, X may be the same or different and each is
- (c1) a hydrogen atom;
- (c2) a halogen atom;
- (c3) a hydroxyl group;
- (c4) a cyano group;
- (c5) a nitro group;
- (c6) an N(R$^4$)(R$^5$) group wherein R$^4$ and R$^5$ are the same or different and each is (i) a hydrogen atom, (ii) a (C$_1$-C$_6$)alkyl group, (iii) a (C$_3$-C$_6$)cycloalkyl group, (iv) a (C$_2$-C$_6$)alkenyl group, (v) a (C$_2$-C$_6$)alkynyl group, (vi) a (C$_3$-C$_6$)cycloalkyl(C$_1$-C$_6$)alkyl group, (vii) a halo(C$_1$-C$_6$)alkyl group, (viii) a halo(C$_3$-C$_6$)cycloalkyl group, (ix) a halo(C$_2$-C$_6$)alkenyl group, (x) a halo(C$_2$-C$_6$)alkynyl group, (xi) a halo(C$_3$-C$_6$)cycloalkyl(C$_1$-C$_6$)alkyl group (xii) a (C$_1$-C$_6$)alkylsulfonyl group (xiii) a (C$_1$-C$_6$)alkylcarbonyl group (xiv) a halo(C$_1$-C$_6$)alkylcarbonyl group, (xv) a (C$_1$-C$_6$)alkoxycarbonyl group, (xvi) a (C$_3$-C$_6$)cycloalkylcarbonyl group, (xvii) a phenyl group, (xviii) a phenyl group having, on the ring, the same or different 1 to 5 substituents selected from (a) a halogen atom, (b) a (C$_1$-C$_6$)alkyl group, (c) a halo(C$_1$-C$_6$)alkyl group, (d) a (C$_1$-C$_6$)alkoxv group, (e) a halo(C$_1$-C$_6$)alkoxy group, and (f) a phenoxy group, (xix) a phenoxyphenyl group having, on the ring, the same or different 1 to 5 substituents selected from (a) a halogen atom, (b) a (C$_1$-C$_6$)alkyl group, (c) a halo(C$_1$-C$_6$)alkyl group, (d) a (C$_1$-C$_6$)alkoxy group, and (e) a halo(C$_1$-C$_6$)alkoxy group, (xx) a hydroxy(C$_1$-C$_8$)alkyl group, (xxi) a phenyl(C$_1$-C$_6$)alkyl group, (xxii) a phenyl(C$_1$-C$_6$)alkyl group having, on the ring, the same or different 1 to 5 substituents selected from (a) a halogen atom, (b) a (C$_1$-C$_6$)alkyl group, (c) a halo(C$_1$-C$_6$)alkyl group, (d) a (C$_1$-C$_6$)alkoxy group, (e) halo(C$_1$-C$_6$)alkoxy group, and (f) a phenoxy group, or (xxiii) a phenoxyphenyl (C$_1$-C$_6$)alkyl group having, on the ring, the same or different 1 to 5 substituents selected from (a) a halogen atom, (b) a (C$_1$-C$_6$)alkyl group, (c) a halo(C$_1$-C$_6$)alkyl group, (d) a (C$_1$-C$_6$)alkoxy group, and (e) a halo(C$_1$-C$_6$)alkoxy group;
- (c7) an N(R$^4$)CO(R$^5$) group wherein R$^4$ and R$^5$ are as defined above;
- (c8) an N(R$^4$)SO$_2$(R$^5$) group wherein R$^4$ and R$^5$ are as defined above;
- (c9) an N(R$^4$)CO$_2$(R$^5$) group wherein R$^4$ and R$^5$ are as defined above;
- (c10) a CO(R$^4$) group wherein R$^4$ is as defined above;
- (c11) a CO$_2$(R$^4$) group wherein R$^4$ is as defined above;
- (c12) a CON(R$^4$)(R$^5$) group wherein R$^4$ and R$^5$ are as defined above;
- (c13) a C(R$^4$)=NOR$^5$ group wherein R$^4$ and R$^5$ are as defined above;
- (c14) a (C$_1$-C$_8$)alkyl group;
- (c15) a (C$_2$-C$_8$)alkenyl group;
- (c16) a (C$_2$-C$_8$)alkynyl group;
- (c17) a (C$_3$-C$_8$)cycloalkyl group;
- (c18) a halo(C$_1$-C$_8$)alkyl group;
- (c19) a halo(C$_2$-C$_8$)alkenyl group;
- (c20) a halo(C$_2$-C$_8$)alkynyl group;
- (c21) a halo(C$_3$-C$_8$)cycloalkyl group;
- (c22) a tri(C$_1$-C$_8$)alkylsilyl group wherein the alkyl groups may be the same or different;
- (c23) a tri(C$_1$-C$_8$)alkylsilyl(C$_1$-C$_8$)alkyl group wherein the alkyl groups of the tri(C$_1$-C$_8$)alkylsilyl may be the same or different;
- (c24) a (C$_3$-C$_8$)cycloalkyl(C$_1$-C$_8$)alkyl group;
- (c25) a halo(C$_3$-C$_8$)cycloalkyl(C$_1$-C$_8$)alkyl group;
- (c26) a (C$_3$-C$_8$)cycloalkyl(C$_3$-C$_8$)cycloalkyl group;
- (c27) a (C$_1$-C$_8$)alkoxy group;
- (c28) a (C$_2$-C$_8$)alkenyloxy group;
- (c29) a (C$_2$-C$_8$)alkynyloxy group;
- (c30) a (C$_3$-C$_8$)cycloalkyloxy group (said cycloalkyl is optionally fused with a benzene ring);
- (c31) a halo(C$_1$-C$_8$)alkoxy group;
- (c32) a halo(C$_2$-C$_8$)alkenyloxy group;
- (c33) a halo(C$_2$-C$_8$)alkynyloxy group;
- (c34) a halo(C$_3$-C$_8$)cycloalkyloxy group (said cycloalkyl is optionally fused with a benzene ring);
- (c35) a (C$_3$-C$_8$)cycloalkyl(C$_1$-C$_8$)alkoxy group;
- (c36) a halo(C$_3$-C$_8$)cycloalkyl(C$_1$-C$_8$)alkoxy group;
- (c37) a (C$_1$-C$_8$)alkoxy(C$_1$-C$_8$)alkyl group;
- (c38) a halo(C$_1$-C$_8$)alkoxy(C$_1$-C$_8$)alkoxy group;
- (c39) a (C$_1$-C$_8$)alkoxyhalo(C$_1$-C$_8$)alkoxy group;
- (c40) a halo(C$_1$-C$_8$)alkoxyhalo(C$_1$-C$_8$)alkoxy group;
- (c41) a mercapto group;
- (c42) a (C$_1$-C$_8$)alkylthio group;
- (c43) a (C$_2$-C$_8$)alkenylthio group;
- (c44) a (C$_2$-C$_8$)alkynylthio group;
- (c45) a (C$_3$-C$_8$)cycloalkylthio group;
- (c46) a halo(C$_1$-C$_8$)alkylthio group;
- (c47) a halo(C$_2$-C$_8$)alkenylthio group;
- (c48) a halo(C$_2$-C$_8$)alkynylthio group;
- (c49) a halo(C$_3$-C$_8$)cycloalkylthio group;
- (c50) a (C$_3$-C$_8$)cycloalkyl(C$_1$-C$_8$)alkylthio group;
- (c51) a halo(C$_3$-C$_8$)cycloalkyl(C$_1$-C$_8$)alkylthio group;
- (c52) a (C$_1$-C$_8$)alkoxy(C$_1$-C$_8$)alkylthio group;
- (c53) a halo(C$_1$-C$_8$)alkoxy(C$_1$-C$_8$)alkylthio group;
- (c54) a (C$_1$-C$_8$)alkoxyhalo(C$_1$-C$_8$)alkylthio group;
- (c55) a halo(C$_1$-C$_8$)alkoxyhalo(C$_1$-C$_8$)alkylthio group;
- (c56) a (C$_1$-C$_8$)alkylsulfinyl group;
- (c57) a (C$_2$-C$_8$)alkenylsulfinyl group;
- (c58) a (C$_2$-C$_8$)alkynylsulfinyl group;
- (c59) a (C$_3$-C$_8$)cycloalkylsulfinyl group;
- (c60) a halo(C$_1$-C$_8$)alkylsulfinyl group;
- (c61) a halo(C$_2$-C$_8$)alkenylsulfinyl group;
- (c62) a halo(C$_2$-C$_8$)alkynylsulfinyl group;
- (c63) a halo(C$_3$-C$_8$)cycloalkylsulfinyl group;
- (c64) a (C$_3$-C$_8$)cycloalkyl(C$_1$-C$_8$)alkylsulfinyl group;
- (c65) a halo(C$_3$-C$_8$)cycloalkyl(C$_1$-C$_8$)alkylsulfinyl group;
- (c66) a (C$_1$-C$_8$)alkylsulfonyl group;
- (c67) a (C$_2$-C$_8$)alkenylsulfonyl group;
- (c68) a (C$_2$-C$_8$)alkynylsulfonyl group;
- (c69) a (C$_3$-C$_8$)cycloalkylsulfonyl group;
- (c70) a halo(C$_1$-C$_8$)alkylsulfonyl group;
- (c71) a halo(C$_2$-C$_8$)alkenylsulfonyl group;

(c72) a halo($C_2$-$C_8$)alkynylsulfonyl group;
(c73) a halo($C_3$-$C_8$)cycloalkylsulfonyl group;
(c74) a ($C_3$-$C_8$)cycloalkyl($C_1$-$C_8$)alkylsulfonyl group;
(c75) a halo($C_3$-$C_8$)cycloalkyl($C_1$-$C_8$)alkylsulfonyl group;
(c76) an aryl group;
(c77) an aryl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)=NOR$^5$ group wherein $R^4$ and $R^5$ are as defined above;
(c78) an aryl($C_1$-$C_8$)alkyl group;
(c79) an aryl($C_1$-$C_6$)alkyl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)=NOR$^5$ group wherein $R^4$ and $R^5$ are as defined above;
(c80) an aryloxy group;
(c81) an aryloxy group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)=NOR$^5$ group wherein $R^4$ and $R^5$ are as defined above;
(c82) an aryloxy($C_1$-$C_8$)alkyl group;
(c83) an aryloxy($C_1$-$C_6$)alkyl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_1$-$C_6$)alkylsulfinyl group, (s) a halo($C_1$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)=NOR$^5$ group wherein $R^4$ and $R^5$ are as defined above;
(c84) an arylthio group;
(c85) an arylthio group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_2$-$C_6$)alkylsulfinyl group, (s) a halo($C_2$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)=NOR$^5$ group wherein $R^4$ and $R^5$ are as defined above;
(c86) a halo($C_1$-$C_8$)alkylenedioxy group;
(c87) a ($C_1$-$C_8$)alkoxy($C_1$-$C_8$)alkoxy group;
(c88) a ($C_3$-$C_8$)alkylene group;
(c89) a ($C_1$-$C_8$)alkyl($C_3$-$C_8$)alkylene group;

(c90) a tri($C_1$-$C_8$)alkylsilyloxy group wherein the alkyl groups may be the same or different;

(c91) a tri($C_1$-$C_8$)alkylsilyl($C_1$-$C_8$)alkoxy group wherein the alkyl groups may be the same or different;

(c92) a di($C_1$-$C_8$)alkylhalo($C_1$-$C_8$)alkylsilyl group wherein the alkyl groups may be the same or different;

(c93) a di($C_1$-$C_8$)alkyl($C_1$-$C_8$)alkylthio($C_1$-$C_8$)alkylsilyl group wherein the alkyl groups may be the same or different;

(c94) a di($C_1$-$C_8$)alkylhydroxysilyl group wherein the alkyl groups may be the same or different;

(c95) a di($C_1$-$C_8$)alkylhydrosilyl group wherein the alkyl groups may be the same or different;

(c96) a di($C_1$-$C_8$)alkylphenylsilyl group wherein the alkyl groups may be the same or different;

(c97) a ($C_1$-$C_8$)alkylthio($C_1$-$C_8$)alkoxy group;

(c98) a ($C_1$-$C_8$)alkylsulfinyl($C_1$-$C_8$)alkoxy group;

(c99) a ($C_1$-$C_8$)alkylsulfonyl($C_1$-$C_8$)alkoxy group;

(c100) a ($C_1$-$C_8$)alkoxycarbonyl($C_1$-$C_8$)alkoxy group;

(c101) a ($C_1$-$C_8$)alkylcarbonyl($C_1$-$C_8$)alkoxy group;

(c102) a cyano($C_1$-$C_8$)alkoxy group;

(c103) an aryl($C_1$-$C_8$)alkoxy group wherein the alkoxy moiety may be halogenated;

(c104) an aryl($C_1$-$C_8$)alkoxy group wherein the alkoxy moiety may be halogenated, which has, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_2$-$C_6$)alkylsulfinyl group, (s) a halo($C_2$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$$R^5$ group wherein $R^4$ and $R^5$ are as defined above, (y) an N($R^4$)SO$_2$$R^5$ group wherein $R^4$ and $R^5$ are as defined above, (z) a COR$^4$ group wherein $R^4$ is as defined above, (aa) a CO$_2$$R^4$ group wherein $R^4$ is as defined above, (bb) a CON($R^4$)$R^5$ group wherein $R^4$ and $R^5$ are as defined above, and (cc) a C($R^4$=NOR$^5$) group wherein $R^4$ and $R^5$ are as defined above;

(c105) a hydroxy($C_1$-$C_8$)alkyl group;

(c106) a ($C_1$-$C_8$)alkylthio($C_1$-$C_8$)alkylcarbonyl group;

(c107) a ($C_1$-$C_8$)alkylthio($C_1$-$C_8$)alkyl group;

(c108) a tri($C_1$-$C_8$)alkylsilyl($C_1$-$C_8$)alkylthio group wherein the alkyl groups of the tri($C_1$-$C_8$)alkylsilyl may be the same or different;

(c109) a tri($C_1$-$C_8$)alkylsilyl($C_1$-$C_8$)alkylsulfinyl group wherein the alkyl groups of the tri($C_1$-$C_8$)alkylsilyl may be the same or different;

(c110) a tri($C_1$-$C_8$)alkylsilyl($C_1$-$C_8$)alkylsulfonyl group wherein the alkyl groups of the tri($C_1$-$C_8$)alkylsilyl may be the same or different;

(c111) a $R^4$($R^5$) N($C_1$-$C_8$)alkyl group wherein $R^4$ and $R^5$ are as defined above;

(c112) a heterocyclic group;

(c113) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c114) a heterocyclyloxy group;

(c115) a heterocyclyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c116) a heterocyclylthio group;

(c117) a heterocyclylthio group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c118) a heterocyclylsulfinyl group;

(c119) a heterocyclylsulfinyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c120) a heterocyclylsulfonyl group;

(c121) a heterocyclylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c122) a heterocyclyl($C_1$-$C_8$)alkyloxy group;

(c123) a heterocyclyl($C_1$-$C_8$)alkyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$) alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$) alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl ($C_2$-$C_6$)alkynyl group wherein the alkyl groups may be the same or different, and (w) an oxo group;

(c124) a ($C_1$-$C_8$)alkyl($C_3$-$C_8$)cycloalkyl group;

(c125) a halo($C_1$-$C_8$)alkyl($C_3$-$C_8$)cycloalkyl group;

(c126) a ($C_1$-$C_8$)alkylsulfinyl($C_1$-$C_8$)alkyl group;

(c127) a di($C_1$-$C_8$)alkylbenzylsilyl group wherein the alkyl groups may be the same or different;

(c128) a heterocyclyl($C_1$-$C_8$)alkyl group;

(c129) a heterocyclyl($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl ($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, (c130) a heterocyclyloxy($C_1$-$C_8$)alkyl group; or (c131) a heterocyclyloxy($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$) alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$) alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl ($C_2$-$C_6$)alkynyl group wherein the alkyl groups may be the same or different, and (w) an oxo group, or X can form, together with the adjacent $R^2$ or $R^3$, (C132) a bicyclo ring, wherein the bicyclo ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$) alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group; or, X can form, together with the adjacent X on an aromatic ring, (C133) a bicyclo ring or (C134) a fused ring, wherein the bicyclo ring or fused ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$) alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group, Y is CH or a nitrogen atom, m is an integer of 0 to 4, n is an integer of 0 or 1, or a salt thereof.

2. The arylalkyloxypyrimidine derivative according to claim 1, wherein $R^4$, $R^5$, Y, q, m, and n are as defined in the claim 1, $R^1$ is (a124) a structural formula $Q^7$, $Q^8$, $Q^9$, $Q^{10}$, $Q^{11}$, $Q^{12}$, $Q^{13}$, $Q^{14}$, $Q^{15}$, $Q^{16}$, $Q^{17}$, $Q^{18}$, $Q^{19}$, $Q^{20}$, $Q^{21}$, $Q^{22}$, $Q^{23}$, $Q^{24}$, $Q^{25}$, $Q^{26}$, $Q^{27}$, $Q^{28}$ or $Q^{29}$ wherein each structural formula and the symbols therein are as defined in claim 1, $R^2$ and $R^3$ may be the same or different and each is (b1) a hydrogen atom; or (b6) a halo($C_1$-$C_8$)alkyl group;

X may be the same or different and each is (c1) a hydrogen atom;

(c2) a halogen atom;

(c4) a cyano group;

(c5) a nitro group;
(c10) a CO(R⁴) group wherein R⁴ is as defined above;
(c14) a $(C_1-C_8)$alkyl group;
(c18) a halo$(C_1-C_8)$alkyl group;
(c22) a tri$(C_1-C_8)$alkylsilyl group wherein the alkyl groups may be the same or different;
(c27) a $(C_1-C_8)$alkoxy group;
(c31) a halo$(C_1-C_8)$alkoxy group;
(c40) a halo$(C_1-C_8)$alkoxyhalo$(C_1-C_8)$alkoxy group;
(c42) a $(C_1-C_8)$alkylthio group;
(c46) a halo$(C_1-C_8)$alkylthio group;
(c76) an aryl group;
(c77) an aryl group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an N(R⁴)R⁵ group wherein R⁴ and R⁵ are as defined above, (w) an N(R⁴)COR⁵ group wherein R⁴ and R⁵ are as defined above, (x) an N(R⁴)CO₂R⁵ group wherein R⁴ and R⁵ are as defined above, (y) an N(R⁴)SO₂R⁵ group wherein R⁴ and R⁵ are as defined above, (z) a COR⁴ group wherein R⁴ is as defined above, (aa) a CO₂R⁴ group wherein R⁴ is as defined above, (bb) a CON(R⁴)R⁵ group wherein R⁴ and R⁵ are as defined above, and (cc) a C(R⁴)=NOR⁵ group wherein R⁴ and R⁵ are as defined above;
(c80) an aryloxy group; or
(c81) an aryloxy group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo$(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an N(R⁴)R⁵ group wherein R⁴ and R⁵ are as defined above, (w) an N(R⁴)COR⁵ group wherein R⁴ and R⁵ are as defined above, (x) an N(R⁴)CO₂R⁵ group wherein R⁴ and R⁵ are as defined above, (y) an N(R⁴)SO₂R⁵ group wherein R⁴ and R⁵ are as defined above, (z) a COR⁴ group wherein R⁴ is as defined above, (aa) a CO₂R⁴ group wherein R⁴ is as defined above, (bb) a CON(R⁴)R⁵ group wherein R⁴ and R⁵ are as defined above, and (cc) a C(R⁴)=NOR⁵ group wherein R⁴ and R⁵ are as defined above;
or a salt thereof.

3. An arylalkyloxypyrimidine derivative represented by the formula (II):

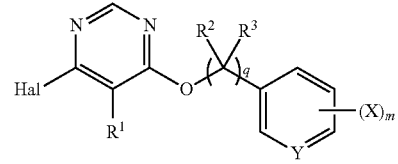

(II)

wherein R¹ is (a124) the following structural formula Q¹, Q², Q³, Q⁴, Q⁵, Q⁶, Q⁷, Q⁸, Q⁹, Q¹⁰, Q¹¹, Q¹², Q¹³, Q¹⁴, Q¹⁵, Q¹⁶, Q¹⁷, Q¹⁸, Q¹⁹, Q²⁰, Q²¹, Q²², Q²³, Q²⁴, Q²⁵, Q²⁶, Q²⁷, Q²⁸ or Q²⁹

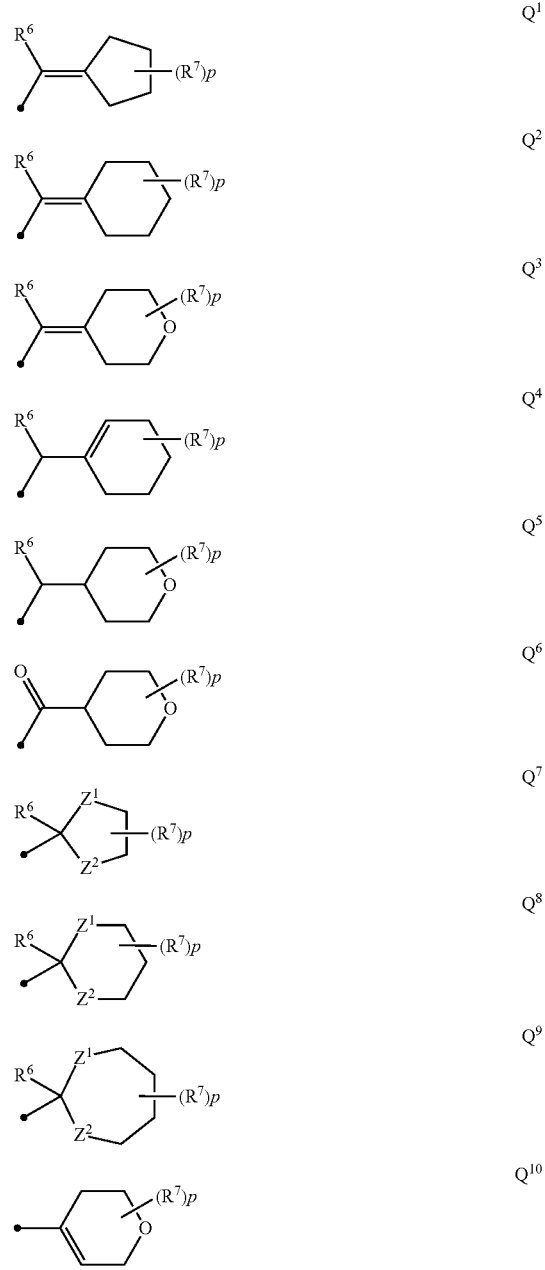

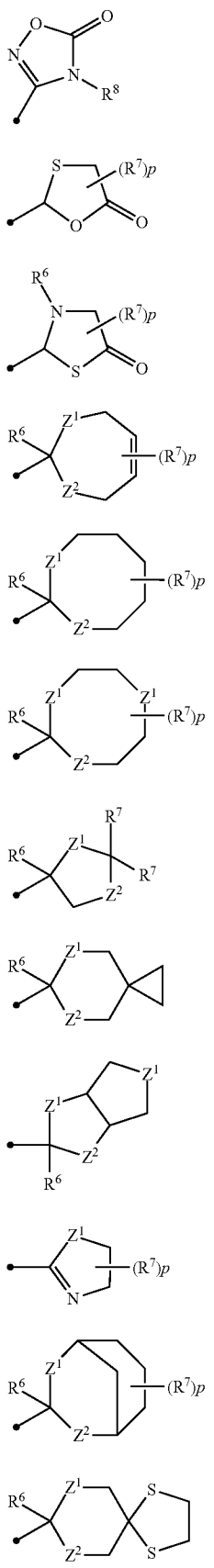
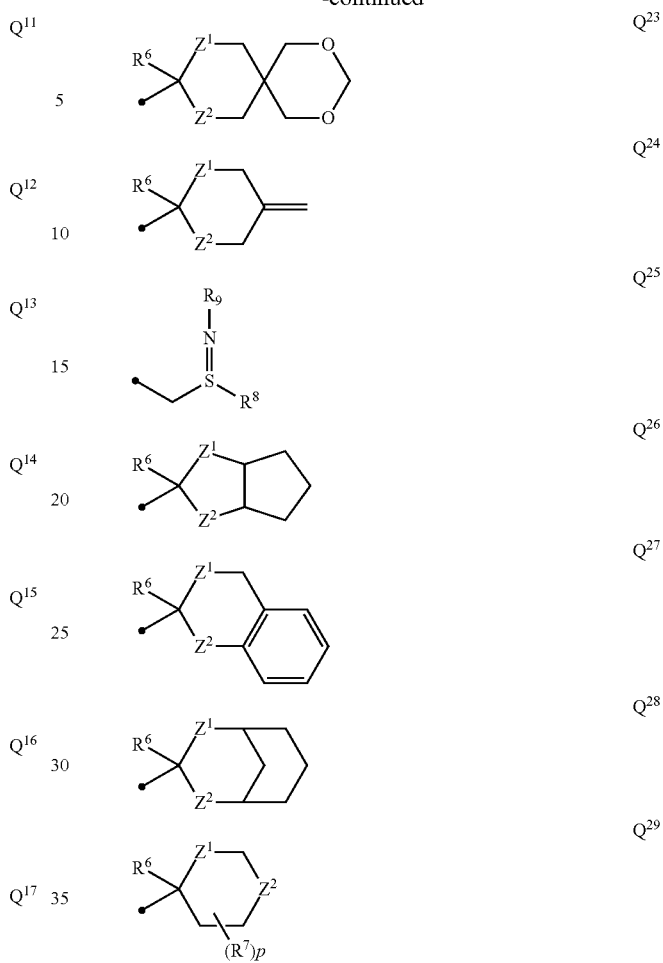

wherein $R^6$, $R^7$ and $R^8$ may be the same or different and each is a hydrogen atom, a ($C_1$-$C_6$)alkyl group, a ($C_3$-$C_6$)cycloalkyl group, a ($C_2$-$C_6$)alkenyl group, a ($C_2$-$C_6$)alkynyl group, a ($C_3$-$C_6$)cycloalkyl($C_1$-$C_6$)alkyl group, a halo($C_1$-$C_6$)alkyl group, a halo($C_3$-$C_6$)cycloalkyl group, a halo($C_2$-$C_6$)alkenyl group, a halo($C_2$-$C_6$)alkynyl group, a halo($C_3$-$C_6$)cycloalkyl($C_1$-$C_6$)alkyl group, a ($C_1$-$C_6$)alkylcarbonyloxy($C_1$-$C_6$)alkyl group, a ($C_1$-$C_6$)alkoxy($C_1$-$C_6$)alkyl group, a hydroxy($C_1$-$C_6$)alkyl group, a ($C_2$-$C_6$)alkenyloxy($C_1$-$C_6$)alkyl group, a phenoxy($C_1$-$C_6$)alkyl group, a ($C_1$-$C_6$)alkylsulfonyl($C_1$-$C_6$)alkyl group, a ($C_1$-$C_6$)alkylsulfonyloxy($C_1$-$C_6$)alkyl group, a halogen atom, a phenyl group, a phenyl($C_1$-$C_6$)alkyl group, or a ($C_1$-$C_6$)alkylcarbonyl group, $R^9$ is a cyano group, a halo($C_1$-$C_6$)alkyl group, or a halo($C_1$-$C_6$)alkylcarbonyl group, p is an integer of 0 to 5, and $Z^1$ and $Z^2$ may be the same or different and each is a carbon atom, an oxygen atom, S, SO, $SO_2$ or $NR^6$ wherein $R^6$ is as defined above, or when p is 2, the adjacent two $R^7$ can be bonded to form a 3- to 8-membered aliphatic ring, $R^2$ and $R^3$ may be the same or different and each is
(b1) a hydrogen atom;
(b2) a ($C_1$-$C_8$)alkyl group;
(b3) a ($C_3$-$C_8$)cycloalkyl group;
(b4) a ($C_2$-$C_8$)alkenyl group;
(b5) a ($C_2$-$C_8$)alkynyl group;
(b6) a halo($C_1$-$C_8$)alkyl group;

(b7) a halo($C_3$-$C_8$)cycloalkyl group;
(b8) a halo($C_2$-$C_8$)alkenyl group;
(b9) a halo($C_2$-$C_8$)alkynyl group;
(b10) a ($C_3$-$C_8$)cycloalkyl($C_1$-$C_8$)alkyl group;
(b11) a ($C_1$-$C_8$)alkoxy($C_1$-$C_8$)alkyl group;
(b12) a ($C_1$-$C_8$)alkylthio($C_1$-$C_8$)alkyl group; or
(b13) a ($C_1$-$C_8$)alkoxycarbonyl group,
q is an integer of 1 to 3,
X may be the same or different and each is
(c1) a hydrogen atom;
(c2) a halogen atom;
(c3) a hydroxyl group;
(c4) a cyano group;
(c5) a nitro group;
(c6) an N($R^4$)($R^5$) group wherein $R^4$ and $R^5$ are the same or different and each is (i) a hydrogen atom, (ii) a ($C_1$-$C_6$)alkyl group, (iii) a ($C_3$-$C_6$)cycloalkyl group, (iv) a ($C_2$-$C_6$)alkenyl group, (v) a ($C_2$-$C_6$)alkynyl group, (vi) a (C -$C_6$)cycloalkyl($C_1$-$C_6$)alkyl group, (vii) a halo($C_1$-$C_6$)alkyl group, (viii) a halo($C_3$-$C_6$)cycloalkyl group, (ix) a halo($C_2$-$C_6$)alkenyl group, (x) a halo($C_2$-$C_6$)alkynyl group, (xi) a halo($C_3$-$C_6$)cycloalkyl($C_1$-$C_6$)alkyl group (xii) a ($C_1$-$C_6$)alkylsulfonyl group (xiii) a ($C_1$-$C_6$)alkylcarbonyl group (xiv) a halo($C_1$-$C_6$)alkylcarbonyl group, (xv) a ($C_1$-$C_6$)alkoxycarbonyl group, (xvi) a ($C_3$-$C_6$)cycloalkylcarbonyl group, (xvii) a phenyl group, (xviii) a phenyl group having, on the ring, the same or different 1 to 5 substituents selected from (a) a halogen atom, (b) a ($C_1$-$C_6$)alkyl group, (c) a halo($C_1$-$C_6$)alkyl group, (d) a ($C_1$-$C_6$)alkoxv group, (e) a halo($C_1$-$C_6$)alkoxy group, and (f) a phenoxy group, (xix) a phenoxyphenyl group having, on the ring, the same or different 1 to 5 substituents selected from (a) a halogen atom, (b) a ($C_1$-$C_6$)alkyl group, (c) a halo($C_1$-$C_6$)alkyl group, (d) a ($C_1$-$C_6$)alkoxy group, and (e) a halo($C_1$-$C_6$)alkoxy group, (xx) a hydroxy($C_1$-$C_8$)alkyl group, (xxi) a phenyl($C_1$-$C_6$)alkyl group, (xxii) a phenyl($C_1$-$C_6$)alkyl group having, on the ring, the same or different 1 to 5 substituents selected from (a) a halogen atom, (b) a ($C_1$-$C_6$)alkyl group, (c) a halo($C_1$-$C_6$)alkyl group, (d) a ($c_1$-$C_6$)alkoxy group, (e) halo($C_1$-$C_6$)alkoxy group, and (f) a phenoxy group, or (xxiii) a phenoxyphenyl($C_1$-$C_6$)alkyl group having, on the ring, the same or different 1 to 5 substituents selected from (a) a halogen atom, (b) a ($C_1$-$C_6$)alkyl group, (c) a halo($C_1$-$C_6$)alkyl group, (d) a ($C_1$-$C_6$)alkoxy group, and (e) a halo($C_1$-$C_6$)alkoxy group;
(c7) an N($R^4$)CO($R^5$) group wherein $R^4$ and $R^5$ are as defined above;
(c8) an N($R^4$)$SO_2$($R^5$) group wherein $R^4$ and $R^5$ are as defined above;
(c9) an N($R^4$)$CO_2$($R^5$) group wherein $R^4$ and $R^5$ are as defined above;
(c10) a CO($R^4$) group wherein $R^4$ is as defined above;
(c11) a $CO_2$($R^4$) group wherein $R^4$ is as defined above;
(c12) a CON($R^4$)($R^5$) group wherein $R^4$ and $R^5$ are as defined above;
(c13) a C($R^4$)=NO$R^5$ group wherein $R^4$ and $R^5$ are as defined above;
(c14) a ($C_1$-$C_8$)alkyl group;
(c15) a ($C_2$-$C_8$)alkenyl group;
(c16) a ($C_2$-$C_8$)alkynyl group;
(c17) a ($C_3$-$C_8$)cycloalkyl group;
(c18) a halo($C_1$-$C_8$)alkyl group;
(c19) a halo($C_2$-$C_8$)alkenyl group;
(c20) a halo($C_2$-$C_8$)alkynyl group;
(c21) a halo($C_3$-$C_8$)cycloalkyl group;
(c22) a tri($C_1$-$C_8$)alkylsilyl group wherein the alkyl groups may be the same or different;
(c23) a tri($C_1$-$C_8$)alkylsilyl($C_1$-$C_8$)alkyl group wherein the alkyl groups of the tri($C_1$-$C_8$)alkylsilyl may be the same or different;
(c24) a ($C_3$-$C_8$)cycloalkyl($C_1$-$C_8$)alkyl group;
(c25) a halo($C_3$-$C_8$)cycloalkyl($C_1$-$C_8$)alkyl group;
(c26) a ($C_3$-$C_8$)cycloalkyl($C_3$-$C_8$)cycloalkyl group;
(c27) a ($C_1$-$C_8$)alkoxy group;
(c28) a ($C_2$-$C_8$)alkenyloxy group;
(c29) a ($C_2$-$C_8$)alkynyloxy group;
(c30) a ($C_3$-$C_8$)cycloalkyloxy group (said cycloalkyl is optionally fused with a benzene ring);
(c31) a halo($C_1$-$C_8$)alkoxy group;
(c32) a halo($C_2$-$C_8$)alkenyloxy group;
(c33) a halo($C_2$-$C_8$)alkynyloxy group;
(c34) a halo($C_3$-$C_8$)cycloalkyloxy group (said cycloalkyl is optionally fused with a benzene ring);
(c35) a ($C_3$-$C_8$)cycloalkyl($C_1$-$C_8$)alkoxy group;
(c36) a halo($C_3$-$C_8$)cycloalkyl($C_1$-$C_8$)alkoxy group;
(c37) a ($C_1$-$C_8$)alkoxy($C_1$-$C_8$)alkyl group;
(c38) a halo($C_1$-$C_8$)alkoxy($C_1$-$C_8$)alkoxy group;
(c39) a ($C_1$-$C_8$)alkoxyhalo($C_1$-$C_8$)alkoxy group;
(c40) a halo($C_1$-$C_8$)alkoxyhalo($C_1$-$C_8$)alkoxy group;
(c41) a mercapto group;
(c42) a ($C_1$-$C_8$)alkylthio group;
(c43) a ($C_2$-$C_8$)alkenylthio group;
(c44) a ($C_2$-$C_8$)alkynylthio group;
(c45) a ($C_3$-$C_8$)cycloalkylthio group;
(c46) a halo($C_1$-$C_8$)alkylthio group;
(c47) a halo($C_2$-$C_8$)alkenylthio group;
(c48) a halo($C_2$-$C_8$)alkynylthio group;
(c49) a halo($C_3$-$C_8$)cycloalkylthio group;
(c50) a ($C_3$-$C_8$)cycloalkyl($C_1$-$C_8$)alkylthio group;
(c51) a halo($C_3$-$C_8$)cycloalkyl($C_1$-$C_8$)alkylthio group;
(c52) a ($C_1$-$C_8$)alkoxy($C_1$-$C_8$)alkylthio group;
(c53) a halo($C_1$-$C_8$)alkoxy($C_1$-$C_8$)alkylthio group;
(c54) a ($C_1$-$C_8$)alkoxyhalo($C_1$-$C_8$)alkylthio group;
(c55) a halo($C_1$-$C_8$)alkoxyhalo($C_1$-$C_8$)alkylthio group;
(c56) a ($C_1$-$C_8$)alkylsulfinyl group;
(c57) a ($C_2$-$C_8$)alkenylsulfinyl group;
(c58) a ($C_2$-$C_8$)alkynylsulfinyl group;
(c59) a ($C_3$-$C_8$)cycloalkylsulfinyl group;
(c60) a halo($C_1$-$C_8$)alkylsulfinyl group;
(c61) a halo($C_2$-$C_8$)alkenylsulfinyl group;
(c62) a halo($C_2$-$C_8$)alkynylsulfinyl group;
(c63) a halo($C_3$-$C_8$)cycloalkylsulfinyl group;
(c64) a ($C_3$-$C_8$)cycloalkyl($C_1$-$C_8$)alkylsulfinyl group;
(c65) a halo($C_3$-$C_8$)cycloalkyl($C_1$-$C_8$)alkylsulfinyl group;
(c66) a ($C_1$-$C_8$)alkylsulfonyl group;
(c67) a ($C_2$-$C_8$)alkenylsulfonyl group;
(c68) a ($C_2$-$C_8$)alkynylsulfonyl group;
(c69) a ($C_3$-$C_8$)cycloalkylsulfonyl group;
(c70) a halo($C_1$-$C_8$)alkylsulfonyl group;
(c71) a halo($C_2$-$C_8$)alkenylsulfonyl group;
(c72) a halo($C_2$-$C_8$)alkynylsulfonyl group;
(c73) a halo($C_3$-$C_8$)cycloalkylsulfonyl group;
(c74) a ($C_3$-$C_8$)cycloalkyl($C_1$-$C_8$)alkylsulfonyl group;
(c75) a halo($C_3$-$C_8$)cycloalkyl($C_1$-$C_8$)alkylsulfonyl group;
(c76) an aryl group;
(c77) an aryl group having, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo $(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;

(c78) an aryl$(C_1-C_8)$alkyl group;

(c79) an aryl$(C_1-C_6)$alkyl group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo $(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;

(c80) an aryloxy group;

(c81) an aryloxy group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo $(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;

(c82) an aryloxy$(C_1-C_8)$alkyl group;

(c83) an aryloxy$(C_1-C_6)$alkyl group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo $(C_3-C_6)$cycloalkyl$(C_1-C_6)$alkoxy group, (p) a $(C_1-C_6)$alkylthio group, (q) a halo$(C_1-C_6)$alkylthio group, (r) a $(C_1-C_6)$alkylsulfinyl group, (s) a halo$(C_1-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;

(c84) an arylthio group;

(c85) an arylthio group having, on the ring, the same or different 1 to 5 substituents selected from (a) a halogen atom, (b) a cyano group, (c) a nitro group, (d) a $(C_1-C_6)$alkyl group, (e) a halo$(C_1-C_6)$alkyl group, (f) a $(C_1-C_6)$alkoxy group, (g) a halo$(C_1-C_6)$alkoxy group, (h) a $(C_2-C_6)$alkenyloxy group, (i) a halo$(C_2-C_6)$alkenyloxy group, (j) a $(C_2-C_6)$alkynyloxy group, (k) a halo$(C_2-C_6)$alkynyloxy group, (l) a $(C_3-C_6)$cycloalkoxy group, (m) a halo$(C_3-C_6)$cycloalkoxy group, (n) a $(C_3-C_6)$cycloalkyl$(C_1-C_6)$alkoxy group, (o) a halo $(C_3-C_6)$cycloalkyl$(C_1-C_6)$alkoxy group, (p) a $(C_1-C_6)$alkylthio group, (q) a halo$(C_1-C_6)$alkylthio group, (r) a $(C_2-C_6)$alkylsulfinyl group, (s) a halo$(C_2-C_6)$alkylsulfinyl group, (t) a $(C_1-C_6)$alkylsulfonyl group, (u) a halo$(C_1-C_6)$alkylsulfonyl group, (v) an $N(R^4)R^5$ group wherein $R^4$ and $R^5$ are as defined above, (w) an $N(R^4)COR^5$ group wherein $R^4$ and $R^5$ are as defined above, (x) an $N(R^4)CO_2R^5$ group wherein $R^4$ and $R^5$ are as defined above, (y) an $N(R^4)SO_2R^5$ group wherein $R^4$ and $R^5$ are as defined above, (z) a $COR^4$ group wherein $R^4$ is as defined above, (aa) a $CO_2R^4$ group wherein $R^4$ is as defined above, (bb) a $CON(R^4)R^5$ group wherein $R^4$ and $R^5$ are as defined above, and (cc) a $C(R^4)=NOR^5$ group wherein $R^4$ and $R^5$ are as defined above;

(c86) a halo$(C_1-C_8)$alkylenedioxy group;

(c87) a $(C_1-C_8)$alkoxy$(C_1-C_8)$alkoxy group;

(c88) a $(C_3-C_8)$alkylene group;

(c89) a $(C_1-C_8)$alkyl$(C_3-C_8)$alkylene group;

(c90) a tri$(C_1-C_8)$alkylsilyloxy group wherein the alkyl groups may be the same or different;

(c91) a tri$(C_1-C_8)$alkylsilyl$(C_1-C_8)$alkoxy group wherein the alkyl groups may be the same or different;

(c92) a di$(C_1-C_8)$alkylhalo$(C_1-C_8)$alkylsilyl group wherein the alkyl groups may be the same or different;

(c93) a di$(C_1-C_8)$alkyl$(C_1-C_8)$alkylthio$(C_1-C_8)$alkylsilyl group wherein the alkyl groups may be the same or different;

(c94) a di$(C_1-C_8)$alkylhydroxysilyl group wherein the alkyl groups may be the same or different;

(c95) a di($C_1$-$C_8$)alkylhydrosilyl group wherein the alkyl groups may be the same or different;
(c96) a di($C_1$-$C_8$)alkylphenylsilyl group wherein the alkyl groups may be the same or different;
(c97) a ($C_1$-$C_8$)alkylthio($C_1$-$C_8$)alkoxy group;
(c98) a ($C_1$-$C_8$)alkylsulfinyl($C_1$-$C_8$)alkoxy group;
(c99) a ($C_1$-$C_8$)alkylsulfonyl($C_1$-$C_8$)alkoxy group;
(c100) a ($C_1$-$C_8$)alkoxycarbonyl($C_1$-$C_8$)alkoxy group;
(c101) a ($C_1$-$C_8$)alkylcarbonyl($C_1$-$C_8$)alkoxy group;
(c102) a cyano($C_1$-$C_8$)alkoxy group;
(c103) an aryl($C_1$-$C_8$)alkoxy group wherein the alkoxy moiety may be halogenated;
(c104) an aryl($C_1$-$C_8$)alkoxy group wherein the alkoxy moiety may be halogenated, which has, on the ring, the same or different 1 to 5 substituents selected from (a) a halogen atom, (b) a cyano group, (c) a nitro group, (d) a ($C_1$-$C_6$)alkyl group, (e) a halo($C_1$-$C_6$)alkyl group, (f) a ($C_1$-$C_6$)alkoxy group, (g) a halo($C_1$-$C_6$)alkoxy group, (h) a ($C_2$-$C_6$)alkenyloxy group, (i) a halo($C_2$-$C_6$)alkenyloxy group, (j) a ($C_2$-$C_6$)alkynyloxy group, (k) a halo($C_2$-$C_6$)alkynyloxy group, (l) a ($C_3$-$C_6$)cycloalkoxy group, (m) a halo($C_3$-$C_6$)cycloalkoxy group, (n) a ($C_3$-$C_6$)cycloalkyl($C_1$-$C_6$)alkoxy group, (o) a halo($C_3$-$C_6$)cycloalkyl($C_1$-$C_6$)alkoxy group, (p) a ($C_1$-$C_6$)alkylthio group, (q) a halo($C_1$-$C_6$)alkylthio group, (r) a ($C_2$-$C_6$)alkylsulfinyl group, (s) a halo($C_2$-$C_6$)alkylsulfinyl group, (t) a ($C_1$-$C_6$)alkylsulfonyl group, (u) a halo($C_1$-$C_6$)alkylsulfonyl group, (v) an N($R^4$)$R^5$ group wherein $R^4$ and $R^5$ are as defined above, (w) an N($R^4$)COR$^5$ group wherein $R^4$ and $R^5$ are as defined above, (x) an N($R^4$)CO$_2$R$^5$ group wherein $R^4$ and $R^5$ are as defined above, (y) an N($R^4$)SO$_2$R$^5$ group wherein $R^4$ and $R^5$ are as defined above, (z) a COR$^4$ group wherein $R^4$ is as defined above, (aa) a CO$_2$R$^4$ group wherein $R^4$ is as defined above, (bb) a CON($R^4$)$R^5$ group wherein $R^4$ and $R^5$ are as defined above, and (cc) a C($R^4$)=NOR$^5$ group wherein $R^4$ and $R^5$ are as defined above;
(c105) a hydroxy($C_1$-$C_8$)alkyl group;
(c106) a ($C_1$-$C_8$)alkylthio($C_1$-$C_8$)alkylcarbonyl group;
(c107) a ($C_1$-$C_8$)alkylthio($C_1$-$C_8$)alkyl group;
(c108) a tri($C_1$-$C_8$)alkylsilyl($C_1$-$C_8$)alkylthio group wherein the alkyl groups of the tri($C_1$-$C_8$)alkylsilyl may be the same or different;
(c109) a tri($C_1$-$C_8$)alkylsilyl($C_1$-$C_8$)alkylsulfinyl group wherein the alkyl groups of the tri($C_1$-$C_8$)alkylsilyl may be the same or different;
(c110) a tri($C_1$-$C_8$)alkylsilyl($C_1$-$C_8$)alkylsulfonyl group wherein the alkyl groups of the tri($C_1$-$C_8$)alkylsilyl may be the same or different;
(c111) a $R^4$($R^5$) N($C_1$-$C_8$)alkyl group wherein $R^4$ and $R^5$ are as defined above;
(c112) a heterocyclic group;
(c113) a heterocyclic group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;
(c114) a heterocyclyloxy group;
(c115) a heterocyclyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;
(c116) a heterocyclylthio group;
(c117) a heterocyclylthio group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;
(c118) a heterocyclylsulfinyl group;
(c119) a heterocyclylsulfinyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4$($R^5$)N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;
(c120) a heterocyclylsulfonyl group;
(c121) a heterocyclylsulfonyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c122) a heterocyclyl($C_1$-$C_8$)alkyloxy group;

(c123) a heterocyclyl($C_1$-$C_8$)alkyloxy group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group;

(c124) a ($C_1$-$C_8$)alkyl($C_3$-$C_8$)cycloalkyl group;

(c125) a halo($C_1$-$C_8$)alkyl($C_3$-$C_8$)cycloalkyl group;

(c126) a ($C_1$-$C_8$)alkylsulfinyl($C_1$-$C_8$)alkyl group;

(c127) a di($C_1$-$C_8$)alkylbenzylsilyl group wherein the alkyl groups may be the same or different;

(c128) a heterocyclyl($C_1$-$C_8$)alkyl group;

(c129) a heterocyclyl($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-C6)alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$)alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl($C_2$-$C_6$)alkynyl group wherein the alkyl groups may be the same or different, and (w) an oxo group, (c130) a heterocyclyloxy($C_1$-$C_8$)alkyl group; or (c131) a heterocyclyloxy($C_1$-$C_8$)alkyl group having, on the ring, the same or different 1 to 5 substituents selected from (a) a halogen atom, (b) a cyano group, (c) a nitro group, (d) a formyl group, (e) a ($C_1$-$C_6$)alkyl group, (f) a halo($C_1$-$C_6$)alkyl group, (g) a ($C_1$-$C_6$) alkoxy group, (h) a halo($C_1$-$C_6$)alkoxy group, (i) a ($C_3$-$C_6$)cycloalkyl($C_1$-$C_6$)alkoxy group, (j) a ($C_1$-$C_6$) alkylthio group, (k) a halo($C_1$-$C_6$)alkylthio group, (l) a ($C_1$-$C_6$)alkylsulfinyl group, (m) a halo($C_1$-$C_6$)alkylsulfinyl group, (n) a ($C_1$-$C_6$)alkylsulfonyl group, (o) a halo($C_1$-$C_6$)alkylsulfonyl group, (p) a ($C_1$-$C_6$)alkylcarbonyl group, (q) a carboxyl group, (r) a ($C_1$-$C_6$)alkoxycarbonyl group, (s) a $R^4(R^5)$N carbonyl group wherein $R^4$ and $R^5$ are as defined above, (t) a ($C_2$-$C_6$)alkynyl group, (u) a tri($C_1$-$C_6$)alkylsilyl($C_1$-$C_6$)alkyl group wherein the alkyl groups of the tri($C_1$-$C_6$)alkylsilyl may be the same or different, (v) a tri($C_1$-$C_6$)alkylsilyl ($C_2$-$C_6$)alkynyl group wherein the alkyl groups may be the same or different, and (w) an oxo group, or X can form, together with the adjacent $R^2$ or $R^3$, (C132) a bicyclo ring, wherein the bicyclo ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group; or, X can form, together with the adjacent X on an aromatic ring, (C133) a bicyclo ring or (C134) a fused ring, wherein the bicyclo ring or fused ring optionally has the same or different one or more substituents selected from (a) a halogen atom, (b) a ($C_1$-$C_6$)alkyl group, (c) a halo($C_1$-$C_6$)alkyl group, (d) a ($C_1$-$C_6$)alkoxy group, (e) a halo($C_1$-$C_6$)alkoxy group, (f) a ($C_1$-$C_6$)alkylthio group, (g) a halo($C_1$-$C_6$)alkylthio group, (h) a ($C_1$-$C_6$)alkylsulfinyl group, (i) a halo($C_1$-$C_6$)alkylsulfinyl group, (j) a ($C_1$-$C_6$)alkylsulfonyl group, and (k) a halo($C_1$-$C_6$)alkylsulfonyl group, Y is CH or a nitrogen atom, m is an integer of 0 to 4, and Hal is a halogen atom, or a salt thereof.

4. An agrohorticultural insecticide comprising the arylalkyloxypyrimidine derivative according to claim 1 or a salt thereof as an active ingredient.

5. An agrohorticultural insecticide comprising the arylalkyloxypyrimidine derivative according to claim 2 or a salt thereof as an active ingredient.

6. A method of using an agrohorticultural insecticide, which comprises treating a plant or soil with the arylalkyloxypyrimidine derivative according to claim 1 or a salt thereof.

7. A method of controlling an agrohorticultural pest, which comprises treating a plant or soil with the arylalkyloxypyrimidine derivative according to claim 1 or a salt thereof.

8. A method of using an agrohorticultural insecticide, which comprises treating a plant or soil with the arylalkyloxypyrimidine derivative according to claim 2 or a salt thereof.

9. A method of controlling an agrohorticultural pest, which comprises treating a plant or soil with the arylalkyloxypyrimidine derivative according to claim 2 or a salt thereof.

\* \* \* \* \*